US012227515B2

(12) United States Patent
Lazo et al.

(10) Patent No.: US 12,227,515 B2
(45) Date of Patent: Feb. 18, 2025

(54) IN-FLOW PHOTOOXYGENATION OF AMINOTHIENOPYRIDINONES GENERATES NOVEL PTP4A3 PHOSPHATASE INHIBITORS

(71) Applicants: University of Virginia Patent Foundation, Charlottesville, VA (US); University of Pittsburgh—Of the Commonwealth System of Higher Education, Pittsburgh, PA (US)

(72) Inventors: John S. Lazo, Charlottesville, VA (US); Elizabeth Sharlow, Butler, PA (US); Peter Wipf, Pittsburgh, PA (US); Nikhil Tasker, Trumbull, CT (US); Ettore Rastelli, Pittsburgh, PA (US)

(73) Assignees: University of Virginia Patent Foundation, Charlottesville, VA (US); University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 745 days.

(21) Appl. No.: 17/309,259

(22) PCT Filed: Nov. 12, 2019

(86) PCT No.: PCT/US2019/061003
§ 371 (c)(1),
(2) Date: May 12, 2021

(87) PCT Pub. No.: WO2020/102243
PCT Pub. Date: May 22, 2020

(65) Prior Publication Data
US 2022/0017534 A1    Jan. 20, 2022

Related U.S. Application Data

(60) Provisional application No. 62/870,252, filed on Jul. 3, 2019, provisional application No. 62/758,759, filed on Nov. 12, 2018, provisional application No. 62/758,861, filed on Nov. 12, 2018.

(51) Int. Cl.
C07D 495/04       (2006.01)
(52) U.S. Cl.
CPC .................. C07D 495/04 (2013.01)
(58) Field of Classification Search
CPC .... C07D 495/04; A61K 31/4365; A61P 35/00
See application file for complete search history.

(56) References Cited

U.S. PATENT DOCUMENTS

2021/0395266 A1    12/2021    Lazo et al.

FOREIGN PATENT DOCUMENTS

| EP | 3880684 | 11/2022 | |
|---|---|---|---|
| WO | WO-2013170147 A1 | 11/2013 | |
| WO | WO-2016205534 A1 * | 12/2016 | ......... A61K 31/4365 |
| WO | WO-2020102243 A2 | 5/2020 | |
| WO | WO-2020102243 A3 | 5/2020 | |
| WO | WO-2020102245 A1 | 5/2020 | |

OTHER PUBLICATIONS

Wei, M., Korotkov, K. V., & Blackburn, J. S. Targeting phosphatases of regenerating liver (PRLs) in cancer. Pharmacology & Therapeutics, 190, 128-138. https://doi.org/10.1016/j.pharmthera.2018.05.014 (Year: 2018).*
Morita. Literature Seminar. Application of Bioisosteres in Drug Design. (Year: 2012).*
"International Application Serial No. PCT/US2019/061003, International Search Report mailed Jun. 25, 2020", 6 pgs.
"International Application Serial No. PCT/US2019/061003, Invitation to Pay Additional Fees mailed Apr. 21, 2020", 12 pgs.
"International Application Serial No. PCT/US2019/061003, Written Opinion mailed Jun. 25, 2020", 11 pgs.
"International Application Serial No. PCT/US2019/061007, International Search Report mailed Mar. 16, 2020", 5 pgs.
"International Application Serial No. PCT/US2019/061007, Written Opinion mailed Mar. 16, 2020", 5 pgs.
Hyun, Seop Tae, et al., "Identification of Hydrophobic Tags for the Degradation of Stabilized Proteins", Chembiochem, vol. 13, No. 4, (Mar. 5, 2012), 538-541.
Salamoun, Joseph M, et al., "Photooxygenation of an aminothienopyridone yields a more potent PTP4A3 inhibitor", Organic & Biomolecular Chemistry vol. 14, No. 27, (Jun. 7, 2016), 6398-6402 pgs.
Tasker, Nikhil R, et al., "In-flow photooxygenation of aminothienopyridinones generates iminopyridinedione PTP4A3 phosphatase inhibitors", Organic & Biomolecular Chemistry, vol. 17, No. 9, (Jan. 1, 2019), 2448-2466.
"International Application Serial No. PCT/US2019/061003, International Preliminary Report on Patentability mailed May 20, 2021", 13 pgs.
"International Application Serial No. PCT/US2019/061007, International Preliminary Report on Patentability mailed May 20, 2021", 7 pgs.
"European Application Serial No. 19836207.1, Response filed Dec. 21, 2021 to Communication pursuant to Rules 161(1) and 162 EPC", 95 pgs.
"European Application Serial No. 19836206.3, Response filed Dec. 20, 2021 to Communication pursuant to Rules 161(1) and 162 EPC", 5 pgs.
Fontanillo, Miriam, et al., "Phosphatases: Their Roles in Cancer and Their Chemical Modulators", Böldicke, T. (eds) Protein Targeting Compounds. Advances in Experimental Medicine and Biology, vol. 917. Springer, Cham. https://doi.org/10.1007/978-3-319-32805-8_10, (May 29, 2016), 209-240.

(Continued)

*Primary Examiner* — Yih-Horng Shiao
*Assistant Examiner* — Hoi Yan Nmn Lee
(74) *Attorney, Agent, or Firm* — Schwegman Lundberg & Woessner, P.A.

(57) ABSTRACT

The disclosure provides compounds that inhibit protein tyrosine phosphatase, such as protein tyrosine phosphatase 4 A3 (PTP4A3). The disclosure also provides pharmaceutical compositions, uses, and methods of using the compounds, such as in the treatment of cancers.

8 Claims, No Drawings

(56) References Cited

OTHER PUBLICATIONS

Lazo, John S, et al., "Small molecule targeting of PTPs in cancer", J. Biochem. Cell Biol., 96, (Mar. 2018), 171-181.

McQueeney, Kelley E, et al., "A chemical genetics approach identifies PTP4A3 as a regulator of colon cancer cell adhesion", FASEB J., 32(10), [Online] Retrieved from the Internet: <URL: https://www.ncbi.nlm.nih.gov/pmc/articles/PMC6133700/>, (May 2018), 5661-5673.

McQueeney, Kelley E, et al., "Targeting ovarian cancer and endothelium with an allosteric PTP4A3 phosphatase inhibitor", Oncotarget, vol. 9, No. 9, [Online] Retrieved from the Internet: <URL: www.impactjournals.com/oncotarget/>, (2018), 8223-8240.

Sharlow, Elizabeth R, et al., "Investigational inhibitors of PTP4A3 phosphatase as antineoplastic agents", Expert Opin. Investig. Drugs, vol. 23, No. 5, (Mar. 13, 2014), 661-673.

Wei, Min, et al., "Targeting phosphatases of regenerating liver (PRLs) in cancer", Pharmacol. Ther., 190, (2018), 128-138.

Zhang, Huizhi, et al., "PRL3 phosphatase active site is required for binding the putative magnesium transporter CNNM3", Scientific Reports, 7:48, [Online] Retrieved from the Internet: <URL: https://www.nature.com/scientificreports>, (2017), 9 pgs.

U.S. Appl. No. 17/309,260, filed May 12, 2021, In-Flow Photooxygenation of Aminothienopyridinones Generates Novel PTP4A3 Phosphatase Inhibitors.

"U.S. Appl. No. 17/309,260, Non Final Office Action mailed Apr. 3, 2024", 42 pgs.

"U.S. Appl. No. 17/309,260, Response filed Feb. 23, 2024 to Restriction Requirement mailed Dec. 11, 2023", 5 pgs.

Auzely-Velty, R, et al., "New Supramolecular Assemblies of a Cyclodextrin-Grafted Chitosan through Specific Complexation", Macromolecules, 35(21),, [Online] Retrieved from the internet: <https://doi.org/10.1021/ma0206640>, (2002), 7955-7962.

Grava, "(Abstract Only) Synthesis of 1-adamantyl and (1-adamantylmethyl) alkyl ketones", Zhurnal Organicheskoi Khimii, 17(4), (1981), 778-786.

Liu, J, et al., "The many faces of the adamantyl group in drug design", European Journal of Medicinal Chemistry, 46(6), [Online] Retrieved from the internet: <https://doi.Org/10.1016/j.ejmech.2011.01.047>, (2011), 1949-1963.

"U.S. Appl. No. 17/309,260, Restriction Requirement mailed Dec. 11, 2023", 9 pgs.

\* cited by examiner

IN-FLOW PHOTOOXYGENATION OF AMINOTHIENOPYRIDINONES GENERATES NOVEL PTP4A3 PHOSPHATASE INHIBITORS

RELATED APPLICATIONS

The present application is a U.S. national stage application under 35 U.S.C. § 371 of PCT Patent Application No. PCT/US2019/061003, filed on Nov. 12, 2019, which claims the benefit of priority to U.S. Provisional Patent Applications Nos. 62/758,759 and 62/758,861 each filed on Nov. 12, 2018, and No. 62/870,252 filed on Jul. 3, 2019, each of which applications are incorporated as if fully set forth herein.

GOVERNMENT LICENSE RIGHTS

This invention was made with government support under Grants No. W81XWH-18-1-0012 and No. W81XWH-18-1-0011 awarded by the U.S. Department of Defense U.S. Army Medical Research and Materiel Command. The government has certain rights in the invention.

BACKGROUND

Phosphatases, as therapeutic targets, offer a largely underexplored opportunity for the discovery of novel drugs and expansion of the current state of the art in medicinal chemistry. In recent years, the protein tyrosine phosphatase 4A family (PTP4A1, PTP4A2, and PTP4A3) has garnered much interest and ample validation as an anticancer target. All three phosphatases are ~20 kD and possess a unique C-terminal prenylation motif important for association with the plasma membrane and early endosomes. There is no established substrate for any PTP4A family member.

Compared to other phosphatases, PTP4A3 has a higher rate of overexpression in many cancer cell lines, such as leukemia and blood cancers, and especially in colorectal cancer, potentially allowing for a more selective inhibition by drug molecules. In addition, advanced ovarian cancer and triple negative breast cancer respond poorly to existing drugs and, thus, demand new therapies. The protein tyrosine phosphatase PTP4A3 (Phosphatase of Regenerating Liver-3, PRL-3) also is overexpressed in these cancer tissues.[19] PTP4A3 also promotes cancer cell migration and invasion, and it is believed to be the most oncogenic of all tyrosine phosphatases.[21] Further, elevated levels of PTP4A3 mRNA were first observed in metastatic colorectal cancer and is associated with late stage metastatic disease.

Other human cancers express high PTP4A3 levels including, but not restricted to tumors of the breast, ovary, cervix, lung, brain, prostate, liver, stomach, and stroma and to leukemias and lymphomas. Elevated PTP4A3 expression often correlates with increased tumor invasiveness and poor prognosis; ectopic PTP4A3 overexpression enhances tumor cell migration and invasion in vitro. PTP4A3 also has been proposed to have a role in the progression of cardiac hypertrophy by inhibiting intracellular calcium mobilization in response to angiotensin II.

SUMMARY

The present disclosure provides in one embodiment a compound, or a pharmaceutically acceptable salt thereof, selected from the following table:

3
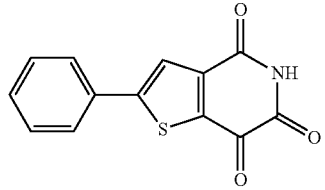 [SMILES: O=C1NC(=O)c2cc(-c3ccccc3)sc2C1=O]

15
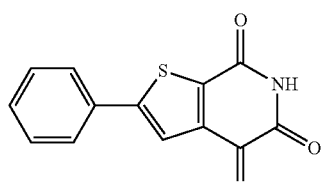

9a
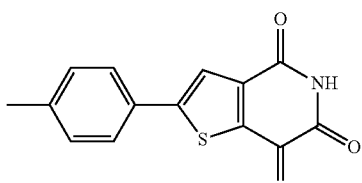

9b
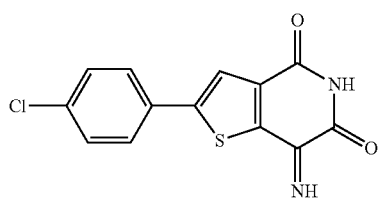 [SMILES: N=C1C(=O)NC(=O)c2cc(-c3ccc(Cl)cc3)sc21]

9c
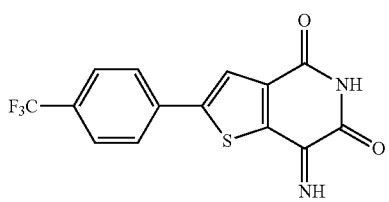 [SMILES: N=C1C(=O)NC(=O)c2cc(-c3ccc(C(F)(F)F)cc3)sc21]

9d
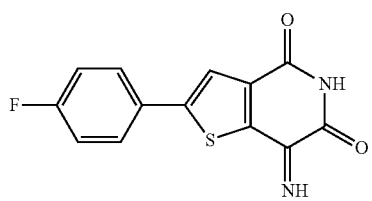

9e
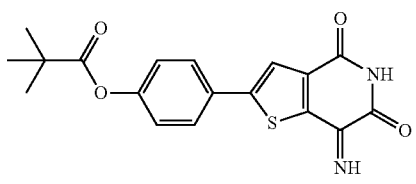 [SMILES: CC(C)(C)C(=O)Oc1ccc(-c2cc3c(s2)C(=N)C(=O)NC3=O)cc1]

9f
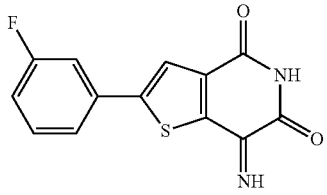 [SMILES: N=C1C(=O)NC(=O)c2cc(-c3cccc(F)c3)sc21]

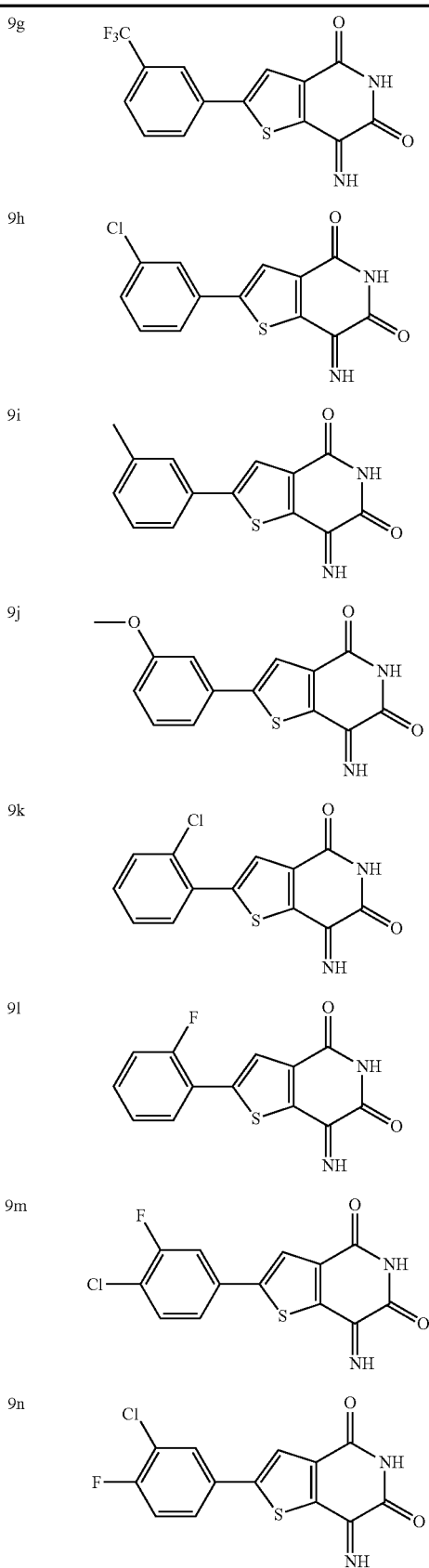
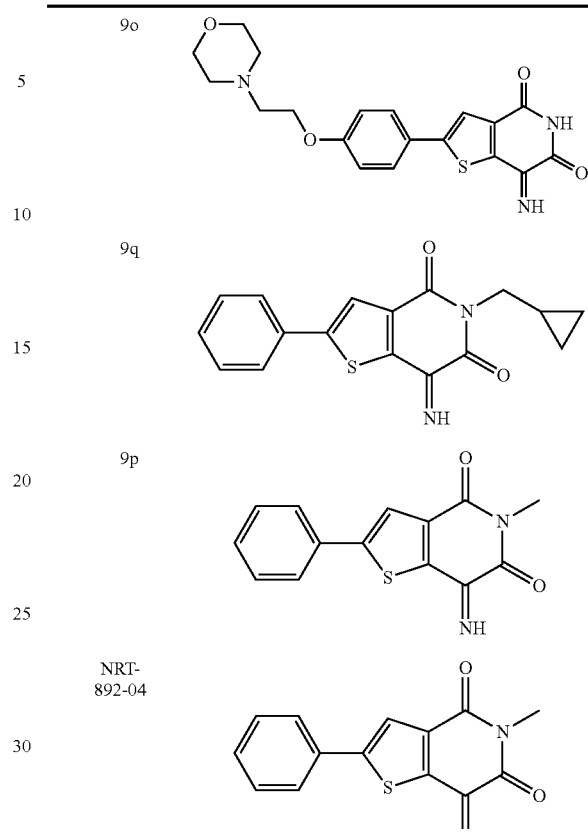
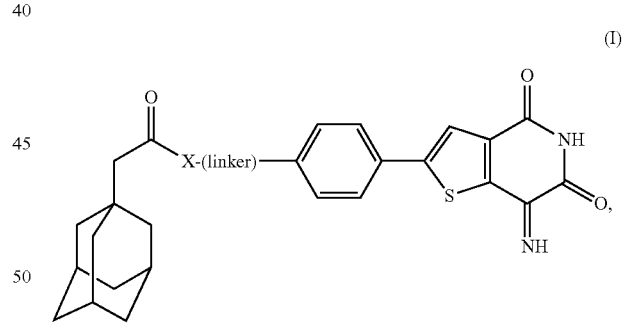

In another embodiment, the present disclosure provides a compound according to Formula (I), or a pharmaceutically acceptable salt thereof:

(I)

wherein X is O or NH; and (linker) is a linker moiety.

Yet another embodiment of the disclosure is a method for treating a subject suffering from cancer. The method comprises administering to the subject a therapeutically effective amount of a compound described herein or a pharmaceutically acceptable salt thereof.

The present disclosure also provides, in an embodiment, a method for inhibiting a protein-tyrosine phosphatase in a cell. The method comprises contacting the cell with a compound described herein or a pharmaceutically acceptable salt thereof.

Also provided, in various embodiments, is the use of a compound as described herein, or a pharmaceutically acceptable salt thereof, in the manufacture of a medicament for treating cancer or for inhibiting a protein tyrosine phosphatase in a cell.

Another embodiment of the present disclosure is a compound as described herein, or a pharmaceutically acceptable salt thereof, for use in the treatment of cancer in a subject.

The present disclosure, in yet another embodiment, also relates to pharmaceutical composition comprising a therapeutically effective amount of a compound as described herein, or a pharmaceutically acceptable salt thereof.

DETAILED DESCRIPTION

Definitions

In describing and claiming the various embodiments, the following terminology will be used in accordance with the definitions set forth below. Unless defined otherwise, all technical and scientific terms used herein have the commonly understood by one of ordinary skill in the art to which the present disclosure pertains. Although any methods and materials similar or equivalent to those described herein may be useful in the practice or testing of the embodiments, exemplary methods and materials are described below. Specific terminology of particular importance to the description of the present disclosure is defined below.

The articles "a" and "an" are used herein to refer to one or to more than one (i.e., to at least one) of the grammatical object of the article. For example, "an element" means one element or more than one element.

The term "about," as used herein, means approximately, in the region of, roughly, or around. When the term "about" is used in conjunction with a numerical range, it modifies that range by extending the boundaries above and below the numerical values set forth. For example, the term "about" is used herein to modify a numerical value above and below the stated value by a variance of 5%, 10%, 15%, or 20%.

As use herein, the terms "administration of" and or "administering" a compound should be understood to mean providing a compound of the present disclosure to a subject in need of treatment.

As used herein, "alleviating a disease or disorder symptom," means reducing the severity of the symptom or the frequency with which such a symptom is experienced by a subject, or both.

A "compound," as used herein, refers to any type of substance or agent that is commonly considered a drug, or a candidate for use as a drug, as well as combinations and mixtures of the above. The term "compound" is intended to encompass not only the specified molecular entity but also its pharmaceutically acceptable, pharmacologically active analogs, including, but not limited to, salts, polymorphs, esters, amides, prodrugs, adducts, conjugates, active metabolites, and the like, where such modifications to the molecular entity are appropriate.

The term "delivery vehicle" refers to any kind of device or material that can be used to deliver compounds in vivo or can be added to a composition comprising compounds administered to a plant or animal. This includes, but is not limited to, implantable devices, aggregates of cells, matrix materials, gels, etc.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used in the specification and the appended claims, the terms "for example," "for instance," "such as," "including" and the like are meant to introduce examples that further clarify more general subject matter. Unless otherwise specified, these examples are provided only as an aid for understanding the present disclosure, and are not meant to be limiting in any fashion.

The terms "formula" and "structure" are used interchangeably herein.

The term "inhibit" or "inhibition" as used herein, refers to the ability of a compound of the present disclosure to regulate, reduce, or impede a described function, interaction, or activity. For example, inhibition is by at least 10%, at least 25%, at least 50%, or at least 75%. The terms "inhibit", "reduce", and "block" are used interchangeably herein.

As used herein "injecting or applying" includes administration of a compound of the present disclosure by any number of routes and means including, but not limited to, topical, oral, buccal, intravenous, intramuscular, intraarterial, intramedullary, intrathecal, intraventricular, transdermal, subcutaneous, intraperitoneal, intranasal, enteral, topical, sublingual, vaginal, ophthalmic, pulmonary, or rectal means.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

The term "prevent," as used herein, means to stop something from happening, or taking advance measures against something possible or probable from happening. In the context of medicine, "prevention" generally refers to action taken to decrease the chance of getting a disease or condition.

A "patient" or subject" includes an animal, such as a human, cow, horse, sheep, lamb, pig, chicken, turkey, quail, cat, dog, mouse, rat, rabbit or guinea pig. In accordance with some embodiments, the animal is a mammal such as a non-primate and a primate (e.g., monkey and human). In one embodiment, a patient is a human, such as a human infant, child, adolescent or adult. In the present disclosure, the terms "patient" and "subject" are used interchangeably.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

Compounds

The present disclosure provides in various embodiments a compound, or a pharmaceutically acceptable salt thereof, selected from the following table:

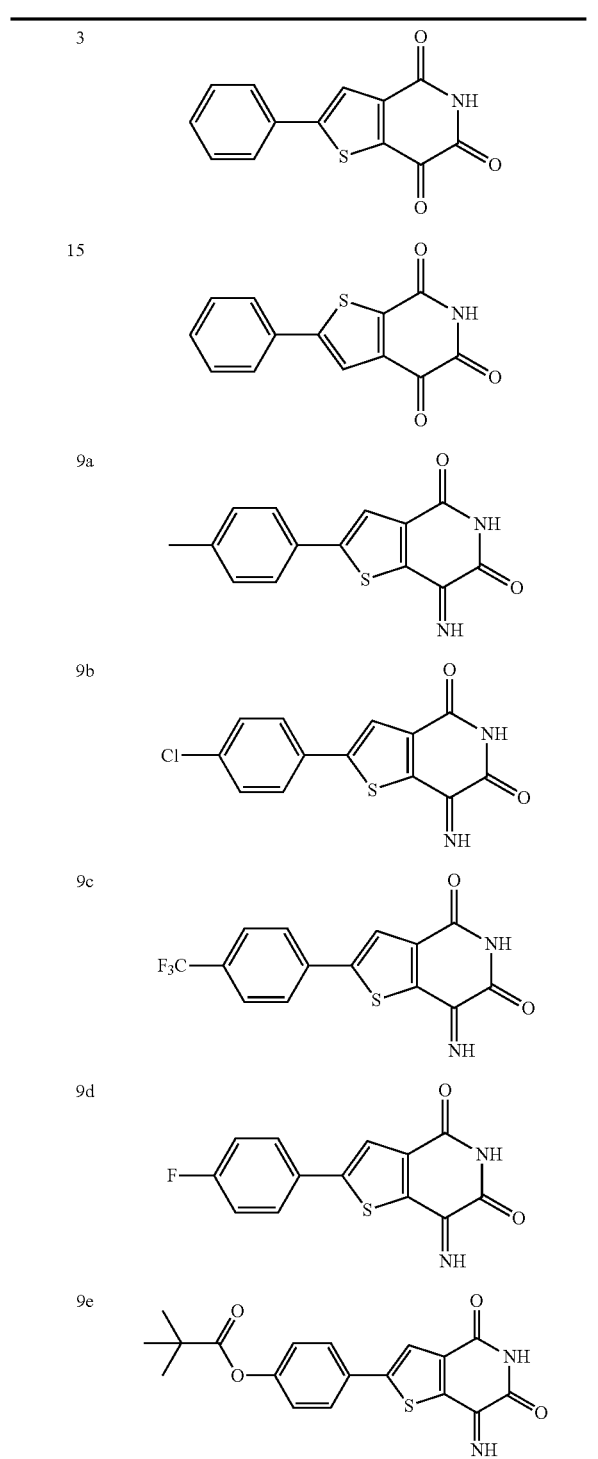

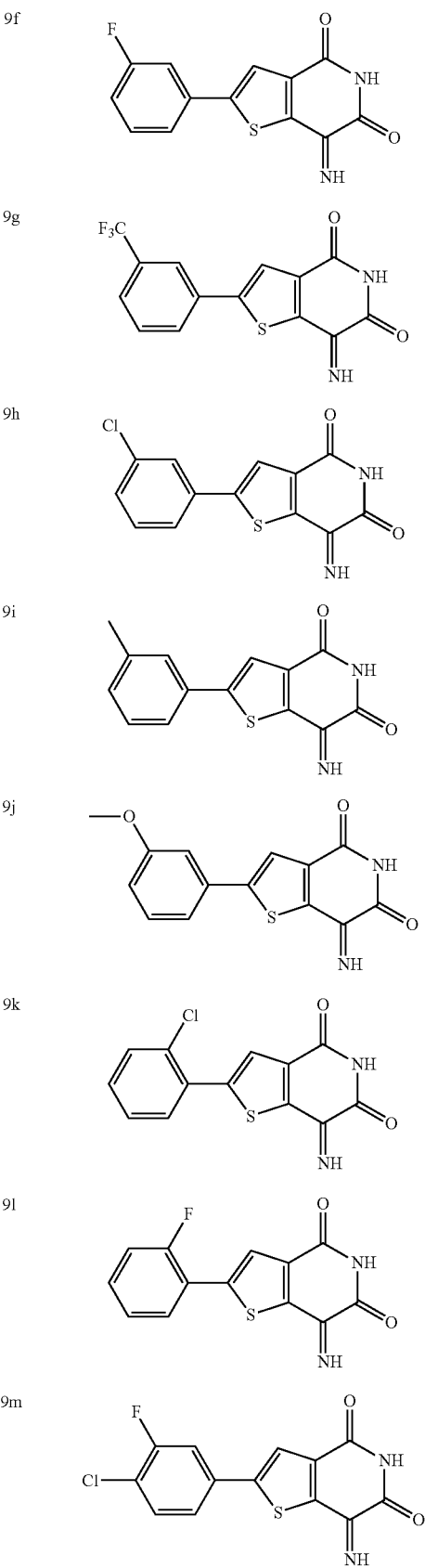

-continued

9n 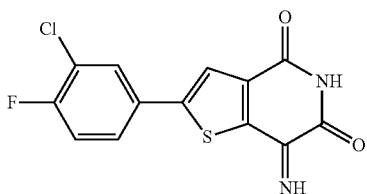 [SMILES: N=C1C(=O)NC(=O)c2cc(-c3ccc(F)c(Cl)c3)sc21]

9o 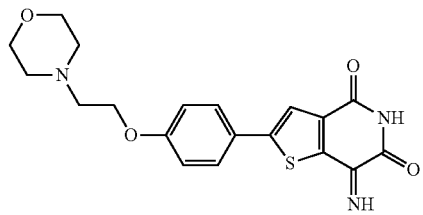 [SMILES: N=C1C(=O)NC(=O)c2cc(-c3ccc(OCCN4CCOCC4)cc3)sc21]

9q 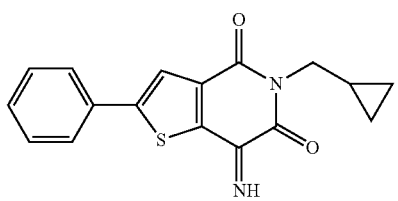 [SMILES: N=C1C(=O)N(CC2CC2)C(=O)c2cc(-c3ccccc3)sc21]

9p 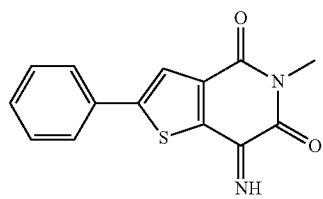 [SMILES: CN1C(=O)C(=N)c2sc(-c3ccccc3)cc2C1=O]

NRT-892-04 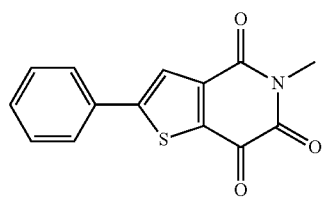 [SMILES: CN1C(=O)C(=O)c2sc(-c3ccccc3)cc2C1=O]

The present disclosure also provides in additional embodiments bis-functional compounds that target the oncogenic protein tyrosine phosphatase PTP4A3. In these compounds a potent ligand of the protein tyrosine phosphatase PTP4A is linked to a moiety that engages the ubiquitin ligase/proteasome system (UPS). Thus, the compounds are those according to Formula (I), or pharmaceutically acceptable salts thereof:

(I)
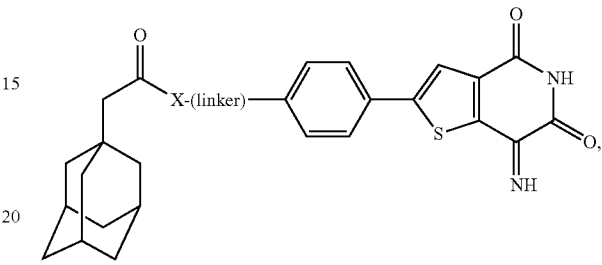

wherein X is O or NH; and (linker) is a linker moiety. In various embodiments, the linker is a $C_1$-$C_{14}$-alkylene group optionally interrupted by one or more of —NH—, —O—, and —C(O)—.

In some embodiments, the moiety —X-(linker)- in Formula (I) is selected from the group consisting of

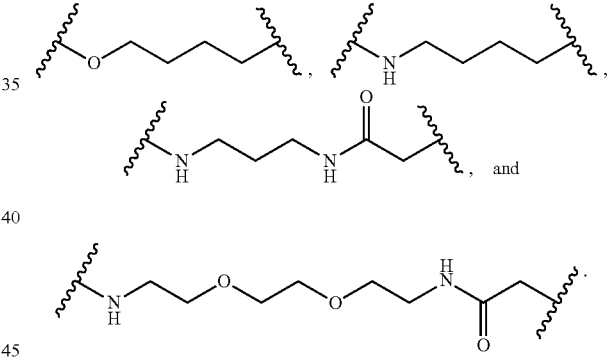

Thus, per some embodiments, a Formula (I) compound or pharmaceutically acceptable salt thereof is selected from the following table:

EJR-876-34 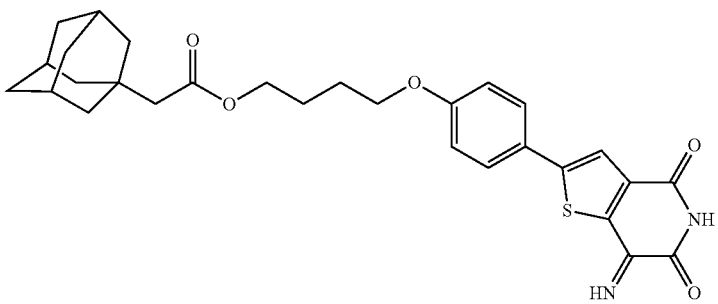

EJR-876-35

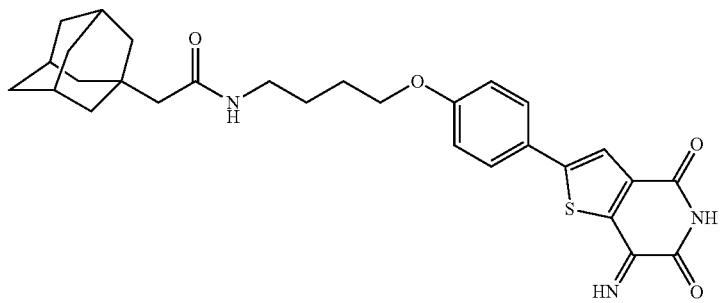

EJR-887-24

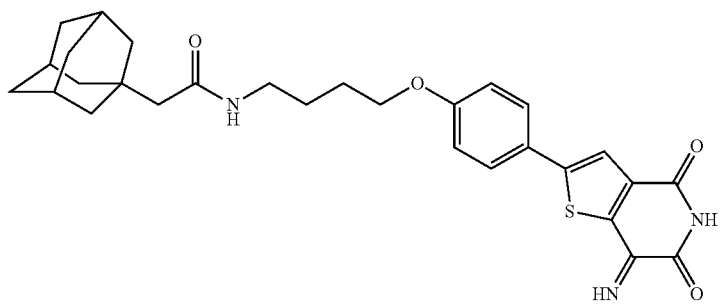

EJR-887-35

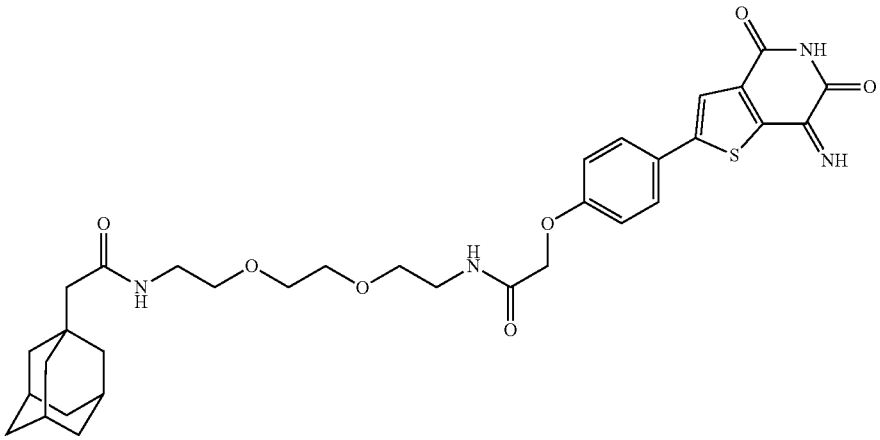 [SMILES: N=C1C(=O)NC(=O)c2cc(-c3ccc(OCC(=O)NCCOCCOCCNC(=O)CC45CC6CC(CC(C6)C4)C5)cc3)sc21]

The present disclosure provides in various embodiments a "pharmaceutically acceptable salt," which is a pharmaceutically acceptable, organic or inorganic acid or base salt of a compound described herein. Where a compound is sufficiently basic or acidic to form acid or base salts, use of the compounds as salts can be appropriate. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

Pharmaceutically acceptable salts can be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutical Composition

The disclosure also provides a pharmaceutical composition comprising a therapeutically effective amount of one or more compounds described herein, or a pharmaceutically acceptable salt thereof in admixture with a pharmaceutically acceptable carrier. In some embodiments, the composition further contains, in accordance with accepted practices of pharmaceutical compounding, one or more additional therapeutic agents, pharmaceutically acceptable excipients, diluents, adjuvants, stabilizers, emulsifiers, preservatives, colorants, buffers, flavor imparting agents.

The pharmaceutical composition of the present disclosure is formulated, dosed, and administered in a fashion consistent with good medical practice. Factors for consideration in this context include the particular disorder being treated, the particular subject being treated, the clinical condition of the subject, the cause of the disorder, the site of delivery of the agent, the method of administration, the scheduling of administration, and other factors known to medical practitioners.

The "therapeutically effective amount" of a compound or a pharmaceutically acceptable salt thereof that is administered is governed by such considerations, and is the minimum amount necessary to exert a cytotoxic effect on a cancer, to inhibit a protein tyrosine phosphatase, to inhibit activity or interaction of a protein tyrosine phosphatase, or combination thereof. Such amount may be below the amount that is toxic to normal cells, or the subject as a whole. Generally, the initial therapeutically effective amount of a compound (or a pharmaceutically acceptable salt, stereoisomer, or tautomer thereof) of the present disclosure that is administered is in the range of about 0.01 to about 200 mg/kg or about 0.1 to about 20 mg/kg of patient body weight per day, with the typical initial range being about 0.3 to about 15 mg/kg/day. Oral unit dosage forms, such as tablets and capsules, may contain from about 0.1 mg to about 1000 mg of a compound (or a pharmaceutically acceptable salt thereof) of the present disclosure. In another embodiment, such dosage forms contain from about 50 mg to about 500 mg of a compound (or a pharmaceutically acceptable salt thereof) of the present disclosure. In yet another embodiment, such dosage forms contain from about 25 mg to about 200 mg of a compound (or a pharmaceutically acceptable salt thereof) of the present disclosure. In still another embodiment, such dosage forms contain from about 10 mg to about 100 mg of a compound (or a pharmaceutically acceptable salt thereof) of the present disclosure. In a further embodiment, such dosage forms contain from about 5 mg to about 50 mg of a compound (or a pharmaceutically acceptable salt thereof) of the present disclosure. In any of the foregoing embodiments the dosage form can be administered once a day or twice per day.

The compositions of the present disclosure can be administered orally, topically, parenterally, by inhalation or spray or rectally in dosage unit formulations. The term parenteral as used herein includes subcutaneous injections, intravenous, intramuscular, intrasternal injection or infusion techniques.

Suitable oral compositions as described herein include without limitation tablets, troches, lozenges, aqueous or oily suspensions, dispersible powders or granules, emulsion, hard or soft capsules, syrups or elixirs.

Another embodiment encompasses pharmaceutical compositions suitable for single unit dosages that comprise a compound of the disclosure or its pharmaceutically acceptable salt and a pharmaceutically acceptable carrier.

The compositions of the present disclosure that are suitable for oral use may be prepared according to any method known to the art for the manufacture of pharmaceutical compositions. For instance, liquid formulations of the compounds of the present disclosure contain one or more agents selected from the group consisting of sweetening agents, flavoring agents, coloring agents and preserving agents in order to provide pharmaceutically palatable preparations of the compound of the present disclosure.

For tablet compositions, a compound of the present disclosure in admixture with non-toxic pharmaceutically acceptable excipients is used for the manufacture of tablets. Examples of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions, a compound of the present disclosure is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending a compound of the present disclosure in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide a compound of the present disclosure in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the present disclosure may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation reaction products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, an aqueous suspension or an oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds described herein may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

Compositions for parenteral administrations are administered in a sterile medium. Depending on the vehicle used and concentration the concentration of the drug in the formulation, the parenteral formulation can either be a suspension or a solution containing dissolved drug. Adjuvants such as local anesthetics, preservatives and buffering agents can also be added to parenteral compositions.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, such as in the range of 6 to 90 mg/kg/day, or in the range of 15 to 60 mg/kg/day. These ranges are not exclusive and include subranges and individual doses and unit doses as well. In one aspect, about 1, 5, 10, 12, 15, 17, 20, 25, 30, 25, 40, 45, 50, 55, 60, 65, 70, 75, 80, 85, 90, 95, or 100 mg/kg is administered. Multiple doses can be used and the timing can vary as to when to administer the drug, as well as the amount per administration. Doses can be administered daily, more than once per day, weekly, more than once per week, monthly, and more than once per month. In one aspect, the first dose is greater than subsequent doses.

The compound is conveniently administered in unit dosage form; for example, containing 5 to 1000 mg, conveniently 10 to 750 mg, most conveniently, 50 to 500 mg of active ingredient per unit dosage form.

Ideally, when the active ingredient needs to enter circulation and be delivered via blood, the active ingredient, in one embodiment, should be administered to achieve peak plasma concentrations of the active compound. This may be achieved, for example, by the intravenous injection of a 0.05 to 5% solution of the active ingredient.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

In another embodiment, a formulation of the present disclosure can be impregnated into a dressing material (or otherwise contained or encompassed by the dressing material). The dressing material is a pharmaceutically acceptable fabric. It can be, for example, gauze or any other type of medical fabric or material that can be used to cover a wound and/or to keep a therapeutic agent or composition in contact with a patient.

The composition of the present disclosure can further comprise additional therapeutic additives, alone or in combination (e.g., 2, 3, or 4 additional additives). Examples of additional additives include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; and (e) combinations thereof.

Methods of Use

The compounds and their pharmaceutically acceptable salts described herein inhibit the function of PTP4A protein tyrosine phosphatases, especially the oncogenic protein tyrosine phosphatase PTP4A3. The compounds can be used to induce rapid intracellular degradation of PTP4A3 that is useful for the treatment of many forms of human cancers.

In an embodiment, the present disclosure provides a method for treating a subject suffering from cancer. The method comprises administering to the subject a therapeutically effective amount of a compound according to claim 1 or a pharmaceutically acceptable salt thereof. Administration is achieved, in various embodiments, by any of the routes described above, and optionally by use of any of the pharmaceutical compositions herein described.

Cancers that are particularly vulnerable to PTP4A3 degradation, per various embodiments, include ovarian cancer and any advanced ovarian cancer; breast cancer, such as triple negative breast cancer; colorectal cancer; bladder cancer; brain cancer; cervical cancer; lung cancer; liver cancer; stomach cancer; stromal cancer; leukemias; and lymphomas. Exemplary embodiments include treatment of triple negative breast cancer or advanced ovarian cancer.

The present disclosure is now described with reference to the following Examples and Embodiments. Without further description, it is believed that one of ordinary skill in the art can, using the preceding description and the following illustrative examples, make and utilize the present disclosure and practice the claimed methods. The following working examples therefore, are provided for the purpose of illustration only and specifically point out the certain embodiments of the present disclosure, and are not to be construed as limiting in any way the remainder of the disclosure. Therefore, the examples should be construed to encompass any and all variations that become evident as a result of the teaching provided herein.

Examples

Introduction

Photooxygenations are considered as green alternatives to standard oxidation methods, as the former involve light and generally environmentally innocuous reagents.[1,2] Transition metal-free conditions with stoichiometric molecular oxygen or air as reactants can eliminate the need for toxic or expensive catalysts. Photosensitizers such as Rose Bengal, methylene blue, and tetraphenylporphyrin have been used in several natural product syntheses to generate singlet oxygen, which reacts with electron-rich alkenes and aromatic rings.[1,2] For example, a photosensitized singlet oxygen transformation was implemented in the formal synthesis of daphnane diterpene ortho esters and several alkaloids.[2,3] While photooxygenation is an atom-economical alternative to commonly used reagents and metal-based oxidation protocols, regioselectivity is often difficult to control, especially with alkenes,[1] and sometimes requires complex reactors,[4] photosensitizers,[5-7] photocatalysts,[8] or other additives.[1,8]

The synthesis of N-unsubstituted imines remains a challenging problem due to their propensity to hydrolyze under ambient conditions.[9-11] Therefore, N—H imines are under-represented in the literature and are frequently only used as transient intermediates.[12] An exception are natural products such as caulibugulone E, where the imine is stabilized by conjugation to an arene and an electron-rich enamine.[13] Caulibugulone E has distinct biological properties and the N—H imine can be prepared by treatment of the corresponding carbonyl compound, caulibugulone A, with ammonia in the presence of Ti(O-i-Pr)$_4$.[14] Oxygenation of aryl amines represents another access point to N-unsubstituted imines, but often results in hydrolysis under the reaction conditions, or a mechanistically complex displacement of the amine with dioxygen.[1] Examples in the literature where the imine is preserved are scarce and low yielding.[15,16] Fremy's salt is one of many methods to mimic singlet oxygen,[17] but it is unselective for imine formation and results in hydrolysis.[18]

The photooxygenation of thienopyridone 1 can be performed in high yield, but on limited scale (<50 mg), to produce a novel nanomolar PTP4A3 phosphatase inhibitor,[19] 7-iminothieno[3,2-c]pyridine-4,6(5H,7H)-dione 2[20], as shown in Scheme 1:

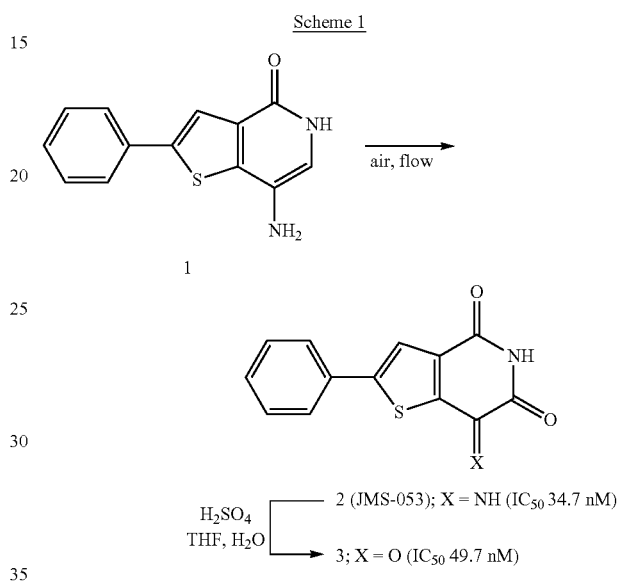

For the further investigation of the intriguing biological profile of 2,[21] particularly through in vivo studies, synthetic access to gram-quantities of this material became an important requirement. Due to the very sluggish reaction progress in the batch setup, which was aggravated by the poor solubility of both substrate and product, a flow process starting with a diluted, homogeneous solution of the reactant was developed. Photochemical flow processes allow for a significant decrease in reaction time by increasing the exposure of the reaction mixture to light while removing light-capturing products and precipitates.[22]

In the original synthesis of 2,[20] a minor by-product was observed in the batch photooxygenation process, and the identity of this compound was elusive for some time. Some reports have suggested that these type of transformations result in dimers;[23] alternatively, the corresponding carbonyl compound is also known to be the major product in related conversions, either formed directly or through hydrolysis.[18,23a]

When the reaction mixture was treated with aqueous sulfuric acid, we were able to isolate the by-product as the sole product. Furthermore, an x-ray structure confirmed its assignment as tricarbonyl compound 3 (Scheme 1). Photooxygenation of 1 in a methanol/water mixture at neutral pH still greatly favored imine formation; therefore, the formation of tricarbonyl compound 3 in the reaction mixture is unlikely to proceed substantially through the hydrolysis of 2. While there is only a single previous report on a compound containing the thienopyridinetrione scaffold of 3,[24] structurally related pyridine-, pyrrolopyridine-, and isoquinolinetriones have been obtained by oxidations of pyridines, pyrrolopyridines, and isoquinolines, respectively, as well as via the Beckmann rearrangement or the azido-Schmidt reaction of ninhydrin.[23b,c,25,26] Some of these compounds are of pharmaceutical interest as hepatitis C NS3 proteinase and caspase inhibitors.[23c,26]

General Methods

Unless stated otherwise, all reactions were performed under an atmosphere of $N_2$ that was passed through a column (10×2 cm) of Drierite®. Air was used for all in-flow photooxygenation reactions, whereas the batch reactions photooyxygenations and the nitration with t-BuONO used oxygen in a balloon from an $O_2$ tank. Prior to use, THF was freshly distilled over sodium/benzophenone, and $CH_2Cl_2$ was freshly distilled over $CaH_2$. $Et_3N$ and i-$PrNEt_2$ were distilled over $CaH_2$ and stored over KOH. All glassware and stir bars were dried in an oven for 3 h prior to use. When necessary, degassed solvents were prepared by sparging with $N_2$ for 1 h. Reactions were monitored by TLC analysis (pre-coated silica gel 60 $F_{254}$) and spots were visualized (UV lamp 254 nm and 395 nm). Purifications by chromatography were performed on $SiO_2$. $^1H/^{13}C$ NMR spectra were recorded on Bruker Avance 300/75 MHz, Bruker Avance 400/100 MHz or Bruker Avance 500/125 MHz instruments. High resolution mass spectra were obtained on a Micromass UK Limited, Q-TOF Ultima API or a Thermo Scientific Exactive Orbitrap LC-MS. Chemical shifts were reported in parts per million (ppm) with the residual solvent peak ($CDCl_3$: 7.26 ppm for $^1H$, 77.16 ppm for $^{13}C$; DMSO-$d_6$: 2.50 ppm for $^1H$, 39.52 ppm for $^{13}C$) used as the internal standard. Chemical shifts were tabulated as follows: chemical shift, multiplicity (s=singlet, d=doublet, t=triplet, q=quartet, dd=doublet of doublet, dt=doublet of triplet, ddd=doublet of doublet of doublet, m=multiplet, brs=broad singlet), coupling constant(s), and integration. IR spectra were obtained using neat samples on a Perkin-Elmer 100 IR-ATR spectrometer. Melting points were obtained using a Mel-Temp instrument and are uncorrected. A variable peristaltic pump (VWR Model PP3300) was used for the photooxygenation reactions. 30 cm of silicone tubing (1/16" ID, 3/16" OD, 1/16" wall thickness) in the pump were connected to 10.5 m of clear FEB tubing (4 mm ID, 5 mm OD, 0.5 mm wall thickness) via an adapter. The light source was a white household 18 W CFL or a 40 W-4U BestCircle (AC85-265V) LED for the scale-up reactions. For the white CFL and white LED lights, the external temperature of the capillary tubing did not exceed 42° C.

General Procedure A: Photo-Flow Oxygenation of Thienopyridones.

7-Iminothieno[3,2-c]pyridine-4,6(5H,7H)-dione (2) and 2-phenylthieno[3,2-c]pyridine-4,6,7(5H)-trione (3). The photo-flow reactor was flushed with MeOH (50 mL). Once the solvent front entered the receiving flask, a solution of 7-amino-2-phenylthieno[3,2-c]pyridin-4(5H)-one (1, 10 mg)[20] in MeOH (30 mL) was passed through the tubing at a rate of 1.9 mL/min using the peristaltic pump (5 rpm). Subsequently, the tubing was flushed with additional MeOH (40 mL). The reaction mixture was concentrated to give a mixture of 2 and 3 (10 mg) and purified by chromatography on $SiO_2$ (EtOAc:hexanes, 7:3, followed by MeOH:EtOAc, 1:9) to give 2 (9.1 mg, 91%): $^1H$ NMR (300 MHz, DMSO-$d_6$) δ 11.86 (s, 1H), 11.59 (s, 1H), 7.98 (s, 1H), 7.87 (dd, J=8.1, 1.5 Hz, 2H), 7.53-7.45 (m, 3H). Spectral data were consistent with literature properties.[20]

2-Phenylthieno[3,2-c]pyridine-4,6,7(5H)-trione (3). To a solution of a mixture of 2 and 3 (6:1 ratio by $^1H$ NMR analysis, 0.040 g, 0.16 mmol), prepared according to General Protocol A in THF:$H_2O$ (1:1, 10 mL) was added $H_2SO_4$ (0.083 mL, 1.6 mmol). The reaction mixture was allowed to stir at room temperature for 24 h, cooled in an ice bath and filtered. The precipitate was washed with ice-cold $H_2O$ and dissolved in THF. The THF solution was concentrated and dried under high vacuum at 45° C. overnight to afford a brown solid that was purified by chromatography on $SiO_2$ (EtOAc:hexanes, 7:3, followed by MeOH:EtOAc, 1:9) to give 3 (0.031 g, 0.120 mmol, 77%) as a bright yellow solid: Mp>250° C.; IR (ATR) $v_{max}$ 3195, 3093, 2921, 2849, 1726, 1700, 1667, 1450, 1417, 1333, 1272 $cm^{-1}$; $^1H$ NMR (500 MHz, DMSO-$d_6$) δ 11.91 (brs, 1H), 8.09 (d, J=3.5 Hz, 1H), 7.94 (dd, J=8, 2 Hz, 2H), 7.54-7.50 (m, 3H); $^{13}C$ NMR (75 MHz, DMSO-$d_6$) δ 168.7, 159.6, 158.0, 154.4, 141.0, 139.7, 131.5, 130.4, 129.5, 126.5, 123.1; HRMS (ESI$^+$) m/z calcd for $C_{13}H_8O_3NS$ (M+H) 258.0219, found 258.0219.

Thienopyridone 1 was used to optimize the photooxygenation conditions leading to 2 in a photo-flow setup as summarized in Table 1. Solvent, light source, flow rate, and additives were varied to minimize the formation of 3.

TABLE 1

Flow photooxygenation of 1 to 2.[a]

| Entry | Solvent | Light Source | Ratio of 2 to 3[b] |
|---|---|---|---|
| 1 | 1,2-DCE[c] | CFL | 0:1 |
| 2 | 1,2-DCE[d] | CFL | 1.5:1 |
| 3 | CHCl$_3$[d] | CFL | 0:1 |
| 4 | MeOH[d] | CFL | 8.7:1 |
| 5 | MeOH | CFL | 10:1 |
| 6 | i-PrOH | CFL | 7.5:1 |
| 7 | HFIP | CFL | 6:1 |
| 8 | THF | CFL | 6.3:1 |
| 9 | MeOH | Red (IR) Lamp | rsm[e] |
| 10f | i-PrOH | Red (IR) Lamp | 6.7:1 |
| 11 | MeOH[g] | CFL | 10:1 |

[a]Optimizations were performed on a 10-mg scale with 30 mL of solvent (at a concentration of 1.4 mM), utilizing an 18 W compact fluorescent lamp (CFL) with a flow rate of 1.9 mL/min. The tubing volume was 80 mL.
[b]Ratios were determined by 1H NMR integration.
[c]Flow rate = 0.1 mL/min.
[d]Flow rate = 0.8 mL/min.
[e]Recovered starting material.
[f]Three mol % methylene blue added.
[g]Distilled over Mg turnings and stored over 3 Å molecular sieves for 5 days.

Additives generally increased the content of 3 or decreased the rate of conversion of 1, and photosensitizers were not effective. As expected, conversion was not affected by the concentration of the starting material, but the low solubilities of 1 and 2 required moderate to high dilution. In MeOH, the UV-absorption band of the 353 nm peak of thienopyridone 1 extended to 500 nm into the visible range of the spectrum. The corresponding absorption maximum of imine 2 was 379 nm, and this peak extended to 450 nm. Both amine 1 and imine 2 exhibited a strong green fluorescence. Combined, these data suggest that these substrates act as their own photosensitizers. Experiments with Rose Bengal and Methylene Blue were explored in an attempt enhance the reactivity of 1 and the ratio of 2 to 3, but no substantial changes were observed when a white CFL or white LED lights were used with these photosensitizers.

Chlorinated solvents such as 1,2-dichloroethane (DCE) and CHCl$_3$ exhibited a strong preference for the formation of 3 (Table 1, entries 1-3). MeOH showed selectivity for the formation of 2, and the ratio of 2 to 3 increased when the flow rate was accelerated (entries 4-5). The use of dry methanol did not appreciably affect the outcome (entry 11). Photooxygenation in hexafluoroisopropanol (HFIP) resulted in a complex mixture of products. Other protic and polar aprotic solvents, such as i-PrOH and THF, respectively, resulted in diminished selectivity (entries 6 and 8). Imine formation was favored in solvents with short singlet oxygen lifetimes.[27] Additionally, faster flow rates often provided an increase in imine formation; although, flow rates above 1.9 mL/min led to decreased conversion.

Optimized conditions required MeOH as the solvent, a household 18 W CFL light bulb as the light source, and a flow rate of 1.9 mL/min, resulting in a substrate residence time in the flow reactor of 42 min, which is a significant improvement over the previous multi-day batch process. With these conditions, the desired imine 2 was obtained in a 10:1 ratio over ketone 3. It was also found that white LED lights worked just as effectively as the CFL. No additional air or oxygen was bubbled through the system; the mole fraction of O$_2$ in MeOH from exposure to ambient air was sufficient to keep the concentration of O$_2$ in the open flow system at any time at least 2 times higher than the concentration of the substrate (1.4 mM). Conversely, when the photo-flow reaction was performed under otherwise optimized conditions but under an atmosphere of argon instead of air, only 17% conversion was observed by $^1$H NMR.

General Synthesis of Compounds 8

In order to examine the substrate scope of the reaction, a general synthetic route allowing for late-stage diversification of the thienopyridone scaffold was accomplished in 5 steps from commercially available aldehyde 4 (Scheme 2).

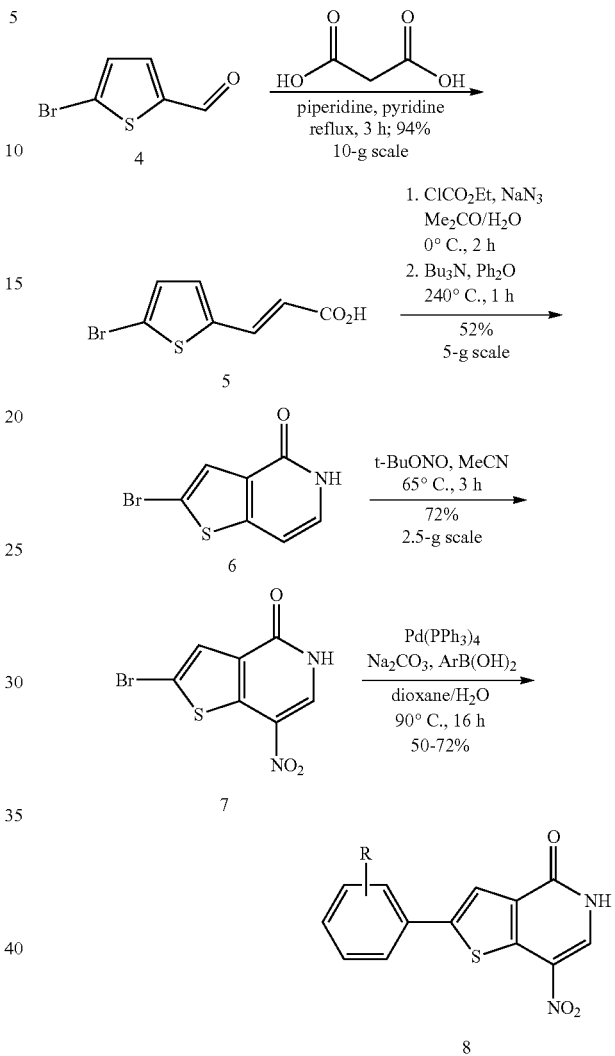

Scheme 2. Synthesis of thienopyridone scaffold enabling late-stage diversification with aryl boronic acids.

A Knoevenagel condensation using malonic acid afforded 5 in 94% yield. Acyl azide formation, Curtius rearrangement, and concomitant cyclization provided the thienopyridone scaffold 6 in 52% yield over 2 steps. Nitration attempts using nitric acid resulted in poor mass recovery; therefore, nitration was performed with tert-butyl nitrite to give the nitrated product 7 in 72% yield.[28] A late stage Suzuki-Miyaura coupling with aryl boronic acids allowed for facile substrate diversifications to give 8a-p.

Isolation of the enamine after reduction of the nitro group in 8 proved difficult due to the formation of trace photooxygenation products during the purification step. Therefore, a 2-step procedure was implemented to examine the substrate scope (Scheme 3). By $^1$H NMR analysis in the presence of an internal standard (1,3,5-trimethoxybenzene), 8c and 8e were reduced to the corresponding amine intermediates in 80% and 67% yield, respectively.

Scheme 3. Conversion of nitropyridones 8a-p to 7-iminothieno [3,2-c]pyridine-4,6(5H,7H)-diones 9a-q and attempted conversion of 8p to acetimide 10
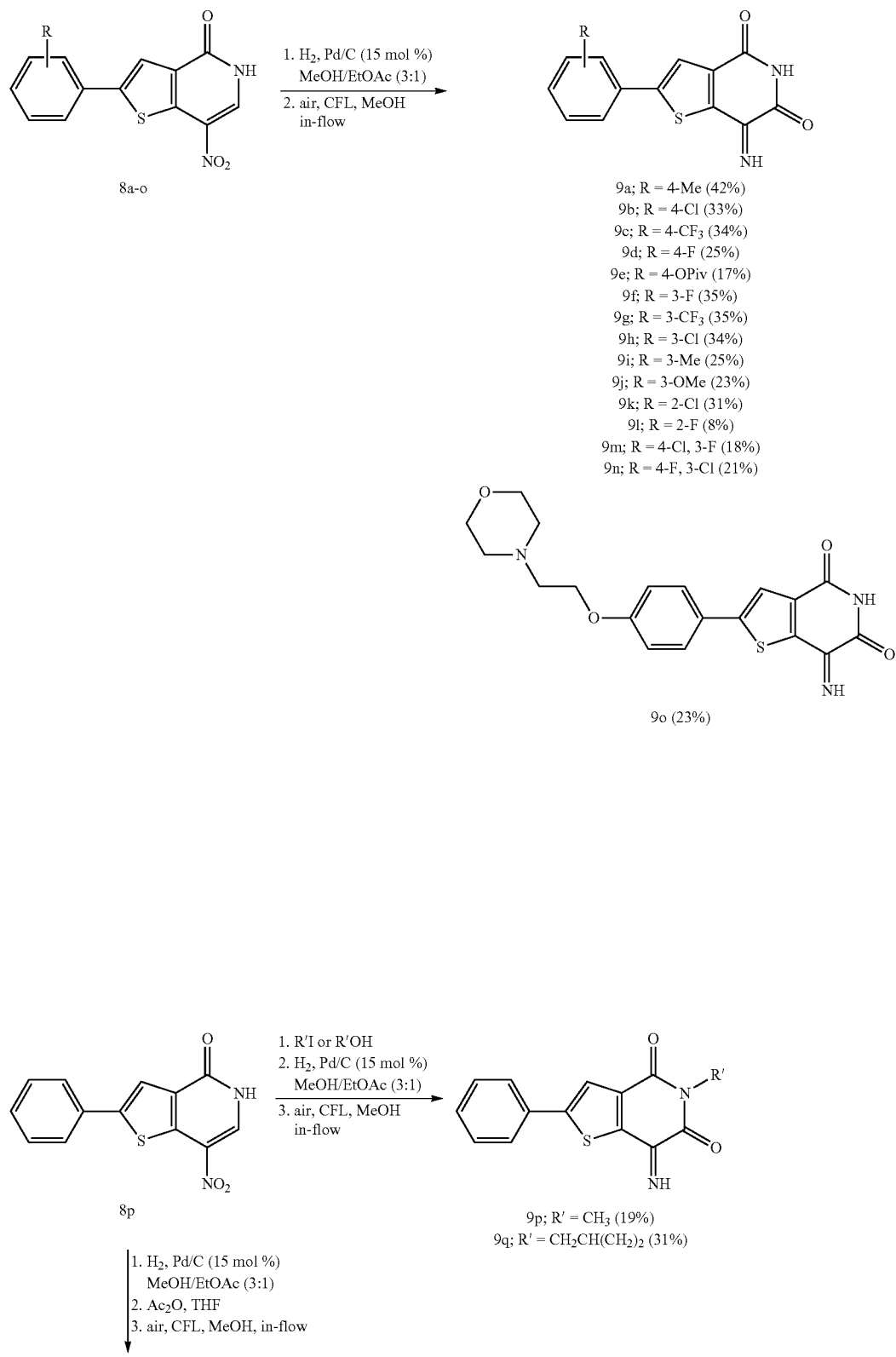

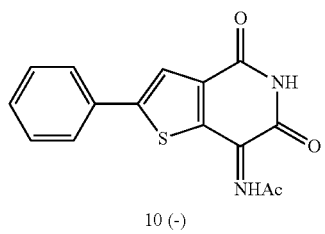

10 (-)

Excellent functional group tolerance was observed, as electron-rich and -deficient arenes, halides, and amines did not impede reactivity. Additionally, the photooxygenation of N-alkylated amides, obtained from 8p[20] by alkylation with R'I in the presence of $K_2CO_3$ or under Mitsunobu reaction conditions with R'OH, produced N-methyl 9p and N-methylcyclopropyl 9q in 19% and 31% yield, respectively, over 3 steps. In contrast, N-acylation of enamine 1 obtained after reduction of the nitro group in 8p rendered the substrate unreactive to photooxygenation, likely due to the decreased electron density at the α-carbon, and compound 10 was not observed.

The lower yields in the telescoped conversion of nitroalkenes 8 to α-ketoimines 9 vs the two-step process can be attributed to product loss in the separation of the imines from minor ketone side products during chromatography on $SiO_2$. Imine 9l was exceptionally difficult to purify, resulting in a poor yield of 8%. Therefore, for scale-up purposes, it became necessary to develop a method to isolate the imine product from the ketone without chromatography. Recrystallization to enrich the imines was not successful. Amines can form adducts with $BF_3 \cdot OEt_2$,[29] but attempts to generate an imine-boron complex proved similarly unsuccessful. An aza-Wittig reaction utilizing P,P,P-triphenylphosphazene,[30] or the $Ti(O-i-Pr)_4/NH_3$ protocol[14a] to convert the imine (2)/ketone (3) mixture exclusively to the imine also failed. In situ reaction with hexamethyldisilazene (HMDS) and CsF in DMF, or TBAF in THF,[31] provided the imine 2 in >95% selectivity over ketone 3; however, chromatography was still needed to remove other trace impurities.

Treatment of a mixture of 2 and 3 with $NH_4OAc$ in MeOH at 65° C. resulted in quantitative formation of the imine. A homogenous solution was necessary to obtain full convergence to the imine. When the reaction was performed at reflux, decomposition was observed, likely due to evaporation of ammonia; therefore, a sealed reaction vessel was required. Interestingly, $NH_4Cl$ did not react with the ketone, and $NH_4OH$ and methanolic $NH_3$ caused decomposition.

With a modified purification protocol for the final products 9 established, the scalability of the photooxygenation was investigated next. The synthesis of 8p was performed via an alternative route than previously reported,[20] with the goal being to facilitate compound throughput (Scheme 4). Commercially available thiophene 11 was treated with triphosgene to give the isocyanate, which was subjected without purification to stoichiometric ferric chloride in $CH_2Cl_2$ to give lactam 12 in 73% yield over the two steps. C-2 bromination of 12 in acetic acid and Suzuki-Miyaura coupling with phenylboronic acid proceeded in 64% overall yield to give 13. The coupling product was dehydrogenated with DDQ and nitrated with tert-butyl nitrite to generate 8p. The two-step nitro group reduction-photooxygenation was performed on a 500-mg and a 1-g scale, and the combined yields of 2 and 3 in these batches were 68% and 67%, respectively. Subsequently, imination of these reaction mixtures using $NH_4OAc$ resulted in quantitative conversions, providing 322 mg and 634 mg, respectively, of iminothienopyridone 2 (Scheme 4).

Scheme 4. Scale-up of optimized in-flow photooxygenation and telescoped conversion of 8p to give 2.

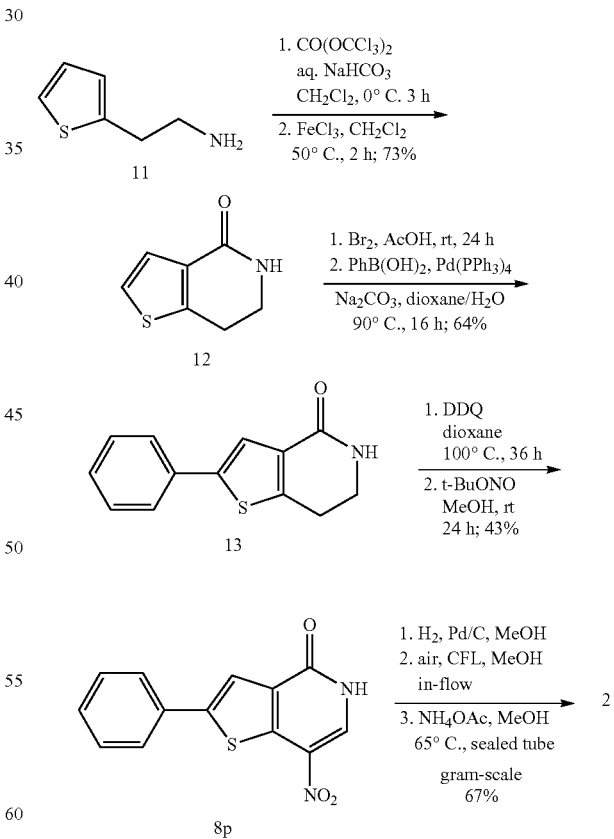

We also investigated the photooxygenation of other fused pyridones (Scheme 5). Unlike the thienopyridones, these substrates were not fluorescent and required photosensitizers such as methylene blue to react with dioxygen.

Scheme 5. Photooxygenation of alternative heterocyclic scaffolds.

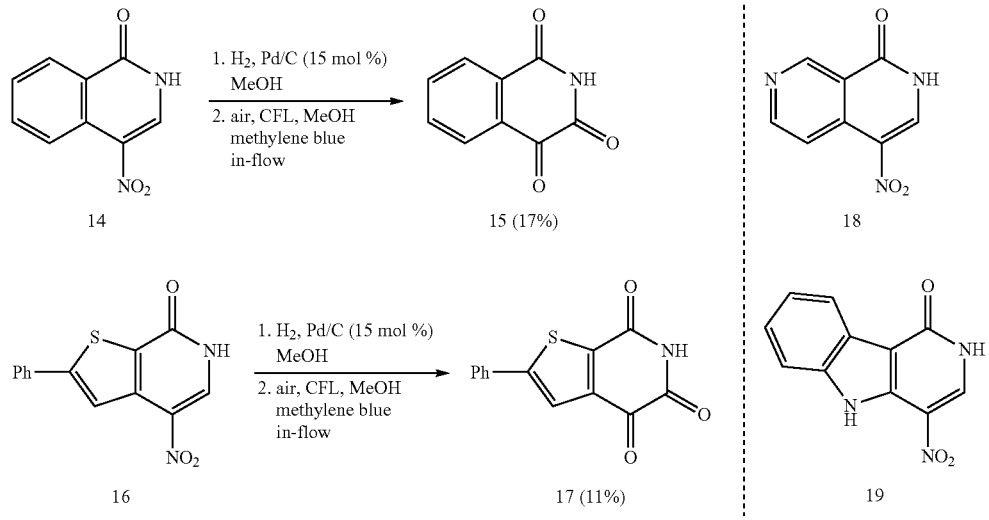

4-Nitroisoquinoline 14 provided tricarbonyl product 15 in 17% yield, but attempts to generate the imine were unsuccessful, in agreement with previous reports.[23a] Interestingly, thieno[2,3-c]pyridin-7(6H)-one 16 behaved very differently compared to the regioisomeric thieno[3,2-c]pyridin-4(5H)-one 8, despite their close structural similarity. Unlike 2, the amine derived from 16 fluoresced with a pale-orange colour under a UV light, and was less reactive, as it required a photosensitizer for further conversion. The reaction profile was not clean, and the only product that could be isolated was tricarbonyl compound 17. Isoquinolin-1(2H)-one 18 was unreactive in the photooxygenation after nitro group reduction, likely due to deactivation of the pyridone by the fused, electron-withdrawing pyridine ring, and only starting material was recovered. In contrast, when the very electron-rich enamine derived from the nitro group reduction of azacarbazole 19 was subjected to photooxygenation, only decomposition products were observed.

The value of the photooxygenation of aminothienopyridinones is significantly enhanced by the utility of these scaffolds. Thienopyridones and their analogs are privileged structural motifs for the development of biologically active molecules.[33,34] While direct functionalizations on this heterocyclic core are rare, the biological properties of the chemotype can be significantly improved by such modifications.[35] Thienopyridone 1 was reported to be a selective phosphatase inhibitor and to suppress tumor cell growth.[36] Our original entry into photooxygenation[20] was inspired by the desire to diversify this scaffold by the introduction of additional carbonyl, amine, and imine substituents.

Compound Syntheses and Characterization (E)-3-(5-Bromothiophen-2-yl)acrylic acid (5). To a solution of 5-bromothiophene-2-carboxaldehyde (4) (10.15 g, 51.53 mmol) in pyridine (128 mL) were added malonic acid (16.25 g, 154.6 mmol) and piperidine (2.57 mL, 25.76 mmol). The reaction mixture was heated at reflux for 3 h, cooled to room temperature and concentrated to give a dark oil. The oil was diluted with $H_2O$ (30 mL), at which time a solid precipitated. The suspension was then acidified to pH 2 with 6 M HCl. The precipitate was filtered and washed with $H_2O$ (3×15 mL). The filter cake was dissolved in EtOAc, dried ($MgSO_4$), filtered, and concentrated to give 5 (11.29 g, 94%) as a tan solid: $^1$H NMR (300 MHz, DMSO-$d_6$) δ 12.41 (brs, 1H), 7.66 (d, J=15.9 Hz, 1H), 7.35 (d, J=3.9 Hz, 1H), 7.27 (d, J=3.9 Hz, 1H), 6.15 (d, J=15.9 Hz, 1H). Spectral data are consistent with literature properties.[37]

2-Bromothieno[3,2-c]pyridin-4(5H)-one (6). $Et_3N$ (6.02 mL, 42.9 mmol) was added to a solution of (E)-3-(5-bromothiophen-2-yl)acrylic acid (5, 5.00 g, 21.4 mmol) in acetone (55 mL) at 0° C. (ice-bath). Ethyl chloroformate (6.25 mL, 64.3 mmol) was then added, and the reaction mixture was stirred at 0° C. for 1.5 h. A solution of $NaN_3$ (2.09 g, 32.1 mmol) in $H_2O$ (16 mL) was added to this reaction mixture slowly at 0° C. (ice-bath). The mixture became homogeneous, and then a solid began to precipitate. Stirring was continued for 15 min. The reaction mixture was poured into ice-chilled $H_2O$ (30 mL) and extracted with EtOAc (3×30 mL). The combined organic layers were dried ($MgSO_4$), filtered and concentrated to give crude acyl azide as a tan solid that was used for the next step without further purification.

A 3-neck flask fitted with a stopper, addition funnel, and condenser was charged with $Bu_3N$ (6.63 mL, 27.8 mmol) and $Ph_2O$ (20 mL). The solution was heated to 240° C. The addition funnel was charged with a solution of the crude acyl azide (5.53 g, 21.4 mmol) in $CH_2Cl_2$ (50 mL). The acyl azide solution was added to the hot reaction mixture over a period of ca. 40 min, allowing the $CH_2Cl_2$ to boil off. The mixture was stirred at 240° C. for another 15 min, cooled to rt, and hexanes (20 mL) was added, at which point a solid began to precipitate. The hexane layer was decanted, and the remaining residue was suspended in EtOAc (15 mL). A tan solid precipitated out of solution and was filtered to give 6 (2.56 g, 52%): Mp>250° C.; IR (ATR) $v_{max}$ 2809, 1637, 1607, 1513, 1472, 1274, 1222, 1144, 994, 928, 803, 762, 692 $cm^{-1}$; $^1$H NMR (400 MHz, DMSO-$d_6$) δ 11.54 (brs, 1H), 7.54 (d, J=0.4 Hz, 1H), 7.28-7.25 (m, 1H), 6.81 (d, J=6.8 Hz, 1H); $^{13}$C NMR (100 MHz, DMSO-$d_6$) δ 157.5, 149.7, 130.7, 130.4, 126.8, 111.4, 100.5; HRMS (ESI$^+$) m/z calcd for $C_7H_5ONSBr$ (M+H) 229.9270, found 229.9270.

2-Bromo-7-nitrothieno[3,2-c]pyridin-4(5H)-one (7). A solution of 2-bromothieno[3,2-c]pyridin-4(5H)-one (6, 2.56 g, 11.1 mmol) in MeCN (275 mL) was heated to 65° C. in a 500 mL round-bottom flask fitted with a condenser under an O$_2$ atmosphere (balloon, 1 atm). After addition of t-BuONO (5.88 mL, 44.5 mmol), the reaction mixture was stirred for 3 h and turned from a brown heterogeneous mixture to a red homogeneous solution. The solution was cooled to room temperature and concentrated. The resulting yellow solid was suspended in MeCN (10 mL) and placed in a −20° C. freezer for 30 min. The precipitate was filtered to provide 7 as a yellow solid (2.21 g, 72%): Mp>250° C.; IR (ATR) $v_{max}$ 2807, 1648, 1617, 1508, 1480, 1336, 1243, 1127, 1038, 890, 764, 706 cm$^{-1}$; $^1$H NMR (400 MHz, DMSO-d$_6$) δ 12.86 (brs, 1H), 8.75 (s, 1H), 7.71 (s, 1H); $^{13}$C NMR (100 MHz, DMSO-d$_6$) δ 156.9, 140.6, 135.9, 128.9, 126.9, 126.8, 115.9; HRMS (ESI$^+$) m/z calcd for C$_7$H$_4$O$_3$N$_2$SBr (M+H) 274.9119, found 274.9121.

General procedure B: Suzuki coupling of 2-bromo-7-nitrothieno[3,2-c]pyridin-4(5H)-one (7). A 25-mL round-bottom flask was charged inside a glove box with Pd(PPh$_3$)$_4$ (5.0 mol %). The flask was removed from the glove box and sequentially charged with 2-bromo-7-nitrothieno[3,2-c]pyridin-4(5H)-one (7, 1.0 equiv), aryl boronic acid (1.1 equiv), and Na$_2$CO$_3$ (2.3 equiv). The flask was then purged under a stream of N$_2$, diluted with deoxygenated dioxane and H$_2$O (2:1, 0.1 M), fitted with a reflux condenser, and heated to 90° C. for 16 h. The reaction mixture was cooled to room temperature to give a red oil that was diluted with H$_2$O (10 mL) and treated with 1 M KHSO$_4$ (5 mL). The red oil changed to an orange semi-solid suspension, and the mixture was diluted with EtOAc (40 mL). The layers were separated and the aqueous phase was extracted with EtOAc (4×20 mL). The combined organic extracts were washed with saturated aqueous NaCl, dried (MgSO$_4$), filtered, and concentrated to give an orange solid that was suspended in MeOH (2 mL), sonicated, and heated to the boiling point. The suspension was cooled to room temperature, filtered, and the solids were washed with ice-cold MeOH (1 mL) to give the coupling product. If residual Ph$_3$P(O) was present, the MeOH trituration protocol was repeated.

2-(3-Fluorophenyl)-7-nitrothieno[3,2-c]pyridin-4(5H)-one (8f). 2-Bromo-7-nitrothieno[3,2-c]pyridin-4(5H)-one (7, 0.075 g, 0.272 mmol) was converted according to general procedure B to give 8f (0.040 g, 50%) as a yellow solid: Mp>250° C.; IR (ATR) $v_{max}$ 2798, 1653, 1611, 1502, 1476, 1340, 1263, 1241, 840, 765, 711, 673 cm$^{-1}$; $^1$H NMR (400 MHz, DMSO-d$_6$) δ 12.79 (brs, 1H), 8.76 (s, 1H), 8.09 (s, 1H), 7.77 (d, J=10.4 Hz, 1H), 6.67 (d, J=8.0 Hz, 1H), 7.51 (q, J=6.4 Hz, 1H), 7.26-7.21 (m, 1H); $^{13}$C NMR (125 MHz, DMSO-d$_6$) δ 162.5 (d, J$_{C-F}$=243.7 Hz), 157.8, 143.0, 138.8, 135.6, 134.4 (d, J$_{C-F}$=8.7 Hz), 131.2 (d, J$_{C-F}$=8.7 Hz), 129.7, 127.1, 122.1 (d, J$_{C-F}$=2.5 Hz), 122.1, 115.4 (d, J$_{C-F}$=21.2 Hz), 112.6 (d, J$_{C-F}$=22.5 Hz); $^{19}$F NMR (470 MHz, DMSO-d$_6$) δ −111.9; HRMS (ESI$^+$) m/z calcd for C$_{13}$H$_8$O$_3$N$_2$FS (M+H) 291.0234, found 291.0232.

2-(3-Chlorophenyl)-7-nitrothieno[3,2-c]pyridin-4(5H)-one (8h). 2-Bromo-7-nitrothieno[3,2-c]pyridin-4(5H)-one (7, 0.200 g, 0.727 mmol) was converted according to general procedure B to give 8h (0.161 g, 72%) as a yellow solid: Mp>250° C.; IR (ATR) $v_{max}$ 2790, 2683, 1654, 1614, 1593, 1499, 1475, 1335, 1247, 1232, 1140, 1041, 994, 763, 71 cm$^{-1}$; $^1$H NMR (500 MHz, DMSO-d$_6$) δ 12.77 (brs, 1H), 8.76 (s, 1H), 8.10 (s, 1H), 7.96 (s, 1H), 7.80 (d, J=6.0 Hz, 1H), 7.52-7.45 (m, 2H); $^{13}$C NMR (125 MHz, DMSO-d$_6$) δ 157.8, 142.7, 138.8, 135.7, 134.3, 134.1, 131.0, 129.7, 128.5, 127.1, 125.5, 124.6, 121.2; HRMS (ESI$^+$) m/z calcd for C$_{13}$H$_8$O$_3$N$_2$ClS (M+H) 306.9939, found 306.9937.

7-Nitro-2-(m-tolyl)thieno[3,2-c]pyridin-4(5H)-one (8i). 2-Bromo-7-nitrothieno[3,2-c]pyridin-4(5H)-one (7, 0.150 g, 0.545 mmol) was converted according to general procedure B to give 8i (0.092 g, 59%) as a yellow solid: Mp>250° C.; IR (ATR) $v_{max}$ 2807, 1648, 1619, 1598, 1502, 1476, 1336, 1236, 1135, 1040, 801, 766, 712 cm$^{-1}$; $^1$H NMR (500 MHz, DMSO-d$_6$) δ 12.72 (brs, 1H), 8.72 (s, 1H), 7.94 (s, 1H), 7.67 (s, 1H), 7.63 (d, J=6.4 Hz, 1H), 7.36 (t, J=6.4 Hz, 1H), 7.22 (d, J=6.0 Hz, 1H), 2.38 (s, 3H); $^{13}$C NMR (125 MHz, DMSO-d$_6$): δ 157.8, 144.8, 138.7, 138.2, 135.2, 132.1, 129.8, 129.5, 129.1, 127.2, 126.4, 123.0, 119.6, 20.8; HRMS (ESI$^+$) m/z calcd for C$_{14}$H$_{11}$O$_3$N$_2$S (M+H) 287.0485, found 287.0483.

2-(2-Chlorophenyl)-7-nitrothieno[3,2-c]pyridin-4(5H)-one (8k). 2-Bromo-7-nitrothieno[3,2-c]pyridin-4(5H)-one (7, 0.200 g, 0.727 mmol) was converted according to general procedure B to give 8k (0.122 g, 55%) as a yellow solid: Mp>250° C.; IR (ATR) $v_{max}$ 2852, 1654, 1611, 1500, 1467, 1335, 1242, 1038, 872, 822, 747, 707 cm$^{-1}$; $^1$H NMR (300 MHz, DMSO-d$_6$) δ 12.82 (brs, 1H), 8.79 (s, 1H), 7.84 (s, 1H), 7.79-7.75 (m, 1H), 7.67-7.64 (m, 1H), 7.49-7.46 (m, 2H); $^{13}$C NMR (75 MHz, DMSO-d$_6$) δ 158.2, 140.7, 139.6, 136.1, 131.7, 131.1, 130.9, 130.6, 130.4, 128.6, 128.0, 127.1, 124.4; HRMS (ESI$^+$) m/z calcd for C$_{13}$H$_8$O$_3$N$_2$SCl (M+H) 306.9939, found 306.9938.

2-(2-Fluorophenyl)-7-nitrothieno[3,2-c]pyridin-4(5H)-one (8l). 2-Bromo-7-nitrothieno[3,2-c]pyridin-4(5H)-one (7, 0.200 g, 0.727 mmol) was converted according to general procedure B to give 8l (0.140 g, 66%) as a yellow solid: Mp>250° C.; IR (ATR) $v_{max}$ 2823, 1647, 1609, 1500, 1486, 1333, 1245, 1227, 1137, 757, 711 cm$^{-1}$; $^1$H NMR (400 MHz, DMSO-d$_6$) δ 12.81 (brs, 1H), 8.77 (s, 1H), 8.01-7.96 (m, 2H with an apparent s at 8.00 ppm), 7.48-7.38 (m, 2H), 7.34 (t, J=8.0 Hz, 1H); $^{13}$C NMR (75 MHz, DMSO-d$_6$) δ 160.1 (d, J$_{C-F}$=247.5 Hz), 158.0, 147.6, 139.2 (d, J$_{C-F}$=6.0 Hz), 137.5 (d, J$_{C-F}$=6.0 Hz), 135.7, 130.7 (d, J$_{C-F}$=9.0 Hz), 129.0, 127.1, 125.4 (d, J$_{C-F}$=3.0 Hz), 122.7 (d, J$_{C-F}$=5.2 Hz), 119.8 (d, J$_{C-F}$=12.7 Hz), 116.5 (d, J$_{C-F}$=22.5 Hz); $^{19}$F NMR (376 MHz, DMSO-d$_6$) δ −113.2; HRMS (ESI$^+$) m/z calcd for C$_{13}$H$_8$O$_3$N$_2$SF (M+H) 291.0234, found 291.0233.

2-(4-Chloro-3-fluorophenyl)-7-nitrothieno[3,2-c]pyridin-4(5H)-one (8m). 2-Bromo-7-nitrothieno[3,2-c]pyridin-4(5H)-one (7, 0.200 g, 0.727 mmol) was converted according to general procedure B to give 8m (0.142 g, 60%) as a yellow solid: Mp>250° C.; IR (ATR) $v_{max}$ 2838, 1655, 1607, 1477, 1335, 1238, 1187, 1138, 1040, 837, 808, 763, 703 cm$^{-1}$; $^1$H NMR (400 MHz, DMSO-d$_6$) δ 12.81 (brs, 1H), 8.78 (s, 1H), 8.14 (s, 1H), 8.02 (dd, J=10.4 Hz, 1.2 Hz, 1H), 7.72-7.64 (m, 2H); $^{13}$C NMR (100 MHz, DMSO-d$_6$) δ 158.1, 157.6 (d, J$_{C-F}$=246.0 Hz), 141.9, 139.1, 136.2, 133.4 (d, J$_{C-F}$=8.0 Hz), 131.4, 129.7, 127.1, 123.1 (d, J$_{C-F}$=3.0 Hz), 121.9, 119.6 (d, J$_{C-F}$=18.0 Hz), 114.2 (d, J$_{C-F}$=23.0 Hz); $^{19}$F NMR (376 MHz, DMSO-d$_6$) δ −115.0; HRMS (ESI$^+$) m/z calcd for C$_{13}$H$_7$O$_3$N$_2$SFCl (M+H) 324.9844, found 324.9844.

2-(3-Chloro-4-fluorophenyl)-7-nitrothieno[3,2-c]pyridin-4(5H)-one (8n). 2-Bromo-7-nitrothieno[3,2-c]pyridin-4(5H)-one (7, 0.200 g, 0.727 mmol) was converted according to general procedure B to give 8n (0.127 g, 54%) as a yellow solid: Mp>250° C.; IR (ATR) $v_{max}$ 2817, 1655, 1610, 1484, 1336, 1260, 1227, 1140, 1039, 895, 866, 818, 764, 712, 692 cm$^{-1}$; $^1$H NMR (300 MHz, DMSO-d$_6$) δ 12.77 (brs, 1H), 8.74 (s, 1H), 8.12 (dd, J=7.0 Hz, 2.1 Hz, 1H), 8.06 (s, 1H), 7.86-7.81 (m, 1H), 7.49 (t, J=8.7 Hz, 1H); $^{13}$C NMR (75 MHz, DMSO-d$_6$) δ 157.9, 157.2 (d, J$_{C-F}$=248.0 Hz), 141.9, 138.9, 135.8, 130.2, 129.7, 127.1, 126.7 (d, J$_{C-F}$=7.0 Hz), 121.4, 120.6 (d, J$_{C-F}$=18.0 Hz), 117.7 (d, J$_{C-F}$=21.0

Hz); $^{19}$F NMR (376 MHz, DMSO-d$_6$) δ −116.0; HRMS (ESI$^+$) m/z calcd for C$_{13}$H$_7$O$_3$N$_2$SFCl (M+H) 324.9844, found 324.9843.

4-(2-(4-(4,4,5,5-Tetramethyl-1,3,2-dioxaborolan-2-yl) phenoxy)ethyl)morpholine (24). To a solution of 4-(4,4,5,5-tetramethyl-1,3,2-dioxaborolan-2-yl)phenol (0.408 g, 1.85 mmol) in DMF (5 mL) were added 4-(2-chloroethyl)morpholine hydrochloride (0.383 g, 2.03 mmol), Cs$_2$CO$_3$ (1.52 g, 4.63 mmol), and KI (0.015 g, 0.092 mmol). The reaction mixture was heated to 65° C. for 12 h, cooled to room temperature, diluted with EtOAc (100 mL), washed with saturated aqueous NaHCO$_3$ (30 mL) and saturated aqueous NaCl (30 mL), dried (MgSO$_4$), filtered, and concentrated to give a brown solid. Purification by chromatography on SiO$_2$ (MeOH:CH$_2$Cl$_2$, 1:9) provided 24 (0.519 g, 84%) as an off-white powdery solid: $^1$H NMR (400 MHz, CDCl$_3$) δ 7.73 (d, J=8.4 Hz, 2H), 6.88 (d, J=8.8 Hz, 2H), 4.13 (t, J=5.6 Hz, 2H), 3.72 (t, J=4.8 Hz, 4H), 2.80 (t, J=5.6 Hz, 2H), 2.57 (t, J=4.8 Hz, 4H), 1.32 (s, 12H). Spectral data are consistent with literature properties.[39]

2-(4-(2-Morpholinoethoxy)phenyl-7-nitrothieno[3,2-c] pyrdin-4(5H)-one (8o). 2-Bromo-7-nitrothieno[3,2-c]pyridin-4(5H)-one (7, 0.250 g, 0.908 mmol) was treated according to general procedure B to give 8o (0.219 g, 60%) as a yellow solid: Mp>226° C. (dec.); IR (ATR) ν$_{max}$ 2804, 1654, 1611, 1491, 1338, 1248, 1112, 1039, 899, 821, 762, 712 cm$^{-1}$; $^1$H NMR (400 MHz, DMSO-d$_6$) δ 12.70 (brs, 1H), 8.71 (s, 1H), 7.83 (s, 1H), 7.76 (d, J=8.8 Hz, 2H), 7.04 (d, J=8.8H, 2H), 4.15 (t, J=5.6 Hz, 2H), 3.59 (t, J=4.4 Hz, 4H), 2.72 (t, J=5.6 Hz, 2H), 2.51-2.46 (m, 4H obstructed by DMSO signal); $^{13}$C NMR (75 MHz, DMSO-d$_6$) δ 159.0, 158.0, 144.8, 137.6, 135.1, 130.0, 127.4, 127.3, 124.9, 118.4, 115.3, 66.1, 65.5, 56.9, 53.5; HRMS (ESI$^+$) m/z calcd for C$_{19}$H$_{20}$N$_3$O$_5$S (M+H) 402.1118, found 402.1116.

General procedure C: Suzuki coupling of 2-bromo-6,7-dihydrothieno[3,2-c]pyridin-4(5H)-one. A 100-mL round-bottom flask was charged with Pd(PPh$_3$)$_4$(5.0 mol %) inside a glove box. The flask was removed from the glove box and sequentially charged with 2-bromo-6,7-dihydrothieno[3,2-c]pyridin-4(5H)-one (41, 1.0 equiv), aryl boronic acid (1.1 equiv), and Na$_2$CO$_3$ (2.3 equiv). The flask was purged under a stream of N$_2$, diluted with deoxygenated dioxane and H$_2$O (2:1, 0.1 M), fitted with a reflux condenser, and heated to 90° C. for 12 h. The resulting dark mixture was allowed to cool to room temperature, diluted with H$_2$O, and cooled in an ice-bath. The precipitate was filtered, washed with H$_2$O, dissolved in CH$_2$Cl$_2$, dried (MgSO$_4$), and concentrated to give a light colored solid. Typically, a ca. 10 mg aliquot of the crude material was purified by chromatography on SiO$_2$ (EtOAc) to characterize the Suzuki products. In some cases, residual Ph$_3$P(O) was difficult to remove prior to the next step (DDQ oxidation). Therefore, the entire batch of crude Suzuki material was purified by chromatography on SiO$_2$. In these cases, the Suzuki coupling and DDQ oxidation are reported with separate yields.

General procedure D: DDQ oxidation. The Suzuki coupling product (crude or purified) was suspended in dioxane (0.1 M) and treated with DDQ (2.0 equiv). The flask was fitted with a reflux condenser and heated to 100° C. for 24 h, allowed to cool to room temperature, and concentrated to give a dark solid. The solid was dissolved in EtOAc (500 mL), and the orange solution was then washed with saturated aqueous NaHCO$_3$ (4×60 mL) and saturated aqueous NaCl (MgSO$_4$), filtered, and concentrated to give a dark solid. The crude residue was purified as a solid by chromatography on SiO$_2$ (MeOH:CH$_2$Cl$_2$, 1:9), or suspended in CH$_2$Cl$_2$ (5 mL), sonicated for 2 min, and heated to reflux. Upon cooling to room temperature, the desired pyridone was obtained as a solid.

2-(p-Tolyl)-6,7-dihydrothieno[3,2-c]pyridin-4(5H)-one (25). According to procedure C, chromatography on SiO$_2$ (EtOAc) of an aliquot of the Suzuki reaction mixture provided 25 as a white solid: Mp 210-212° C.; IR (ATR) ν$_{max}$ 2833, 1650, 1480, 1299, 1092, 816, 763, 694 cm$^{-1}$; $^1$H NMR (500 MHz, CDCl$_3$) δ 7.57 (s, 1H), 7.45 (d, J=8.5 Hz, 2H), 7.18 (d, J=7.5 Hz, 2H), 5.76 (brs, 1H), 3.66 (td, J=6.5 Hz, 2.5 Hz, 2H), 3.06 (t, J=7.0 Hz, 2H), 2.36 (s, 3H); $^{13}$C NMR (125 MHz, CDCl$_3$) δ 163.6, 145.0, 142.4, 137.9, 132.9, 130.8, 129.7, 125.7, 120.8, 41.3, 24.5, 21.2; HRMS (ESI$^+$) m/z calcd for C$_{14}$H$_{14}$ONS (M+H) 244.0791, found 244.0789.

2-(4-Chlorophenyl)-6,7-dihydrothieno[3,2-c]pyridin-4 (5H)-one (26). According to general procedure C, chromatography on SiO$_2$ (EtOAc) of an aliquot of the crude Suzuki coupling provided 26 as a white solid: Mp 219-221° C.; IR (ATR) ν$_{max}$ 2955, 1652, 1482, 1296, 1094, 822, 775 cm$^{-1}$; $^1$H NMR (500 MHz, CDCl$_3$) δ 7.59 (s, 1H), 7.49 (d, J=11.0 Hz, 2H), 7.34 (d, J=11.5 Hz, 2H), 5.67 (brs, 1H), 3.67 (td, J=6.8, 3.0 Hz, 2H), 3.07 (t, J=7.0 Hz, 2H); $^{13}$C NMR (125 MHz, CDCl$_3$) δ 163.6, 145.9, 141.1, 134.0, 133.4, 132.4, 129.4, 127.1, 122.0, 41.5, 24.7; HRMS (ESI$^+$) m/z calcd for C$_{13}$H$_{11}$ONSCl (M+H) 264.0244, found 264.0244.

2-(4-(Trifluoromethyl)phenyl)-6,7-dihydrothieno[3,2-c] pyridin-4(5H)-one (27). According to general procedure C, the product obtained from 2-bromo-6,7-dihydrothieno[3,2-c]pyridin-4(5H)-one (41, 1.00 g, 4.30 mmol) was purified by chromatography on SiO$_2$ (EtOAc) to provide 27 (1.03 g, 80%) as an off-white solid: Mp 227-229° C.; IR (ATR) ν$_{max}$ 3192, 3072, 1653, 1485, 1319, 1163, 1108, 1065, 847, 780 cm$^{-1}$; $^1$H NMR (500 MHz, CDCl$_3$) δ 7.71 (s, 1H), 7.68-7.61 (m, 4H), 5.74 (brs, 1H), 3.68 (dt, J=6.8 Hz, 2.8 Hz, 2H), 3.09 (t, J=6.8 Hz, 2H); $^{13}$C NMR (125 MHz, CDCl$_3$) δ 163.3, 146.6, 140.4, 137.0, 133.3, 129.6 (q, J$_{C-F}$=31.2 Hz), 126.0 (q, J$_{C-F}$=3.7 Hz), 125.1, 124.0 (q, J$_{C-F}$ 270 Hz), 122.8, 41.2, 24.6; $^{19}$F NMR (470 MHz, CDCl$_3$) δ −62.6; HRMS (ESI$^+$) m/z calcd for C$_{14}$H$_{11}$F$_3$NOS (M+H) 298.0508, found 298.0503.

2-(4-Fluorophenyl)-6,7-dihydrothieno[3,2-c]pyridin-4 (5H)-one (28). According to general procedure C, the product obtained from 2-bromo-6,7-dihydrothieno[3,2-c]pyridin-4(5H)-one (41, 0.750 g, 3.23 mmol) was purified by chromatography on SiO$_2$ (EtOAc) to give 28 (0.673 g, 83%) as a light-brown solid: Mp 230-232° C.; IR (ATR) ν$_{max}$ 3211, 1643, 1474, 1134, 1304, 1225, 1162, 823, 780 cm$^{-1}$; $^1$H NMR (500 MHz, CDCl$_3$) δ 7.54 (s, 1H), 7.54-7.50 m (2H), 7.09-7.05 (m, 2H), 5.69 (brs, 1H), 3.66 (dt, J=6.5, 2.5 Hz, 2H), 3.07 (t, J=6.5 Hz, 2H); $^{13}$C NMR (125 MHz, CDCl$_3$) δ 163.4, 162.5 (d, J$_{C-F}$=246.2 Hz), 145.4, 141.1, 133.1, 129.8 (d, J$_{C-F}$=2.5 Hz), 127.7 (d, J$_{C-F}$=7.5 Hz), 121.3, 116.0 (d, J$_{C-F}$=21.2 Hz), 41.3, 24.5; $^{19}$F NMR (470 MHz, CDCl$_3$) δ −113.8; HRMS (ESI$^+$) m/z calcd for C$_{13}$H$_{11}$FNOS (M+H) 248.0540, found 248.0444.

2-(4-Hydroxyphenyl)-6,7-dihydrothieno[3,2-c]pyridin-4 (5H)-one (29). According to general procedure C, the product obtained from 2-bromo-6,7-dihydrothieno[3,2-c]pyridin-4(5H)-one (41, 1.06 g, 4.56 mmol) was purified by chromatography on SiO$_2$ (MeOH:CH$_2$Cl$_2$, 1:9) to give 29 (1.02 g, 91%) as a light-orange solid: Mp>250° C.; IR (ATR) ν$_{max}$ 3032, 1638, 1607, 1545, 1483, 1421, 1270, 1242, 1221, 1169, 1102, 983, 826, 771 cm$^{-1}$; $^1$H NMR (400 MHz, DMSO-d$_6$) δ 9.68 (s, 1H), 7.58 (brs, 1H), 7.44 (d, J=8.4 Hz, 2H), 7.36 (s, 1H), 6.79 (d, J=8.4 Hz, 2H), 3.44 (td, J=7.2, 2.4 Hz, 2H), 2.97 (t, J=6.8 Hz, 2H); $^{13}$C NMR (125 MHz, DMSO-d$_6$) δ 162.1, 157.3, 143.9, 141.3, 133.3, 126.7, 124.2, 119.1, 115.8, 40.2, 23.7; HRMS (ESI⁺) m/z calcd for C$_{13}$H$_{12}$O$_2$NS (M+H) 246.0583, found 246.0581.

4-(4-Oxo-4,5,6,7-tetrahydrothieno[3,2-c]pyridin-2-yl) phenyl pivalate (30). A solution of 2-(4-hydroxyphenyl)-6,7-dihydrothieno[3,2-c]pyridin-4(5H)-one (29, 1.03 g, 4.19 mmol) in THF (80 mL) was treated with Et$_3$N (1.18 mL, 8.39 mmol), followed by a solution of Piv$_2$O (1.57 g, 8.39 mmol) in THF (0.5 mL) and DMAP (0.076 g, 0.629 mmol). The flask was fitted with a reflux condenser and heated to 70° C. for 18 h. The reaction mixture was diluted with EtOAc (200 mL), washed with H$_2$O (50 mL), saturated aqueous NaCl (50 mL), dried (MgSO$_4$), filtered, and concentrated to give a tan solid. Purification by chromatography on SiO$_2$ (dry load, MeOH:CH$_2$Cl$_2$, 1:11) provided 30 (1.35 g, 97%) as a tan solid: Mp 233-234° C.; IR (ATR) $v_{max}$ 3203, 3070, 2966, 1752, 1655, 1475, 1200, 1162, 1106, 892, 842, 792 cm$^{-1}$; ¹H NMR (400 MHz, CDCl$_3$) δ 7.57 (s, 1H), 7.56 (d, J=8.8 Hz, 2H), 7.07 (d, J=8.8 Hz, 2H), 5.72 (brs, 1H), 3.66 (td, J=6.8, 2.8 Hz, 2H), 3.07 (t, J=6.8 Hz, 2H), 1.35 (s, 9H); ¹³C NMR (125 MHz, CDCl$_3$) δ 177.2, 163.7, 151.1, 145.7, 141.6, 133.3, 131.4, 127.0, 122.3, 121.7, 41.5, 39.4, 27.4, 24.7; HRMS (ESI⁺) m/z calcd for C$_{18}$H$_{20}$O$_3$NS (M+H) 330.1158, found 330.1158.

2-(3-(Trifluoromethyl)phenyl)-6,7-dihydrothieno[3,2-c]pyridin-4(5H)-one (31). According to general procedure C, chromatography on SiO$_2$ (EtOAc) of an aliquot of the crude Suzuki coupling product provided 31 as a white solid: Mp 149-151° C.; IR (ATR) $v_{max}$ 3191, 3067, 1650, 1482, 1327, 1121, 791, 690 cm$^{-1}$; ¹H NMR (400 MHz, CDCl$_3$) δ 7.80 (s, 1H), 7.73 (d, J=7.6 Hz, 1H), 7.69 (s, 1H), 7.55-7.49 (m, 2H), 5.57 (brs, 1H), 3.68 (td, J=6.4, 2.8 Hz, 2H), 3.10 (t, J=6.8 Hz, 2H); ¹³C NMR (100 MHz, CDCl$_3$) δ 163.7, 146.5, 140.5, 134.5, 133.3, 131.6 (q, J$_{C-F}$=32.0 Hz), 129.6, 128.9, 126.7 (q, J$_{C-F}$=276.0 Hz), 124.5 (q, J$_{C-F}$=4.0 Hz), 122.6, 122.5 (q, J$_{C-F}$=4.0 Hz), 41.3, 24.6; ¹⁹F NMR (376 MHz, CDCl$_3$) δ −62.8; HRMS (ESI⁺) m/z calcd for C$_{14}$H$_{11}$ONSF$_3$ (M+H) 298.0508, found 298.0507.

2-(p-Tolyl)thieno[3,2-c]pyridin-4(5H)-one (32). According to general procedures C and D, the product obtained from 2-bromo-6,7-dihydrothieno[3,2-c]pyridin-4(5H)-one (41, 0.625 g, 2.69 mmol) was precipitated from CH$_2$Cl$_2$ to provide 32 (0.344 g, 53% over two steps) as a tan solid: Mp 249-251° C.; IR (ATR) $v_{max}$ 2811, 1639, 1607, 1507, 1120, 1148, 809, 766, 746, 698 cm$^{-1}$; ¹H NMR (400 MHz, DMSO-d$_6$) δ 11.44 (brs, 1H), 7.78 (s, 1H), 7.63 (d, J=8.0 Hz, 2H), 7.26-7.25 (m, 3H), 6.83 (d, J=6.8 Hz, 1H), 2.33 (s, 3H); ¹³C NMR (125 MHz, DMSO-d$_6$) δ 157.9, 146.6, 140.8, 137.2, 131.0, 129.6, 129.2, 129.1, 125.0, 118.6, 100.2, 20.1; HRMS (ESI⁺) m/z calcd for C$_{14}$H$_{12}$NOS (M+H) 242.0634, found 242.0511.

2-(4-Chlorophenyl)thieno[3,2-c]pyridin-4(5H)-one (33). According to general procedures C and D, the product obtained from 2-bromo-6,7-dihydrothieno[3,2-c]pyridin-4(5H)-one (41, 0.625 g, 2.69 mmol) was precipitated from CH$_2$Cl$_2$ to provide 33 (0.338 g, 48% over two steps) as a tan solid: Mp>250° C.; IR (ATR) $v_{max}$ 2834, 1653, 1604, 1482, 1405, 1218, 1095, 813, 762, 695 cm$^{-1}$; ¹H NMR (400 MHz, DMSO-d$_6$) δ 11.50 (brs, 1H), 7.90 (s, 1H), 7.79-7.76 (m, 2H), 7.51-7.49 (m, 2H), 7.28 (d, J=6.8 Hz, 1H), 6.86 (d, J=6.8 Hz, 1H); ¹³C NMR (125 MHz, DMSO-d$_6$) δ 158.5, 147.8, 139.7, 132.7, 131.9, 131.5, 130.2, 129.1, 127.4, 120.7, 100.8; HRMS (ESI⁺) m/z calcd for C$_{13}$H$_9$NOSCl (M+H) 262.0088, found 262.0016.

2-(4-(Trifluoromethyl)phenyl)thieno[3,2-c]pyridin-4(5H)-one (34). According to general procedure D, the product obtained from 2-(4-(trifluoromethyl)phenyl)-6,7-dihydrothieno[3,2-c]pyridin-4(5H)-one (27, 0.702 g, 2.36 mmol) was purified by chromatography on SiO$_2$ (MeOH:CH$_2$Cl$_2$, 1:9) to provide 34 (0.539 g, 77%) as a tan solid: Mp>250° C.; IR (ATR) $v_{max}$ 2830, 1643, 1607, 1323, 1106, 1067, 828, 767 cm$^{-1}$; ¹H NMR (400 MHz, DMSO-d$_6$) δ 11.53 (brs, 1H), 8.05 (s, 1H), 7.98 (d, J=8.0 Hz, 2H), 7.79 (d, J=8.4 Hz, 2H), 7.31 (t, J=6.4 Hz, 1H), 6.89 (d, J=7.2 Hz, 1H); ¹³C NMR (125 MHz, DMSO-d$_6$) δ 159.1, 149.0, 139.6, 137.4, 131.9, 131.3, 128.5 (q, J$_{C-F}$=31.2 Hz), 126.3 (q, J$_{C-F}$=3.7 Hz), 124.6 (q, J$_{C-F}$=271.2 Hz), 122.5, 101.3; ¹⁹F NMR (470 MHz, DMSO-d$_6$) δ −61.0; HRMS (ESI⁺) m/z calcd for C$_{14}$H$_9$F$_3$NOS (M+H) 296.0351, found 296.0352.

2-(4-Fluorophenyl)thieno[3,2-c]pyridin-4(5H)-one (35). According to general procedure D, the product obtained from 2-(4-fluorophenyl)-6,7-dihydrothieno[3,2-c]pyridin-4(5H)-one (28, 0.673 g, 2.72 mmol) was purified by chromatography on SiO$_2$ (MeOH:CH$_2$Cl$_2$, 1:9) to provide 35 (0.285 g, 41%) as an off-white solid: Mp>250° C.; IR (ATR) $v_{max}$ 2838, 1655, 1605, 1505, 1493, 1235, 1150, 822, 750 cm$^{-1}$; ¹H NMR (400 MHz, DMSO-d$_6$) δ 11.46 (brs, 1H), 7.82 (s, 1H), 7.82-7.78 (m, 2H), 7.31-7.24 (m, 3H), 6.84 (d, J=7.2 Hz, 1H); ¹³C NMR (125 MHz, DMSO-d$_6$) δ 161.9 (d, J$_{C-F}$=245.0 Hz), 158.5, 147.5, 140.0, 131.5, 130.0, 129.5 (d, J$_{C-F}$=2.5 Hz), 127.8 (d, J$_{C-F}$=8.7 Hz), 120.0, 116.0 (d, J$_{C-F}$ 21.2 Hz), 100.7; ¹⁹F (470 MHz, DMSO-d$_6$) δ −113.4; HRMS (ESI⁺) m/z calcd for C$_{13}$H$_9$FNOS (M+H) 246.0383, found 246.0381.

4-(4-Oxo-4,5,dihydrothieno[3,2-c]pyridin-2-yl)phenyl pivalate (36). According to general procedure D, the product obtained from 4-(4-oxo-4,5,6,7-tetrahydrothieno[3,2-c]pyridin-2-yl)phenyl pivalate (30, 1.35 g, 4.09 mmol) was purified by chromatography on SiO$_2$ (MeOH:CH$_2$Cl$_2$, 1:9) to provide 36 (0.750 g, 56%) as a tan solid: Mp>250° C.; IR (ATR) $v_{max}$ 2961, 2872, 2837, 1749, 1637, 1603, 1507, 1491, 1472, 1271, 1205, 1165, 1112, 891, 840, 757 cm$^{-1}$; ¹H NMR (400 MHz, DMSO-d$_6$) δ 11.47 (brs, 1H), 7.86 (s, 1H), 7.80-7.77 (m, 2H), 7.26 (t, J=6.4 Hz, 1H), 7.19-7.17 (m, 2H), 6.85 (d, J=6.8 Hz, 1H), 1.32 (s, 9H); ¹³C NMR (125 MHz, DMSO-d$_6$) δ 176.2, 158.5, 150.6, 147.5, 140.2, 131.5, 130.5, 129.9, 126.8, 122.4, 120.1, 100.7, 38.5, 26.6; HRMS (ESI⁺) m/z calcd for C$_{18}$H$_{18}$O$_3$NS (M+H) 328.1002, found 328.1000.

2-(3-(Trifluoromethyl)phenyl)thieno[3,2-c]pyridin-4(5H)-one (37). According to general procedures C and D, the product obtained from 2-bromo-6,7-dihydrothieno[3,2-c]pyridin-4(5H)-one (41, 0.625 g, 2.69 mmol) was precipitated from CH$_2$Cl$_2$ to provide 37 (0.544 g, 69% over two steps) as a tan solid: Mp 201-204° C.; IR (ATR) $v_{max}$ 2823, 1648, 1607, 1327, 1166, 1112, 1071, 991, 891, 756, 688 cm$^{-1}$; ¹H NMR (400 MHz, DMSO-d$_6$) δ 11.52 (brs, 1H), 8.09 (s, 1H), 8.08-8.04 (m, 2H), 7.70-7.68 (m, 2H), 7.31 (d, J=6.8 Hz, 1H), 6.88 (d, J=6.8 Hz, 1H); ¹³C NMR (125 MHz, DMSO-d$_6$) δ 158.6, 148.2, 139.1, 134.1, 131.6, 130.6, 130.4, 129.9 (q, J$_{C-F}$=31.2 Hz), 129.7, 124.4 (q, J$_{C-F}$=3.7 Hz), 123.8 (q, J$_{C-F}$=271.2 Hz), 121.9 (q, J$_{C-F}$=3.7 Hz), 121.8, 100.8; ¹⁹F NMR (376 MHz, DMSO-d$_6$) δ −61.2; HRMS (ESI⁺) m/z calcd for C$_{14}$H$_9$ONSF$_3$ (M+H) 296.0351, found 296.0349.

General procedure E: Nitration of pyridones. A suspension of the DDQ oxidation product (1.0 equiv) in MeCN (0.04 M) was heated to 65° C. in a round-bottom flask fitted with a condenser under an atmosphere of O$_2$ (balloon, 1 atm). Neat t-BuONO (4.0 equiv) was added, and the reaction mixture was stirred for 3-5 h, or until consumption of starting material was observed by TLC analysis. Typically, the reaction mixture stayed heterogeneous, but slightly darkened. The solution was cooled to room temperature and concentrated to approximately ½ volume. The precipitate was filtered to give the pure nitration product. In some cases when the solid was not pure, it was resuspended in MeCN, sonicated for 5 min, and filtered.

7-Nitro-2-(p-tolyl)thieno[3,2-c]pyridin-4(5H)-one (8a). According to general procedure E, 2-(p-tolyl)thieno[3,2-c]pyridin-4(5H)-one (32, 0.175 g, 0.725 mmol) led to 8a (0.082 g, 39%) as a yellow solid: Mp>250° C.; IR (ATR) $v_{max}$ 2825, 1649, 1492, 1250, 1027, 806, 765 cm$^{-1}$; $^1$H NMR (500 MHz, DMSO-d$_6$) δ 12.73 (brs, 1H), 8.73 (s, 1H), 7.91 (s, 1H), 7.74 (d, J=8.0 Hz, 2H), 7.29 (d, J=8.0 Hz, 2H), 2.35 (s, 3H); $^{13}$C NMR (125 MHz, DMSO-d$_6$) δ 157.9, 144.9, 138.6, 138.0, 135.2, 129.9, 129.5, 127.3, 125.9, 119.2, 20.7; HRMS (ESI$^+$) m/z calcd for $C_{14}H_{11}O_3N_2S$ (M+H) 287.0485, found 287.0483.

2-(4-Chlorophenyl)-7-nitrothieno[3,2-c]pyridin-4(5H)-one (8b). According to general procedure E, 2-(4-chlorophenyl)thieno[3,2-c]pyridin-4(5H)-one (33, 0.164 g, 0.626 mmol) led to 8b (0.108 g, 56%) as a yellow solid: Mp>250° C.; IR (ATR) $v_{max}$ 2806, 1655, 1482, 1335, 1255, 1231, 1093, 815, 764, 706 cm$^{-1}$; $^1$H NMR (400 MHz, DMSO-d$_6$) δ 12.79 (brs, 1H), 8.76 (s, 1H), 8.03 (s, 1H), 7.89 (d, J=8.4 Hz, 2H), 7.53 (d, J=8.8 Hz, 2H); $^{13}$C NMR (125 MHz, DMSO-d$_6$) δ 157.8, 143.2, 138.6, 135.6, 133.3, 131.1, 129.8, 129.2, 127.7, 127.2, 120.6; HRMS (ESI$^+$) m/z calcd for $C_{13}H_8O_3N_2ClS$ (M+H) 306.9939, found 306.9937.

7-Nitro-2-(4-(trifluoromethyl)phenyl)thieno[3,2-c]pyridin-4(5H)-one (8c). According to general procedure E, 2-(4-(trifluoromethyl)phenyl)thieno[3,2-c]pyridin-4(5H)-one (34, 0.447 g, 1.51 mmol) led to 8c (0.406 g, 79%) as a yellow solid: Mp>250° C.; IR (ATR) $v_{max}$ 2803, 1664, 1611, 1494, 1322, 1231, 1109, 1065, 832, 766 cm$^{-1}$; $^1$H NMR (500 MHz, DMSO-d$_6$) δ 12.82 (brs, 1H), 8.78 (s, 1H), 8.17 (s, 1H), 8.10 (d, J=8.0 Hz, 2H), 7.81 (d, J=8.5 Hz, 2H); $^{13}$C NMR (125 MHz, DMSO-d$_6$) δ 157.9, 142.5, 139.3, 136.1, 136.0, 129.7, 128.5 (q, $J_{C-F}$=31.2 Hz), 127.1, 126.5, 126.1 (q, $J_{C-F}$=3.7 Hz), 124.0 (q, $J_{C-F}$=270.0 Hz), 121.9; $^{19}$F NMR (470 MHz, DMSO-d$_6$) δ −61.1; HRMS (ESI$^+$) m/z calcd for $C_{14}H_8F_3N_2O_3S$ (M+H) 341.0202, found 341.0201.

2-(4-Fluorophenyl)-7-nitrothieno[3,2-c]pyridin-4(5H)-one (8d). According to general procedure E, 2-(4-fluorophenyl)thieno[3,2-c]pyridin-4(5H)-one (35, 0.230 g, 0.937 mmol) led to 8d (0.133 g, 49%) as a yellow solid: Mp>250° C.; IR (ATR) $v_{max}$ 2807, 1649, 1617, 1491, 1340, 1248, 1226, 1135, 822, 764 cm$^{-1}$; $^1$H NMR (400 MHz, DMSO-d$_6$) δ 12.77 (brs, 1H), 8.75 (s, 1H), 7.97 (s, 1H), 7.93-7.89 (m, 2H), 7.32 (t, J=8.0 Hz, 2H); $^{13}$C NMR (125 MHz, DMSO-d$_6$) δ 162.2 (d, $J_{C-F}$=245.0 Hz), 157.8, 143.5, 138.3, 135.3, 129.8, 128.9 (d, $J_{C-F}$=2.5 Hz), 128.7 (d, $J_{C-F}$=8.7 Hz), 127.2, 120.0, 116.2 (d, $J_{C-F}$=21.2 Hz); $^{19}$F NMR (470 MHz, DMSO-d$_6$) δ −112.6; HRMS (ESI$^+$) m/z calcd for $C_{13}H_8FN_2O_3S$ (M+H) 291.0234, found 291.0233.

4-(7-Nitro-4-oxo-4,5,dihydrothieno[3,2-c]pyridin-2-yl)phenyl pivalate (8e). According to general procedure E, 4-(4-oxo-4,5,dihydrothieno[3,2-c]pyridin-2-yl)phenyl pivalate (36, 0.854 g, 2.60 mmol) led to 8e (0.791 g, 81%) as a yellow solid: Mp>250° C.; IR (ATR) $v_{max}$ 3264, 3085, 2979, 1720, 1671, 1609, 1515, 1481, 1330, 1204, 1167, 1131, 776 cm$^{-1}$; $^1$H NMR (400 MHz, DMSO-d$_6$) δ 12.78 (brs, 1H), 8.75 (d, J=6.4 Hz, 1H), 7.99 (s, 1H), 7.91 (d, J=8.4 Hz, 2H), 7.21 (d, J=8.8 Hz, 2H), 1.32 (s, 9H); $^{13}$C NMR (125 MHz, DMSO-d$_6$) δ 176.2, 157.8, 151.1, 143.8, 138.4, 135.3, 129.8, 127.1, 122.5, 120.0, 38.5, 26.6; HRMS (ESI$^+$) m/z calcd for $C_{18}H_{17}O_5N_2S$ (M+H) 373.0853, found 373.0851.

7-Nitro-2-(3-(trifluoromethyl)phenyl)thieno[3,2-c]pyridin-4(5H)-one (8g). According to general procedure E, 2-(3-(trifluoromethyl)phenyl)thieno[3,2-c]pyridin-4(5H)-one (37, 0.354 g, 1.19 mmol) led to 8g (0.307 g, 75%) as a yellow solid: Mp>250° C.; IR (ATR) $v_{max}$ 2793, 1665, 1615, 1498, 1477, 1329, 1247, 1228, 1158, 1109, 996, 892, 764 cm$^{-1}$; $^1$H NMR (300 MHz, DMSO-d$_6$) δ 12.80 (brs, 1H), 8.78 (s, 1H), 8.22-8.14 (m, 3H), 7.78-7.68 (m, 2H); $^{13}$C NMR (100 MHz, d$_6$-DMSO) δ 157.9, 142.6, 139.1, 136.0, 133.4, 130.5, 130.1 (q, $J_{C-F}$=35.0 Hz), 130.0, 129.8, 127.2, 125.1 (q, $J_{C-F}$=5.0 Hz), 123.9 (q, $J_{C-F}$=271.0 Hz), 122.3 (q, $J_{C-F}$=4.0 Hz), 121.8; $^{19}$F NMR (376 MHz, DMSO-d$_6$) δ −61.1; HRMS (ESI$^+$) m z calcd for $C_{14}H_8O_3N_2F_3S$ (M+H) 341.0202, found 341.0200.

2-(3-Methoxyphenyl)-7-nitrothieno[3,2-c]pyridin-4(5H)-one (8j). According to general procedure E, 2-(3-methoxyphenyl)thieno[3,2-c]pyridin-4(5H)-one (0.085 g, 0.330 mmol) led to 8j (0.053 g, 53%) as a yellow solid: Mp>250° C.; IR (ATR) $v_{max}$ 2823, 1674, 1595, 1469, 1338, 1241, 1037, 763, 679 cm$^{-1}$; $^1$H NMR (400 MHz, DMSO-d$_6$) δ 12.77 (brs, 1H), 8.76 (s, 1H), 8.04 (s, 1H), 7.40-7.38 (m, 3H), 7.00-6.96 (m, 1H), 3.85 (s, 3H); $^{13}$C NMR (125 MHz, DMSO-d$_6$) δ 159.9, 157.9, 144.5, 138.4, 135.4, 133.5, 130.4, 129.8, 127.2, 120.3, 118.3, 115.0, 110.9, 55.3; HRMS (ESI$^+$) m/z calcd for $C_{14}H_{11}O_4N_2S$ (M+H) 303.0434, found 303.0297.

General procedure F: Nitro reduction and in-flow photooxygenation. A suspension of nitro-compound (1.0 equiv) in MeOH:EtOAc (3:1, 0.05 M) was treated under a nitrogen atmosphere with 10% Pd/C (15 mol %). $H_2$ was bubbled through the mixture. The suspension was stirred at room temperature under $H_2$ (1 atm, balloon) for 6 h, filtered through Celite, and the Celite pad was washed with MeOH (50 mL). The Pd/C was removed from the Celite, boiled in PhMe (40 mL), filtered over Celite, and eluted with MeOH. This procedure was performed twice. The combined filtrates were concentrated under reduced pressure to afford a brown solid that was used in the in-flow photooxygenation without further purification. A solution of the crude solid in MeOH (ca. 2-3 mL/mg) was passed through the tubing at a rate of 1.9 mL/min using the peristaltic pump (5 RPM) under white LED irradiation. The tubing was flushed with MeOH (40 mL). The mixture was concentrated to give a brown solid that was purified by chromatography on $SiO_2$ (dry loaded, acetone:hexanes, 1:2 to 1:1) to yield the desired imine.

2-(p-Tolyl)-7-iminothieno[3,2-c]pyridine-4,6(5H,7H)-dione (9a). According to general procedure F, the product obtained from 7-nitro-2-(p-tolyl)thieno[3,2-c]pyridin-4(5H)-one (8a, 0.080 g, 0.279 mmol) was purified by chromatography on $SiO_2$ (acetone:hexanes, 1:2) to give 9a (0.032 g, 42%) as a yellow solid: Mp 254-255° C.; IR (ATR) $v_{max}$ 3288, 3225, 1712, 1687, 1612, 1391, 1301, 1194, 1153, 781 cm$^{-1}$; $^1$H NMR (400 MHz, DMSO-d$_6$) δ 11.85 (brs, 1H), 11.56 (s, 1H), 7.92 (s, 1H), 7.76 (d, J=8.0 Hz, 2H), 7.30 (d, J=8.0 Hz, 2H), 2.35 (s, 3H); $^{13}$C NMR (125 MHz, DMSO-d$_6$) δ 160.0, 157.8, 153.3, 149.6, 141.3, 139.4, 136.8, 129.9, 129.2, 126.0, 121.4, 20.8; HRMS (ESI$^+$) m/z calcd for $C_{14}H_{11}N_2O_2S$ (M+H) 271.0536, found 271.0535.

2-(4-Chlorophenyl)-7-iminothieno[3,2-c]pyridine-4,6(5H,7H)-dione (9b). According to general procedure F, the product obtained from 2-(4-chlorophenyl)-7-nitrothieno[3,2-c]pyridin-4(5H)-one (8b, 0.095 g, 0.309 mmol) was purified by chromatography on $SiO_2$ (acetone:hexanes, 1:2) to give 9b (0.030 g, 33%) as a yellow solid: Mp 237-238° C.; IR (ATR) $v_{max}$ 3186, 1730, 1669, 1614, 1441, 1241, 1161, 1093, 815 cm$^{-1}$; $^1$H NMR (400 MHz, DMSO-d$_6$) δ 11.87 (brs, 1H), 11.63 (s, 1H), 8.03 (s, 1H), 7.91 (d, J=8.4 Hz, 2H), 7.55 (d, J=8.4 Hz, 2H); $^{13}$C NMR (125 MHz, DMSO-d$_6$) δ 160.0, 157.8, 153.4, 147.7, 142.2, 136.8, 134.1, 130.8, 129.3, 127.9, 122.7; HRMS (ESI$^+$) m/z calcd for $C_{13}H_8N_2O_2ClS$ (M+H) 290.9990, found 290.9989.

7-Imino-2-(4-(trifluoromethyl)phenyl)thieno[3,2-c]pyridine-4,6(5H,7H)-dione (9c). According to general procedure F, the product obtained from 7-nitro-2-(4-(trifluoromethyl)phenyl)thieno-[3,2-c]pyridin-4(5H)-one (8c, 0.125 g, 0.367 mmol) was purified by chromatography on $SiO_2$ (acetone: hexanes, 1:2) to give 9c (0.041 g, 34%) as a greenish/yellow solid: Mp>250° C.; IR (ATR) $v_{max}$ 3249, 3181, 1692, 1615, 1325, 1247, 1158, 1132, 1068, 831, 787 cm$^{-1}$; $^1$H NMR (400 MHz, DMSO-d$_6$) δ 11.90 (s, 1H), 11.70 (s, 1H), 8.16 (s, 1H), 8.11 (d, J=8.0 Hz, 2H), 7.84 (d, J=8.40 Hz, 2H); $^{13}$C NMR (125 MHz, DMSO-d$_6$) δ 159.9, 157.7, 153.4, 147.0, 143.1, 136.8, 135.8, 129.2 (q, $J_{C-F}$=31.2 Hz), 126.9, 126.1 (q, $J_{C-F}$=3.7 Hz), 124.0 (q, $J_{C-F}$=270 Hz), 123.9; $^{19}$F NMR (470 MHz, DMSO-d$_6$) δ −61.2; HRMS (ESI$^+$) m/z calcd for $C_{14}H_8F_3N_2O_2S$ (M+H) 325.0253, found 325.0252.

2-(4-Fluorophenyl)-7-iminothieno[3,2-c]pyridine-4,6 (5H,7H)-dione (9d). According to general procedure F, the product obtained from 2-(4-fluorophenyl)-7-nitrothieno[3,2-c]pyridin-4(5H)-one (8d, 0.105 g, 0.361 mmol) was purified by chromatography on $SiO_2$ (acetone:hexanes, 1:2) to give 9d (0.025 g, 25%) as a yellow solid: Mp 239-241° C.; IR (ATR) $v_{max}$ 3259, 2970, 1698, 1608, 1596, 1437, 1377, 1362, 1148, 908, 824 cm$^{-1}$; $^1$H NMR (400 MHz, DMSO-d$_6$) δ 11.87 (brs, 1H), 11.60 (s, 1H), 7.97-7.92 (m, 3H), 7.34 (t, J=8.8 Hz, 2H); $^{13}$C NMR (125 MHz, DMSO-d$_6$) δ 162.6 (d, $J_{C-F}$=246.0 Hz), 159.9, 157.7, 153.3, 148.1, 141.9, 136.8, 128.5 (d, $J_{C-F}$=2.5 Hz), 122.2, 116.3 (d, $J_{C-F}$=22.5 Hz); $^{19}$F NMR (470 MHz, DMSO-d$_6$) δ −111.4; HRMS (ESI$^+$) m/z calcd for $C_{13}H_8N_2O_2FS$ (M+H) 275.0285, found 275.0283.

4-(7-Imino-4,6-dioxo-4,5,6,7-tetrahydrothieno[3,2-c] pyridin-2-yl)phenyl pivalate (9e). According to general procedure F, the product obtained from 4-(7-nitro-4-oxo-4,5, dihydrothieno[3,2-c]pyridin-2-yl)phenyl pivalate (8e, 0.175 g, 0.469 mmol) was purified by chromatography on $SiO_2$ (acetone:hexanes, 1:2) to give 9e (0.029 g, 17%) as a tan solid: Mp 249-251° C.; IR (ATR) $v_{max}$ 3240, 3094, 1746, 1719, 1695, 1608, 1439, 1245, 1218, 1164, 1113, 792 cm$^{-1}$; $^1$H NMR (400 MHz, DMSO-d$_6$) δ 11.86 (s, 1H), 11.60 (s, 1H), 7.99 (s, 1H), 7.93 (d, J=8.8 Hz, 2H), 7.23 (d, J=8.8 Hz, 2H), 1.32 (s, 9H); $^{13}$C NMR (100 MHz, DMSO-d$_6$) δ 176.3, 160.1, 157.8, 153.4, 151.6, 148.4, 142.0, 136.8, 129.6, 127.5, 122.7, 122.3, 38.6, 26.7; HRMS (ESI$^+$) m/z calcd for $C_{18}H_{17}N_2O_4S$ (M+H) 357.0904, found 357.0903.

2-(3-Methoxyphenyl)-7-iminothieno[3,2-c]pyridine-4,6 (5H,7H)-dione (9f). According to general procedure F, the product obtained from 2-(3-fluorophenyl)-7-nitrothieno[3,2-c]pyridin-4(5H)-one (8f, 0.085 g, 0.292 mmol) was purified by chromatography on $SiO_2$ (acetone:hexanes, 1:2) to give 9f (0.028 g, 35%) as a yellow solid: Mp 235-236° C.; IR (ATR) $v_{max}$ 3251, 3187, 3097, 1692, 1611, 1579, 1431, 1310, 1271, 1226, 1156, 962, 778 cm$^{-1}$; $^1$H NMR (300 MHz, DMSO-d$_6$) δ 11.87 (brs, 1H), 11.64 (s, 1H), 8.09 (s, 1H), 7.81 (d, J=13.6 Hz, 1H), 7.70 (d, J=11.2 Hz, 1H), 7.57-7.49 (m, 1H), 7.32-7.25 (m, 1H); $^{13}$C NMR (125 MHz, DMSO-d$_6$) δ 162.5 (d, $J_{C-F}$=243.7 Hz), 159.8, 157.6, 153.3, 147.5 (d, $J_{C-F}$=1.2 Hz), 142.4, 136.7, 134.1 (d, $J_{C-F}$=8.7 Hz), 131.3 (d, $J_{C-F}$=8.7 Hz), 123.1, 122.3 (d, $J_{C-F}$=1.2 Hz) 116.1 (d, $J_{C-F}$=20.0 Hz), 112.9 (d, $J_{C-F}$=23.7 Hz); $^{19}$F NMR (376 MHz, DMSO-d$_6$) δ −111.8; HRMS (ESI$^+$) m/z calcd for $C_{13}H_8N_2O_2FS$ (M+H) 275.0285, found 275.0283.

7-Imino-2-(3-(trifluoromethyl)phenyl)thieno[3,2-c]pyridine-4,6(5H,7H)-dione (9g). According to general procedure F, the product obtained from 7-nitro-2-(3-(trifluoromethyl)phenyl)thieno-[3,2-c]pyridin-4(5H)-one (8g, 0.128 g, 0.376 mmol) was purified by chromatography on $SiO_2$ (acetone:hexanes, 1:2) to give 9g (0.029 g, 23%) as a yellow solid: Mp 236-238° C.; IR (ATR) $v_{max}$ 3188, 3103, 1731, 1680, 1617, 1426, 1335, 1242, 1177, 1161, 1128, 800, 689 cm$^{-1}$; $^1$H NMR (400 MHz, DMSO-d$_6$) δ 11.89 (s, 1H), 11.68 (s, 1H), 8.25 (s, 1H), 8.23 (s, 1H), 8.17 (d, J=7.6 Hz, 1H), 7.80 (d, J=7.6 Hz, 1H), 7.73 (t, J=7.6 Hz, 1H); $^{13}$C NMR (100 MHz, DMSO-d$_6$) δ 160.0, 157.8, 153.4, 147.1, 142.9, 136.8, 133.1, 130.6, 130.3 (q, $J_{C-F}$=33.0 Hz), 125.8 (q, $J_{C-F}$=4.0 Hz), 123.9, 123.8 (q, $J_{C-F}$=270.0 Hz), 122.7 (q, $J_{C-F}$=4.0 Hz); $^{19}$F NMR (376 MHz, DMSO-d$_6$) δ −61.3; HRMS (ESI$^+$) m/z calcd for $C_{14}H_8N_2O_2F_3S$ (M+H) 325.0253, found 325.0251.

2-(3-Chlorophenyl)-7-iminothieno[3,2-c]pyridine-4,6 (5H,7H)-dione (9h). According to general procedure F, the product obtained from 2-(3-chlorophenyl)-7-nitrothieno[3,2-c]pyridin-4(5H)-one (8h, 0.040 g, 0.130 mmol) was purified by chromatography on $SiO_2$ (acetone:hexanes, 1:2) to give 9h (0.013 g, 34%) as a yellow solid: Mp 226-228° C.; IR (ATR) $v_{max}$ 3211, 3079, 1725, 1676, 1610, 1565, 1433, 1300, 1236, 1220, 1156, 772, 678 cm$^{-1}$; $^1$H NMR (300 MHz, DMSO-d$_6$) δ 11.87 (brs, 1H), 11.65 (s, 1H), 8.10 (s, 1H), 8.00 (s, 1H), 7.85-7.81 (m, 1H), 7.52-7.50 (m, 2H); $^{13}$C NMR (100 MHz, DMSO-d$_6$) δ 159.9, 157.7, 153.4, 147.3, 142.5, 136.7, 134.2, 133.9, 131.2, 129.2, 125.7, 124.9, 123.3; HRMS (ESI$^-$) m/z calcd for $C_{13}H_6N_2O_2SCl$ (M−H) 288.9833, found 288.9842.

7-Imino-2-(m-tolyl)thieno[3,2-c]pyridine-4,6(5H,7H)-dione (9i). According to general procedure F, the product obtained from 7-nitro-2-(m-tolyl)thieno[3,2-c]pyridin-4 (5H)-one (8i, 0.075 g, 0.261 mmol) was purified by chromatography on $SiO_2$ (acetone:hexanes, 1:2) to give 9i (0.018 g, 25%) as a yellow solid: Mp 234-235° C.; IR (ATR) $v_{max}$ 3208, 3092, 1714, 1686, 1610, 1379, 1307, 1172, 1153, 888, 772, 684 cm$^{-1}$; $^1$H NMR (300 MHz, DMSO-d$_6$) δ 11.84 (brs, 1H), 11.57 (s, 1H), 7.95 (s, 1H), 7.71 (s, 1H), 7.65 (d, J=8.4 Hz, 1H), 7.37 (t, J=7.8 Hz, 1H), 7.26 (d, J=7.5 Hz, 1H), 2.37 (s, 3H); $^{13}$C NMR (100 MHz, DMSO-d$_6$) δ 160.1, 157.8, 153.4, 149.5, 141.7, 138.8, 136.7, 131.9, 130.3, 129.3, 126.7, 123.3, 121.9, 20.9; HRMS (ESI$^+$) m/z calcd for $C_{14}H_{11}N_2O_2S$ (M+H) 271.0536, found 271.0533.

2-(3-Methoxyphenyl)-7-iminothieno[3,2-c]pyridine-4,6 (5H,7H)-dione (9j). According to general procedure F, the product obtained from 2-(3-methoxyphenyl)-7-nitrothieno [3,2-c]pyridin-4(5H)-one (8j, 0.040 g, 0.132 mmol) was purified by chromatography on $SiO_2$ (acetone:hexanes, 1:2) to give 9j (0.008 g, 23%) as a tan solid: Mp 226-227° C.; IR (ATR) $v_{max}$ 3210, 1694, 1614, 1593, 1463, 1437, 1260, 1230, 1158, 1028, 783, 680 cm$^{-1}$; $^1$H NMR (400 MHz, DMSO-d$_6$) δ 11.86 (s, 1H), 11.59 (s, 1H), 8.04 (s, 1H), 7.41-7.37 (m, 3H), 7.03-7.00 (m, 1H), 3.85 (s, 3H); $^{13}$C NMR (125 MHz, DMSO-d$_6$) δ 160.0, 159.9, 157.8, 153.4, 149.2, 141.8, 136.7, 133.2, 130.5, 122.4, 118.5, 115.6, 111.1, 55.4; HRMS (ESI$^+$) m/z calcd for $C_{14}H_{11}N_2O_2S$ (M+H) 287.0485, found 287.0484.

2-(2-Chlorophenyl)-7-iminothieno[3,2-c]pyridine-4,6 (5H,7H)-dione (9k). According to general procedure F, the product obtained from 2-(2-chlorophenyl)-7-nitrothieno[3,2-c]pyridin-4(5H)-one (8k, 0.111 g, 0.361 mmol) was purified by chromatography on $SiO_2$ (acetone:hexanes, 1:2) to give 9k (0.033 g, 31%) as a yellow solid: Mp 220-221° C.; IR (ATR) 3226, 3192, 3080, 1724, 1678, 1608, 1408, 1307, 1224, 1165, 914, 887, 758, 731 cm$^{-1}$; $^1$H NMR (300 MHz, DMSO-d$_6$) δ 11.88 (brs, 1H), 11.66 (s, 1H), 7.84 (s, 1H), 7.83-7.78 (m, 2H), 7.68-7.64 (m, 1H), 7.53-7.47 (m, 2H); $^{13}$C NMR (100 MHz, DMSO-d$_6$) δ 160.0, 157.8, 153.5, 144.9, 143.5, 135.6, 131.7, 131.1, 131.0, 130.7, 130.6, 128.1, 126.5; HRMS (ESI$^+$) m/z calcd for $C_{13}H_8N_2O_2SCl$ (M+H) 290.9990, found 290.9984.

2-(2-Fluorophenyl)-7-iminothieno[3,2-c]pyridine-4,6(5H,7H)-dione (9l). According to general procedure F, the product obtained from 2-(2-fluorophenyl)-7-nitrothieno[3,2-c]pyridin-4(5H)-one (8l, 0.138 g, 0.475 mmol) was purified by chromatography on SiO$_2$ (acetone:hexanes, 1:2) to give 9l (0.011 g, 8%) as a yellow solid: Mp 225-226° C.; IR (ATR) $v_{max}$ 3191, 3100, 1732, 1678, 1615, 1571, 1428, 1237, 1166, 812, 794, 760, 751, 721 cm$^{-1}$; $^1$H NMR (400 MHz, DMSO-d$_6$) δ 11.89 (brs, 1H), 11.65 (s, 1H), 8.06-7.99 (m, 2H), 7.56-7.40 (m, 2H), 7.35 (t, J=7.0 Hz 1H); $^{13}$C NMR (100 MHz, DMSO-d$_6$) δ 160.0, 158.5 (d, $J_{C-F}$=248.0 Hz), 157.8, 153.4, 142.9 (d, $J_{C-F}$=6.0 Hz), 141.6 (d, $J_{C-F}$=3.0 Hz), 140.0, 131.4 (d, $J_{C-F}$=9.0 Hz), 129.2, 125.5 (d, $J_{C-F}$=3.0 Hz), 124.6 (d, $J_{C-F}$=4.0 Hz), 119.6 (d, $J_{C-F}$=12.0 Hz), 116.6 (d, $J_{C-F}$=22.0 Hz); $^{19}$F NMR (376 MHz, DMSO-d$_6$) δ −112.7; HRMS (ESI$^+$) m/z calcd for C$_{13}$H$_8$N$_2$O$_2$SF (M+H) 275.0285, found 275.0283.

2-(4-Chloro-3-fluorophenyl)-7-iminothieno[3,2-c]pyridine-4,6(5H,7H)-dione (9m). According to general procedure F, the product obtained from 2-(4-chloro-3-fluorophenyl)-7-nitrothieno-[3,2-c]pyridin-4(5H)-one (8m, 0.155 g, 0.477 mmol) was purified by chromatography on SiO$_2$ (acetone:hexanes, 1:2) to give 9m (0.027 g, 18%) as a yellow solid: Mp>250° C.; IR (ATR) $v_{max}$ 3184, 1731, 1678, 1611, 1467, 1429, 1419, 1306, 1226, 1155, 1068, 961, 865, 808, 781 cm$^{-1}$; $^1$H NMR (400 MHz, DMSO-d$_6$) δ 11.89 (s, 1H), 11.67 (s, 1H), 8.13 (s, 1H), 8.07 (dd, J=10.6, 1.6 Hz, 1H), 7.76-7.67 (m, 2H); $^{13}$C NMR (75 MHz, DMSO-d$_6$) δ 159.9, 157.7, 157.5 (d, $J_{C-F}$=245.2 Hz), 153.4, 146.4 (d, $J_{C-F}$ 3.0 Hz), 142.8, 136.7, 133.0 (d, $J_{C-F}$=7.5 Hz), 131.5, 123.8, 123.4 (d, $J_{C-F}$=3.7 Hz), 120.3 (d, $J_{C-F}$=17.2 Hz), 114.5 (d, $J_{C-F}$=22.5 Hz); $^{19}$F NMR (376 MHz, DMSO-d$_6$) δ −114.9; HRMS (ESI$^+$) m/z calcd for C$_{13}$H$_7$N$_2$O$_2$SClF (M+H) 308.9895, found 308.9895.

2-(3-Chloro-4-fluorophenyl)-7-iminothieno[3,2-c]pyridine-4,6(5H,7H)-dione (9n). According to general procedure F, the product obtained from 2-(3-chloro-4-fluorophenyl)-7-nitrothieno-[3,2-c]pyridin-4(5H)-one (8n, 0.180 g, 0.554 mmol) was purified by chromatography on SiO$_2$ (acetone:hexanes, 1:2) to give 9n (0.036 g, 21%) as a yellow solid: Mp 235-236° C.; IR (ATR) $v_{max}$ 3223, 2997, 2823, 1710, 1605, 1501, 1461, 1434, 1374, 1235, 1185, 1155, 908, 855, 820, 775, 734 cm$^{-1}$; $^1$H NMR (500 MHz, DMSO-d$_6$) δ 11.87 (s, 1H), 11.64 (s, 1H), 8.19 (d, J=7.0 Hz, 1H), 8.07 (s, 1H), 7.90-7.87 (m, 1H), 7.53 (t, J=9.0 Hz, 1H); $^{13}$C NMR (75 MHz, DMSO-d$_6$) δ 159.9, 157.7, 157.6 (d, $J_{C-F}$=248.2 Hz), 153.3, 146.4, 142.5, 136.7, 129.8 (d, $J_{C-F}$=3.7 Hz), 128.2, 127.0 (d, $J_{C-F}$=7.5 Hz), 123.4, 120.7 (d, $J_{C-F}$=18.0 Hz), 117.8 (d, $J_{C-F}$=21.0 Hz); $^{19}$F NMR (470 MHz, DMSO-d$_6$) δ −114.9; HRMS (ESI$^+$) m/z calcd for C$_{13}$H$_7$N$_2$O$_2$SClF (M+H) 308.9895, found 308.9895.

7-Imino-2-(4-(2-morpholinoethoxy)phenyl)thieno[3,2-c]pyridine-4,6(5H,7H)-dione (9o). According to general procedure F, the product obtained from 2-(4-(2-morpholinoethoxy)phenyl-7-nitrothieno[3,2-c]pyrdin-4(5H)-one (8o, 0.125 g, 0.311 mmol) was purified by chromatography on SiO$_2$ (acetone:hexanes, 1:1) to give 9o (0.028 g, 23%) as a brown solid: Mp>250° C.; IR (ATR) $v_{max}$ 3212, 3084, 2927, 2835, 1693, 1601, 1460, 1437, 1290, 1254, 1180, 1149, 1107, 824, 800, 777 cm$^{-1}$; $^1$H NMR (300 MHz, DMSO-d$_6$) δ 11.82 (brs, 1H), 11.49 (s, 1H), 7.84 (s, 1H), 7.79 (d, J=8.7 Hz, 2H), 7.05 (d, J=9.0 Hz, 2H), 4.16 (t, J=5.7 Hz, 2H), 3.60-3.56 (m, 4H), 2.71 (t, J=5.7 Hz, 2H), 2.51-2.46 (m, 4H covered in part by DMSO signal); $^{13}$C NMR (100 MHz, DMSO-d$_6$) δ 160.1, 159.6, 157.9, 153.3, 149.6, 140.7, 136.9, 127.7, 124.6, 120.7, 115.3, 66.2, 65.6, 56.9, 53.6; HRMS (ESI$^+$) m/z calcd for C$_{19}$H$_{20}$N$_3$O$_4$S (M+H) 386.1169, found 386.1162.

5-Methyl-7-nitro-2-phenylthieno[3,2-c]pyridin-4(5H)-one (38). A solution of 8p (0.200 g, 0.735 mmol) and K$_2$CO$_3$ (0.507 g, 3.67 mmol) in DMF (9 mL) was treated dropwise with iodomethane (0.23 mL, 3.7 mmol). The reaction mixture was stirred at 90° C. for 2 d, quenched with saturated aqueous NH$_4$Cl (5 mL) and stirred for 5 min. The mixture was diluted with EtOAc (100 mL). The layers were separated, and the organic layer was washed with H$_2$O (5×5 mL) and saturated aqueous NaCl (2×5 mL), dried (MgSO$_4$) and purified by chromatography on SiO$_2$ (dry-load, EtOAc:hexanes, 1:1) to yield 38 (0.146 g, 69%) as a yellow solid: Mp>250° C.; IR (ATR) $v_{max}$ 3079, 1655, 1603, 1482, 1296, 1256, 1075, 1044, 879 cm$^{-1}$; $^1$H NMR (400 MHz, DMSO-d$_6$) δ 9.31 (s, 1H), 8.00 (s, 1H), 7.86 (d, J=7.6 Hz, 2H), 7.48 (t, J=8.4 Hz, 2H), 7.41 (t, J=7.2 Hz, 1H), 3.69 (s, 3H); $^{13}$C NMR (75 MHz, DMSO-d$_6$) δ 157.7, 144.9, 139.6, 137.8, 132.3, 129.4, 128.9, 128.8, 126.5, 126.0, 120.1, 37.5; HRMS (ESI$^+$) m/z calcd for C$_{14}$H$_{11}$O$_3$N$_2$S (M+H) 287.0483, found, 287.0485.

7-Imino-5-methyl-2-phenylthieno[3,2-c]pyridine-4,6(5H,7H)-dione (9p). According to general procedure F, the product obtained from 5-methyl-7-nitro-2-phenylthieno[3,2-c]pyridin-4(5H)-one (38, 0.120 g, 0.419 mmol) was purified by chromatography on SiO$_2$ (acetone:hexanes, 1:2) to give 9p (0.025 g, 22%) as a brown solid: Mp 236-237° C.; IR (ATR) $v_{max}$ 3234, 3100, 1711, 1670, 1606, 1455, 1432, 1329, 1281, 1183, 1105, 878 cm$^{-1}$; $^1$H NMR (300 MHz, DMSO-d$_6$) δ 11.69 (s, 1H), 8.03 (s, 1H), 7.90-7.77 (m, 2H), 7.53-7.45 (m, 3H), 3.23 (s, 3H); $^{13}$C NMR (75 MHz, DMSO-d$_6$) δ 159.6, 157.9, 152.4, 149.1, 140.7, 136.5, 131.9, 129.6, 129.4, 126.2, 122.5, 27.0; HRMS (ESI$^+$) m/z calcd for C$_{14}$H$_{11}$O$_2$N$_2$S (M+H) 271.0534, found, 271.0536.

5-(Cyclopropylmethyl)-7-nitro-2-phenylthieno[3,2-c]pyridin-4(5H)-one (39). A solution of 7-nitro-2-phenylthieno[3,2-c]pyridin-4(5H)-one (8p, 0.220 g, 0.727 mmol) in THF (15 mL) was treated with cyclopropane methanol (0.0770 mL, 0.945 mmol) and PPh$_3$ (0.250 g, 0.0945 mmol), cooled to 0° C., and treated dropwise with DIAD (0.187 mL, 0.945 mmol). The reaction mixture was warmed to room temperature, stirred for 20 h, diluted with MeOH (15 mL), concentrated to ¼ volume in vacuo, cooled to 0° C., and filtered. The precipitate was dried to afford 39 (0.130 g, 55%) as a yellow solid: Mp 229-231° C.; IR (ATR) $v_{max}$ 3087, 1654, 1595, 1514, 1484, 1449, 1333, 1304, 1230, 1137, 1025 cm$^{-1}$; $^1$H NMR (300 MHz, DMSO-d$_6$) δ 9.08 (s, 1H), 8.03 (s, 1H), 7.95 (dd, J=8.4, 1.2 Hz, 2H), 7.55-7.43 (m, 3H), 4.50 (d, J=7.2 Hz, 2H), 1.45-1.36 (m, 1H), 0.67-0.62 (m, 2H), 0.47-0.45 (m, 2H); $^{13}$C NMR (125 MHz) δ 157.3, 145.0, 138.2, 137.7, 132.2, 129.3, 129.2, 128.9, 126.8, 126.0, 120.2, 53.4, 10.7, 3.5; HRMS (ESI$^+$) m/z calcd for C$_{17}$H$_{14}$O$_3$N$_2$S (M+H) 327.0798, found 327.0794.

5-(Cyclopropylmethyl)-7-imino-2-phenylthieno[3,2-c]pyridine-4,6(5H,7H)-dione (9q). According to general procedure F, the product obtained from 5-(cyclopropylmethyl)-7-nitro-2-phenylthieno[3,2-c]pyridin-4(5H)-one (39, 0.125 g, 0.383 mmol) was purified by chromatography on SiO2 (CH$_2$Cl$_2$) to give 9q (0.066 g, 56%) as a yellow solid: Mp 193-194° C.; IR (ATR) $v_{max}$ 3219, 3099, 1713, 1667, 1605, 1453, 1427, 1334, 1298, 1176, 878, 830, 752, 687 cm-1; 1H NMR (500 MHz, DMSO-d6) δ 11.75 (s, 1H), 8.04 (s, 1H), 7.89 (dd, J=8.4, 1.5 Hz, 2H), 7.52-7.45 (m, 3H), 3.74 (d, J=7.0 Hz, 2H), 1.19-1.10 (m, 1H), 0.48-0.46 (m, 2H), 0.36-0.33 (m, 2H); 13C NMR (125 MHz) δ 159.5, 157.7, 152.3, 149.2, 140.9, 136.3, 131.8, 129.6, 129.4, 126.2, 122.5, 44.5, 9.7, 3.7; HRMS (ESI+) m/z calcd for C17H15O2N2S (M+H) 311.0849, found 311.0847.

N-(4-oxo-2-phenyl-4,5-dihydrothieno[3,2-c]pyridin-7-yl) acetamide (40). Through a suspension of 10% Pd/C (15 mol %) and 7-nitro-2-phenylthieno[3,2-c]pyridin-4(5H)-one (8p, 0.200 g, 0.735 mmol) in MeOH (18 mL, $N_2$ sparged) was bubbled $H_2$ gas for 10 min. The reaction mixture was stirred at room temperature under an atmosphere of $H_2$ (1 atm, balloon) for 6 h and filtered through Celite. The Celite pad was washed with MeOH (50 mL). The Pd/C layer was removed from the Celite, heated at reflux in PhMe (40 mL), filtered over Celite, and eluted with MeOH. This procedure was performed twice. The combined filtrates were concentrated under reduced pressure to afford a brown solid that was dissolved in $Ac_2O$ (7 mL) and THF (7 mL), and stirred at room temperature in the dark for 16 h. The reaction mixture was concentrated under reduced pressure. Purification by chromatography on $SiO_2$ (dry-load, MeOH:EtOAc, 1:9) provided 40 (0.130 g, 62%) as a beige solid: Mp>250° C.; IR (ATR) $v_{max}$ 3253, 3160, 3054, 2972, 2938, 2809, 1652, 1617, 1508, 1384, 1374, 1291, 1145, 1035, 1012, 976, 947, 871, 803, 751, 687; 1H NMR (500 MHz, DMSO-d6) δ 11.46 (brs, 1H), 9.71 (s, 1H), 7.87 (s, 1H), 7.76 (d, J=7.5 Hz, 2H), 7.46 (t, J=6.9 Hz, 2H), 7.36 (t, J=7.2 Hz, 1H), 7.30 (s, 1H), 2.06 (s, 3H); 13C NMR (125 MHz, DMSO-d6) δ 169.0, 157.4, 146.0, 141.5, 132.8, 130.9, 129.3, 128.4, 125.7, 120.3, 113.8 22.8; HRMS (ESI+) m/z calcd for C15H13O2N2S (M+H) 285.0692, found 285.0690.

6,7-Dihydrothieno[3,2-c]pyridin-4(5H)-one (12). A solution of thiophene-2-ethylamine (11, 10.0 mL, 84.5 mmol) in $CH_2Cl_2$ (30 mL) was added slowly over 10 min to a solution of triphosgene (9.58 g, 32.1 mmol) in $CH_2Cl_2$ (150 mL) in a three neck 1-L round-bottom flask ($N_2$ inlet, glass stopper, an outlet connected to an aqueous $NH_4OH$ trap) at 0° C. under $N_2$. Then, saturated aqueous $NaHCO_3$ (180 mL) was added to the reaction mixture and the resulting biphasic mixture was stirred vigorously at 0° C. (ice-bath) under $N_2$ for 2.5 h. The organic layer was dried ($MgSO_4$), filtered, and concentrated to provide a crude product as a dark yellow oil. IR showed the presence of an isocyanate peak at 2259 $cm^{-1}$. A solution of this material (13.0 g, 84.6 mmol) in $CH_2Cl_2$ (150 mL) was added dropwise by addition funnel (2-3 drops per second) over 2 h to a mixture of ferric chloride (14.4 g, 88.8 mmol) in $CH_2Cl_2$ (450 mL) under $N_2$ at 50° C. in a flask connected to a reflux condenser. After an additional 2 h, the mixture was cooled to 0° C. (ice-bath) and diluted with aqueous citric acid (30 g of citric acid monohydrate in 250 mL of $H_2O$), and the resulting biphasic mixture was stirred for 15 min. The two layers were separated and the aqueous layer was extracted with $CH_2Cl_2$ (100 mL). The combined organic layers were washed with saturated aqueous NaCl (350 mL), dried ($MgSO_4$), and concentrated to a dark oil. Purification by chromatography on basic $Al_2O_3$ ($CH_2Cl_2$ to load the sample, elution with MeOH:$CH_2Cl_2$, 1:19) provided 12 (9.90 g, 73% over two steps) as a brown liquid: 1H NMR (500 MHz, CDCl3) δ 7.43 (d, J=5.5 Hz, 1H), 7.11 (d, J=5.5 Hz, 1H), 5.57 (brs, 1H), 3.65 (dt, J=6.5, 2.5 Hz, 2H), 3.08 (t, J=6.5 Hz, 2H). Spectral data were consistent with literature properties.[20]

2-Bromo-6,7-dihydrothieno[3,2-c]pyridin-4(5H)-one (41). In a 250-mL round-bottom flask, a solution of 12 (4.80 g, 31.3 mmol) in AcOH (60 mL) was treated with $Br_2$ (1.77 mL, 34.5 mmol). The red reaction mixture was shielded from light with foil and stirred at room temperature. Reaction progress was monitored by LC-MS. Additional $Br_2$ (1.00 mL) was added every 24 h until starting material was consumed. The reaction mixture was diluted with PhMe (250 mL) and concentrated. The resulting brown solid was dissolved in $CH_2Cl_2$ (300 mL), washed with saturated aqueous $NaHCO_3$ (100 mL), 1 M $Na_2S_2O_3$ (100 mL), and saturated aqueous NaCl (100 mL), dried ($MgSO_4$), and concentrated to give a crude tan solid that was purified by chromatography on $SiO_2$ ($CH_2Cl_2$ to load sample, EtOAc: hexanes, 4:1 to 1:0) to provide 41 (4.70 g, 65%) as a tan solid: 1H NMR (500 MHz, CDCl3) δ 7.38 (s, 1H), 5.69 (brs, 1H), 3.64 (dt, J=6.8, 2.8 Hz, 2H), 2.99 (t, J=6.8 Hz, 2H). Spectral data were consistent with literature properties.[20]

2-Phenyl-6,7-dihydrothieno[3,2-c]pyridin-4(5H)-one (13). To a 1-L round-bottom flask containing Pd(PPh3)4(1.72 g, 1.64 mmol,) were added 41 (9.77 g, 42.1 mmol), phenylboronic acid (6.28 g, 50.5 mmol), and $Na_2CO_3$ (10.3 g, 96.8 mmol). The flask was evacuated and purged with $N_2$ (3×), diluted with deoxygenated dioxane and $H_2O$ (2:1, 420 mL), fitted with a reflux condenser, and heated to 90° C. for 15 h. The resulting dark mixture was cooled to room temperature, diluted with $H_2O$ (1 L), cooled in an ice-bath, and filtered. The brown residue was washed with cold $H_2O$ (2×100 mL) and dissolved in EtOAc. The $H_2O$ washes were extracted with $CH_2Cl_2$(2×50 mL), and the combined organic layers were dried ($MgSO_4$), filtered, concentrated, and dried under high vacuum to afford a black solid that was purified by chromatography on $SiO_2$ ($CH_2Cl_2$ to load sample, EtOAc: hexanes, 1:1 to 1:0) to provide 13 (9.58 g, 99%) as a tan solid: 1H NMR (300 MHz, CDCl3) δ 7.59 (s, 1H), 7.58 (d, J=5.1 Hz, 2H), 7.38 (tt, J=9.0, 1.2 Hz, 2H), 7.33-7.29 (m, 1H), 5.65 (brs, 1H), 3.67 (dt, J=6.8, 2.8 Hz, 2H), 3.09 (t, J=6.8 Hz, 2H). Spectral data were consistent with literature properties.[20]

2-Phenylthieno[3,2-c]pyridin-4(5H)-one (42). In a 500-mL round-bottom flask equipped with a condenser, a solution of 13 (9.58 g, 41.8 mmol) and DDQ (19.0 g, 83.6 mmol) in 1,4-dioxane (260 mL) was stirred at 100° C. for 36 h. The reaction mixture was cooled to room temperature, concentrated, diluted with EtOAc (300 mL), saturated aqueous $NaHCO_3$ and $H_2O$ (4:1, 500 mL), and stirred for 24 h. The organic layer was washed with saturated aqueous $NaHCO_3$ (3×100 mL) and saturated aqueous NaCl (100 mL), dried ($MgSO_4$), filtered, and concentrated give a light brown solid. Acetone was added to the solid to yield a black solution with a tan precipitate. The mixture was sonicated and filtered. The filtrate was concentrated, the process was repeated, and the precipitates were combined to provide 42 as a tan solid (2.88 g). The aqueous phase was extracted with $CH_2Cl_2$ until the suspended solid was no longer present. The combined $CH_2Cl_2$ washes were dried ($MgSO_4$), filtered, and concentrated to provide additional 42 (4.94 g; combined yield: 7.82 g, 82%) as a tan solid: 1H NMR (300 MHz, DMSO-$d_6$) δ 11.46 (s, 1H), 7.85 (s, 1H), 7.75 (d, J=7.2 Hz, 2H), 7.45 (t, J=7.2 Hz, 2H), 7.38-7.34 (m, 1H), 7.26 (dd, J=6.6, 5.4 Hz, 1H), 6.85 (d, J=7.2 Hz, 1H). Spectral data were consistent with literature properties.[20]

7-Nitro-2-phenylthieno[3,2-c]pyridin-4(5H)-one (8p). To a 1-L round-bottom flask charged with a stir bar were added 42 (2.80 g, 12.3 mmol), MeCN (246 mL) and t-BuONO (6.51 mL, 49.3 mmol), and the flask was flushed with $O_2$ and stirred at room temperature under $O_2$ (1 atm, balloon, 10 min flush) for 24 h. Reaction progress was monitored by TLC analysis (50% EtOAc:hexanes, $R_f$=0.70). The solution was partially concentrated (ca. ¼ volume). The resulting slurry was cooled in an ice bath for 20 min and filtered. The precipitate was washed with MeOH (3×5 mL) and dried under high vacuum to provide 8p (1.78 g, 53%) as a yellow-brown solid: 1H NMR (300 MHz, DMSO-$d_6$) δ 12.76 (brs, 1H), 8.74 (d, J=6.9 Hz, 1H), 7.98 (s, 1H), 7.85

(dt, J=6.9, 1.5 Hz, 2H), 7.52-7.41 (m, 3H). Spectral data were consistent with literature properties.[20]

7-Imino-2-phenylthieno[3,2-c]pyridine-4,6(5H,7H)-dione (2). A suspension of 8p (1.00 g, 3.67 mmol) in MeOH (90 mL) was bubbled with $N_2$ for 5 min, and then treated with 10% Pd/C (0.597 g, 0.551 mmol). The reaction mixture was bubbled with $H_2$ for 10 min, stirred at room temperature under a $H_2$ atmosphere (1 atm, balloon) for 16 h, and filtered through Celite. The Celite pad was washed with MeOH (100 mL). The Pd/C layer was removed from the Celite, boiled in PhMe (40 mL), filtered over Celite, and eluted with MeOH. This procedure was performed twice. The combined filtrates were concentrated under reduced pressure to afford a brown solid that was dissolved in MeOH (2 L). The solution was passed through the tubing at a rate of 1.9 mL/min using the peristaltic pump (5 RPM) under LED irradiation. The tubing was flushed with MeOH (40 mL). The mixture was concentrated to give a brown solid that was filtered through a short $SiO_2$ plug (dry load, $MeCN:CH_2Cl_2$, 1:6) to provide the imine/ketone mixture as a dark orange solid (0.634 g, 2.47 mmol). A solution of this mixture and $NH_4OAc$ (3.81 g, 49.5 mmol) in MeOH (180 mL) in an oven-dried pressure vessel was stirred at 60-65° C. Due to residual solid still present after 24 h, the solution was decanted and additional MeOH (180 mL) and $NH_4OAc$ (3.81 g, 49.5) were added. The reaction mixture was stirred for an additional 24 h. The process was repeated until the solution was homogeneous. The reaction mixture was cooled to room temperature and concentrated. The solid residue was suspended in EtOAc (300 mL) and saturated aqueous $NaHCO_3$ (150 mL), and vigorously stirred until all solids dissolved. The layers were separated, and the aqueous layer was extracted with EtOAc (2×50 mL). The combined organic layers were washed with $H_2O$ (2×50 mL) and concentrated to provide 2 (0.634 g, 67% over three steps) as a reddish-brown solid: $^1$H NMR (300 MHz, DMSO-$d_6$) δ 11.86 (s, 1H), 11.59 (s, 1H), 7.98 (s, 1H), 7.88 (dd, J=8.1, 1.5 Hz, 2H), 7.53-7.44 (m, 3H). Spectral data were consistent with literature properties.[20]

4-Nitroisoquinolin-1(2H)-one (14). To a solution of 1-hydroxyisoquinoline (2.00 g, 13.5 mmol) in AcOH (13.5 mL) was added $HNO_3$ (2.68 mL, 40.5 mmol). The solution was stirred at room temperature for 5 min, then heated to 65° C. for 16 h in a round-bottom flask equipped with a reflux condenser. The reaction mixture was poured over ice and filtered. The residue was washed with ice-cold $H_2O$ (2×5 mL) and dried under high vacuum to provide 14 (1.53 g, 59%) as a yellow solid: Mp 236-237° C.; IR (ATR) $v_{max}$ 3061, 2864, 1655, 1631, 1509, 1470, 1439, 1317, 1285, 1225, 1139, 1039 cm$^{-1}$; $^1$H NMR (300 MHz, DMSO-$d_6$) δ 12.42 (brs, 1H), 8.64 (d, J=6.3 Hz, 1H), 8.57 (dd, J=7.2, 0.3 Hz, 1H), 8.31 (ddd, J=8.1, 1.5, 0.6 Hz, 1H), 7.94 (td, J=7.2, 1.5 Hz, 1H), 7.68 (td, J=7.2, 0.9 Hz, 1H); $^{13}$C NMR (75 MHz, DMSO-$d_6$) δ 161.4, 136.2, 134.3, 129.4, 128.2, 128.0, 127.7, 124.2, 123.1; HRMS (ESI$^+$) m/z calcd for $C_9H_7O_3N_2$ (M+H) 191.0451, found, 191.0451.

Isoquinoline-1,3,4(2H)-trione (15). A suspension of 14 (0.200 g, 1.05 mmol) in EtOH:EtOAc (8 mL, 1:1) was bubbled with $N_2$ for 10 min before adding 10% Pd/C (0.171 g, 0.158 mmol). Then, $H_2$ was bubbled through the mixture for 5 min. The solution was stirred at room temperature under $H_2$ (1 atm, balloon) for 24 h and filtered over Celite. The Celite pad was washed consecutively with PhMe and MeOH until colored material stopped eluting. The filtrate was concentrated to give a solid that was dissolved in in MeOH (400 mL) and treated with methylene blue (0.010 g, 0.032 mmol). The solution was passed through the tubing under at a rate of 1.9 mL/min using the peristaltic pump (5 RPM) under LED irradiation. The tubing was flushed with MeOH (50 mL). The reaction mixture was concentrated to give a blue solid which was purified by chromatography on $SiO_2$ (dry load, EtOAc:hexanes, 1:2.5) to give 15 (0.032 g, 17%) as a green solid: Mp 226-228° C.; IR (ATR) $v_{max}$ 3194, 3114, 2923, 1685, 1589, 1332, 1272, 1129, 974, 823, 794 cm$^{-1}$; $^1$H NMR (300 MHz, DMSO-$d_6$) δ 11.94 (brs, 1H), 8.13 (dd, J=8.4, 1.2 Hz, 1H), 8.05 (dd, J=7.2, 1.2, Hz, 1H), 7.95-7.85 (m, 2H); $^{13}$C NMR (75 MHz, DMSO-$d_6$) δ 175.5, 163.2, 157.5, 134.9, 134.0, 132.3, 129.8, 128.1, 126.7; HRMS (ESI$^-$) m/z calcd for $C_9H_4O_3N$ (M–H) 174.0192, found, 174.0186.

5-Bromothiophene-3-carbaldehyde (43). To a solution of thiophene-3-carbaldehyde (2.00 mL, 22.1 mmol) in $CH_2Cl_2$ (80 mL) was added $AlCl_3$ (8.86 g, 66.4 mmol). The dark solution was stirred for 10 min, and $Br_2$ (1.25 mL, 24.4 mmol) was added. The mixture was stirred at room temperature for 12 h, and slowly quenched with $H_2O$ at 0° C. The aqueous phase was extracted with $CH_2Cl_2$ (2×30 mL). The combined organic phases were washed with saturated aqueous $Na_2S_2O_3$ (30 mL) and saturated aqueous NaCl (30 mL), dried (MgSO$_4$), and concentrated. The dark oil was purified by chromatography on $SiO_2$ (EtOAc:hexanes, 1:19) to provide 43 (2.85 g, 67%) as a yellow liquid: $^1$H NMR (300 MHz, CDCl$_3$) δ 9.77 (s, 1H), 7.99 (d, J=1.5 Hz, 1H), 7.50 (d, J=1.2 Hz, 1H). Spectral data were consistent with literature properties.[40]

(E)-3-(5-Bromothiophen-3-yl)acrylic acid (44). To a solution of 43 (3.39 g, 17.7 mmol) in a round-bottom flask equipped with a reflux condenser were added pyridine (40 mL) and malonic acid (5.59 g, 53.2 mmol). At 110° C., piperidine (0.88 mL, 8.9 mmol) was added. After 3 h (reaction progress was monitored by TLC, EtOAc:hexanes, 1:9), the reaction mixture was concentrated, diluted with $H_2O$ (45 mL), and neutralized with 6 M HCl to pH 2. The precipitate was filtered, washed with $H_2O$ (3×10 mL), and dissolved in MeOH. This solution was concentrated and dried under high vacuum to provide 44 (2.35 g, 57%) as a tan solid: $^1$H NMR (300 MHz, CDCl$_3$) δ 12.34 (brs, 1H), 7.93 (d, J=1.5 Hz, 1H), 7.71 (d, J=1.5 Hz, 1H), 7.48 (d, J=15.9 Hz, 1H), 6.37 (d, J=15.9 Hz, 1H). Spectral data were consistent with literature properties.[37]

2-Bromothieno[2,3-c]pyridin-7(6H)-one (45). A solution of Et$_3$N (2.81 mL, 20.2 mmol) and 44 (2.35 g, 10.1 mmol) in acetone (21 mL) was treated at 0° C. with ethyl chloroformate (2.94 mL, 30.2 mmol). The reaction mixture was stirred at 0° C. for 1 h. A solution of NaN$_3$ (0.983 g, 15.1 mmol) in $H_2O$ (6 mL) was added slowly at 0° C., and stirring was continued at 0° C. for 1 h. The mixture was poured into ice-cold $H_2O$, extracted with EtOAc, dried (MgSO$_4$), and concentrated to give the crude azide intermediate as a tan solid. To a solution of Bu$_3$N (3.15 mL, 13.1 mmol) in Ph$_2$O (10 mL) heated to 240° C. was added a solution of the crude azide (2.60 g, 10.1 mmol) in $CH_2Cl_2$ (20.2 mL) over a period of ca. 30 min, allowing the $CH_2Cl_2$ to boil off. The reaction mixture was stirred at 240° C. for another 1 h, cooled to room temperature, diluted with hexanes (70 mL), and stirred for 15 min. The precipitate was filtered, washed with hexanes (2×10 mL) and dried under vacuum to give the crude product as a sticky brown solid. Purification by chromatography on $SiO_2$ ($CH_2Cl_2$ to load sample, EtOAc to elute impurities, then MeOH:EtOAc, 1:9) provided 45 (1.29 g, 56%) as a brown solid: Mp 246-248° C.; IR (ATR) $v_{max}$ 3131.3, 2957.1, 2838.5, 1627.6, 1609.6, 1521.9, 1470.6, 1418.7, 1238.5, 1059.5, 948.3, 935.8, 888.1 cm$^{-1}$; $^1$H NMR (300 MHz, DMSO-$d_6$) δ 11.65 (brs, 1H), 7.57 (s, 1H), 7.29 (d, J=7.2 Hz, 1H), 6.64 (d, J=6.9 Hz, 1H); $^{13}$C NMR (100 MHz, DMSO-d$_6$) δ 157.1, 146.7, 131.4, 130.1, 128.4, 121.0, 101.5; HRMS (ESI$^+$) m/z calcd for C$_7$H$_5$BrNOS (M+H) 229.9275, found, 229.9266.

2-Bromo-4-nitrothieno[2,3-c]pyridin-7(6H)-one (46). To a solution of 45 (1.20 g, 5.21 mmol) in MeCN (104 mL) was added t-BuONO (2.76 mL, 20.9 mmol). The flask was flushed with O$_2$ and the solution was stirred for 15 h at rt under O$_2$ (1 atm, balloon), concentrated, and suspended in MeCN (10 mL). The resulting slurry was filtered and washed with MeCN (3×5 mL) to provide 46 (0.730 g, 51%) as a tan solid: Mp 203-205° C.; IR (ATR) ν$_{max}$ 3189, 3083, 1744, 1700, 1674, 1519, 1430, 1389, 1369, 1260, 880, 867, 821, 797, 746 cm$^{-1}$; $^1$H NMR (300 MHz, DMSO-d$_6$) δ 12.88 (brs, 1H), 8.69 (s, 1H), 8.06 (s, 1H); $^{13}$C NMR (75 MHz, DMSO-d$_6$) δ 157.1, 138.4, 137.3, 130.7, 128.2, 127.5, 124.8; HRMS (ESI$^+$) m z calcd for C$_7$H$_4$BrN$_2$O$_3$S (M+H) 274.9126, found, 274.9106.

4-Nitro-2-phenylthieno[2,3-c]pyridin-7(6H)-one (16). To a 100-mL round-bottom flask containing Pd(PPh$_3$)$_4$(0.134 g, 0.127 mmol) were added 46 (0.700 g, 2.54 mmol), phenylboronic acid (6.28 g, 50.5 mmol), and Na$_2$CO$_3$ (0.623 g, 5.85 mmol). The flask was evacuated and purged with N$_2$ (3×), diluted with deoxygenated dioxane and H$_2$O (2:1, 26 mL), fitted with a reflux condenser, and heated to 90° C. for 16 h. The solution was concentrated to give a red oil that was diluted with H$_2$O (50 mL) and 1 M KHSO$_4$ (5 mL), at which time the red oil converted to an orange semi-solid suspension. The mixture was diluted with EtOAc (40 mL), and the layers were separated. The aqueous phase was extracted with EtOAc (3×100 mL). The combined organic extracts were washed with saturated aqueous NaCl (50 mL), dried (MgSO$_4$), filtered, and concentrated to give a yellow solid. The solid was then partially dissolved in MeOH (15 mL), sonicated, and heated to reflux, cooled to room temperature, and kept in a −20° C. freezer for 30 min. The yellow precipitate was filtered and washed with cold MeOH to give 16 (0.354 g, 52%): Mp>250° C.; IR (ATR) ν$_{max}$ 3308, 1646, 1626, 1530, 1504, 1489, 1459, 1439, 1401, 1348, 1306, 1246, 1153, 1100, 1064, 1025, 998, 964 cm$^{-1}$; $^1$H NMR (300 MHz, DMSO-d$_6$) δ 12.75 (brs, 1H), 8.70 (s, 1H), 8.28 (s, 1H), 7.88 (dd, J=8.1, 1.8 Hz, 2H), 7.57-7.50 (m, 3H); $^{13}$C NMR (75 MHz, DMSO-d$_6$) δ 157.5, 152.6, 138.4, 136.6, 132.0, 130.0, 129.5, 127.9, 127.6, 126.6, 120.0; HRMS (ESI$^+$) m/z calcd for C$_{13}$H$_9$O$_3$N$_2$S (M+H) 273.0328, found, 273.0334.

2-Phenylthieno[2,3-c]pyridine-4,5,7(6H)-trione (17). To a suspension of 16 (0.170 g, 0.468 mmol) in degassed MeOH (10 mL) was added 10% Pd/C (0.076 g, 0.070 mmol). Then, H$_2$ was bubbled through the mixture for 5 min. The suspension was stirred at room temperature under H$_2$ (1 atm, balloon) for 17 h, and filtered over Celite. The Pd/C layer was removed, boiled in PhMe (10 mL) for 10 seconds, filtered over Celite, and washed with MeOH. The process was repeated two more times. The combined filtrates were concentrated under reduced pressure to give a residue that was suspended in MeCN (20 mL) and treated with mesotetraphenylporphine (0.0086 g, 0.014 mmol). The solution was irradiated with two CFL lamps, flushed with O$_2$, and allowed to stir under O$_2$ (1 atm, balloon) for 6 d. The reaction mixture was concentrated and purified by chromatography on SiO$_2$ (dry load, MeCN:CH$_2$Cl$_2$, 0:1 to 1:6) to provide 17 (0.025 g, 21%) as a yellow solid. The reaction was also performed in-flow following the general procedure F with 3% methylene blue to provide 17 (11%) as a yellow solid: Mp>250° C.; IR (ATR) ν$_{max}$ 3079, 2851, 1737, 1701, 1671, 1535, 1502, 1454, 1415, 1360, 1265, 1120, 1078, 998, 954 cm$^{-1}$; $^1$H NMR (300 MHz, DMSO-d$_6$) δ 12.01 (brs, 1H), 8.05 (s, 1H), 7.90 (dd, J=8.1, 2.1 Hz, 2H), 7.53-7.47 (m, 3H); $^{13}$C NMR (75 MHz, DMSO-d$_6$) δ 170.1, 159.0, 158.1, 151.1, 141.6, 140.1, 131.5, 129.9, 129.5, 126.4, 121.3; HRMS (ESI$^+$) m/z calcd for C$_{13}$H$_6$O$_3$NS (M+H) 256.0063, found, 256.0063.

(E)-4-(2-(Dimethylamino)vinyl)nicotinonitrile (47). A solution of 3-cyano-4-methylpyridine (1.00 g, 8.21 mmol) and Bredereck's reagent (2.07 mL, 9.03 mmol) in DMF (12 mL), was heated at 140° C. under N$_2$ in a 20 mL microwave vial for 2 d. After addition of EtOAc (200 mL), the mixture was washed with H$_2$O (5×24 mL). The combined organic layers were washed with saturated aqueous NaCl (10 mL), dried (MgSO$_4$), concentrated, and dried under high vacuum to give 47 (1.27 g, 89%) as a light red solid: $^1$H NMR (300 MHz, DMSO-d$_6$) δ 8.48 (s, 1H), 8.22 (dd, J=6, 0.6 Hz, 1H), 7.83 (d, J=13.2 Hz, 1H), 7.45 (d, J=6 Hz, 1H), 5.05 (d, J=13.2 Hz, 1H), 2.98 (s, 6H). Spectral data were consistent with literature properties.[41,42]

2,7-Naphthyridin-1(2H)-one (48). To a solution of 47 (1.27 g, 7.33 mmol) in AcOH (3.50 mL) was added H$_2$SO$_4$ (3.50 mL). The reaction mixture was stirred at 110° C. for 1 h, cooled to room temperature, diluted with H$_2$O (10 mL), and then slowly added to NH$_4$OH (15 mL). The solution was neutralized to pH 7-8 with additional NH$_4$OH and was cooled in an ice bath. The precipitate was filtered and washed with small amounts of cold H$_2$O (2×3 mL) and dried under high vacuum to afford 48 (0.899 g, 84%) as a tan solid: $^1$H NMR (300 MHz, DMSO-d$_6$) δ 11.61 (brs, 1H), 9.31 (t, J=0.8 Hz, 1H), 8.70 (d, J=5.4 Hz, 1H), 7.59 (dd, J=5.4, 0.8 Hz, 1H), 7.42 (dd, J=6.9, 6.0 Hz, 1H), 6.56 (d, J=7.2 Hz, 1H). Spectral data were consistent with literature properties.[42]

4-Nitro-2,7-naphthyridin-1(2H)-one (18). To a microwave vial charged with a stir bar were added 48 (0.882 g, 6.03 mmol) and H$_2$SO$_4$ (5.50 mL), followed by HNO$_3$ (1.20 mL, 18.1 mmol). The vial was capped and stirred at 85° C. for 16 h. The reaction mixture was cooled to 0° C. (ice-bath), diluted with H$_2$O (10 mL), and basified to pH 7 with NH$_{40}$H. The resulting precipitate was filtered, washed with minimal amounts of cold H$_2$O (2×5 mL), and dried under high vacuum to provide 18 (0.393 g, 34%) as a yellow solid: Mp>250° C.; IR (ATR) ν$_{max}$ 3187, 3130, 3060, 2879, 1677, 1631, 1589, 1509, 1471, 1415, 1348, 1296, 1247, 1204, 1187, 1107, 1038, 895, 790 cm$^{-1}$; $^1$H NMR (300 MHz, DMSO-d$_6$) δ 12.66 (brs, 1H), 9.38 (s, 1H), 8.91 (t, J=5.5 Hz, 2H), 8.41 (d, J=5.5 Hz, 1H); $^{13}$C NMR (75 MHz, DMSO-d$_6$) δ 161.7, 152.9, 150.4, 141.7, 135.5, 125.9, 118.4, 115.9; HRMS (ESI$^+$) m/z calcd for C$_8$H$_6$O$_3$N$_3$(M+H) 191.0403, found, 191.0404.

2,5-Dihydro-1H-pyrido[4,3-b]indol-1-one (49). A solution of 2,4-dihydroxypyridine (0.500 g, 4.41 mmol) and phenylhydrazine (1.49 mL, 14.7 mmol) in Ph$_2$O (3.5 mL) was stirred for 15 h at 240° C. The solution was cooled to room temperature and diluted with hexanes (20 mL), stirred for 15 min, and filtered. The solid was washed with hexanes and collected to give crude 49 as a dark gray solid that was washed with MeOH (2×3 mL) and filtered to provide 49 (0.393 g, 48%) as a black solid: $^1$H NMR (400 MHz, DMSO-d$_6$) δ 11.70 (s, 1H), 11.08 (s, 1H), 8.09 (d, J=7.8 Hz, 1H), 7.48 (d, J=7.8 Hz, 1H), 7.30-7.25 (m, 2H), 7.18 (t, J=7.2 Hz, 1H), 6.50 (d, J=6.9 Hz, 1H). Spectral data were consistent with literature properties.[43]

4-Nitro-2,5-dihydro-1H-pyrido[4,3-b]indol-1-one (19). To a solution of 49 (0.100 g, 0.543 mmol) in MeCN (11 mL) was added t-BuONO (0.287 mL, 2.17 mmol). The flask was flushed with O$_2$, and the solution was stirred for 15 h at room temperature under O$_2$ (1 atm, balloon). The solvent was evaporated, and the orange residue was purified by chromatography on SiO$_2$ (dry load, EtOAc:hexanes, 1:1 to 1.5:1) to provide 19 (0.052 g, 42%) as a yellow-orange powder: Mp>250° C.; IR (ATR) $v_{max}$ 3376, 3013, 2924, 2815, 1630, 1608, 1509, 1250, 1191, 1020 cm$^{-1}$; $^1$H NMR (400 MHz, DMSO-d$_6$) δ 12.41 (brs, 1H), 12.29 (brs, 1H), 8.72 (s, 1H), 8.14 (d, J=7.8 Hz, 1H), 7.72 (d, J=8.1 Hz, 1H), 7.39 (td, J=8.1, 0.9 Hz, 1H), 7.28 (t, J=8.4 Hz, 1H); $^{13}$C NMR (75 MHz, DMSO-d$_6$) δ 159.3, 137.7, 137.1, 135.7, 124.7, 123.3, 122.0, 121.8, 120.3, 112.8, 106.1; HRMS (ESI$^+$) m/z calcd for C$_{11}$H$_8$O$_3$N$_3$(M+H) 230.0559, found, 230.0560.

Synthesis of Compounds of Formula (I)

Compounds according to Formula (I) were readily synthesized in accordance with the procedures and conditions as detailed in Scheme 6 below.

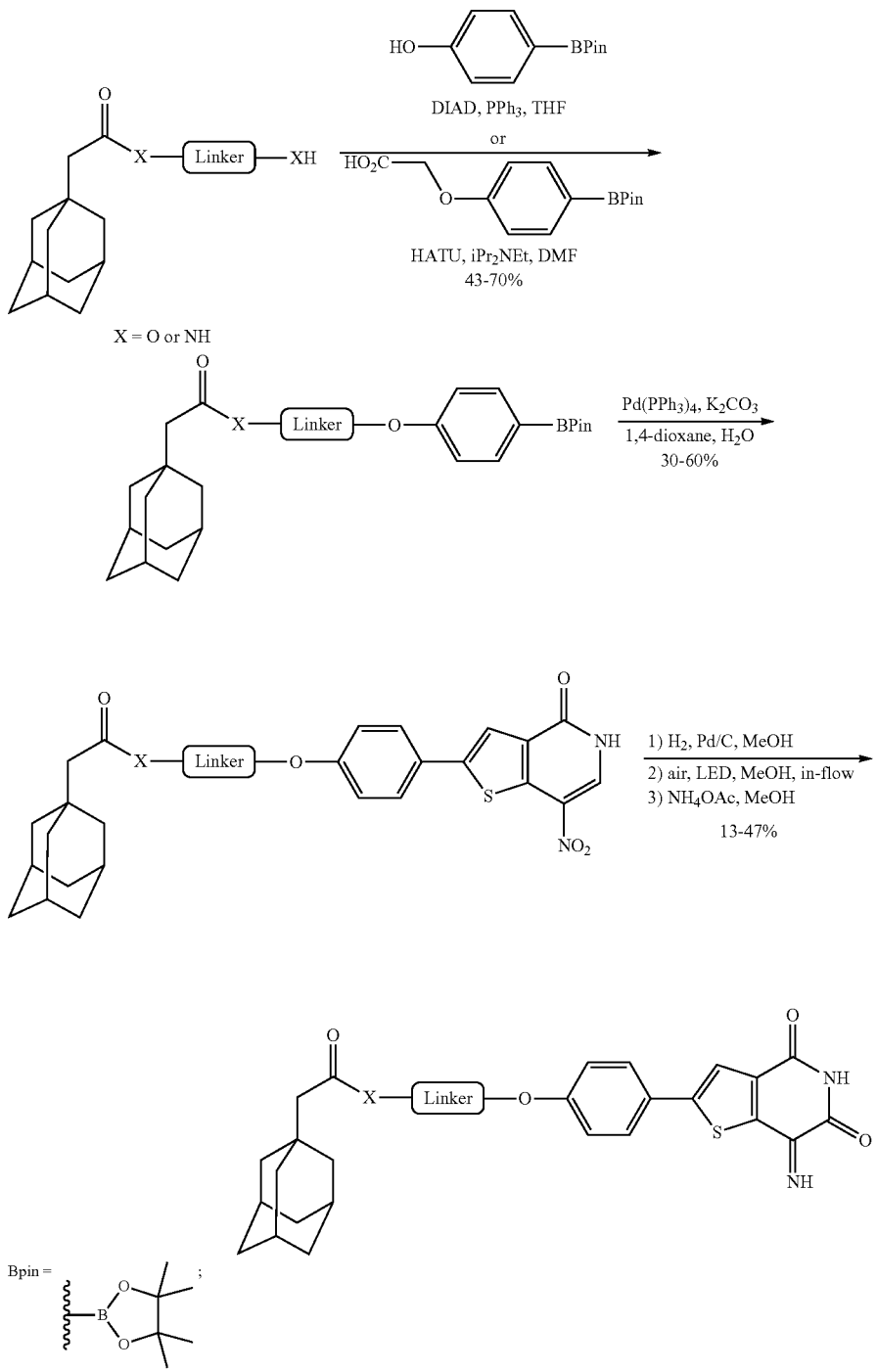

HATU = (1-[Bis(dimethylamino)methylene]-1H-1,2,3-trizolo[4,5-b]pyridinium 3-oxide hexafluorophosphate; and DIAD = Diisopropyl azodicarboxylate.

Final compounds prepared according to Scheme 6 above are as follows:

| Compound | X—[Linker] | Yield (mg) |
|---|---|---|
| EJR-876-34 | ~O~ | 3.23 |
| EJR-876-35 | ~NH~ | 2.98 |
| EJR-887-24 | ~NH-(CH2)3-NH-C(O)-CH2~ | 3.93 |
| EJR-887-35 | ~NH-CH2CH2-O-CH2CH2-O-CH2CH2-NH-C(O)-CH2~ | 3.73 |

In Vitro Testing

Advanced ovarian cancer and triple negative breast cancer respond poorly to existing drugs and, thus, demand new therapies. The protein tyrosine phosphatase PTP4A3 (Phosphatase of Regenerating Liver-3, PRL-3) is overexpressed in these cancer tissues.[19] PTP4A3 also promotes cancer cell migration and invasion, and is believed to be the most oncogenic of all tyrosine phosphatases.[21] Previously, we found that the iminothienopyridone, JMS-053 (2), is a specific, cell active small molecule PTP4A3 inhibitor superior to 1 with an in vitro $IC_{50}$ for PTP4A3 of 30-40 nM.[20,21] However, the limited scope of the batch-photooxygenation method had hampered our efforts to investigate structure-activity relationships (SAR) for this scaffold. We were therefore interested to test the new analogs generated through in-flow photooxygenation in our biochemical potency assay.

Recombinant human PTP4A3 phosphatase was used and the enzymatic assay was performed as previously described,[20] except that it was fully automated using an Agilent Bravo Liquid Handling Platform to increase reproducibility. Results are the mean values of N number of independent assays, each comprising 10-point concentration curves conducted with six replicates (Table 2).

TABLE 2

In vitro inhibition of PTP4A3 phosphatase activity.

| Compound | Structure | $IC_{50}$ (nM) ± SEM | N |
|---|---|---|---|
| 2 | (phenyl-thieno-pyridone with NH imine) | 34.72 ± 2.54 | 6 |
| 3 | (phenyl-thieno-pyridone dione) | 49.47 ± 2.93 | 6 |

TABLE 2-continued

In vitro inhibition of PTP4A3 phosphatase activity.

| Compound | Structure | IC$_{50}$ (nM) ± SEM | N |
|---|---|---|---|
| 15 | 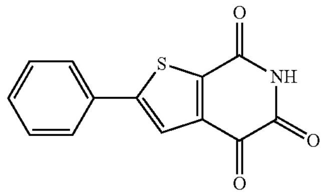 [SMILES: O=C1NC(=O)c2sc(-c3ccccc3)cc2C1=O] | 162.20 ± 14.63 | 3 |
| 9a | 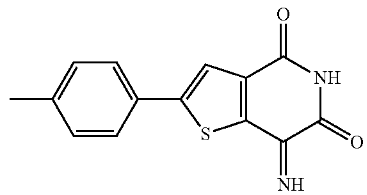 [SMILES: Cc1ccc(-c2cc3c(s2)C(=N)C(=O)NC3=O)cc1] | 61.70 ± 14.23 | 3 |
| 9b | 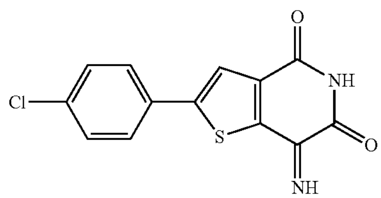 [SMILES: N=C1C(=O)NC(=O)c2cc(-c3ccc(Cl)cc3)sc21] | 41.93 ± 1.15 | 3 |
| 9c | 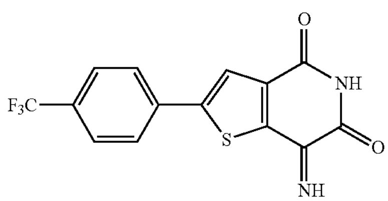 [SMILES: N=C1C(=O)NC(=O)c2cc(-c3ccc(C(F)(F)F)cc3)sc21] | 62.49 ± 2.25 | 3 |
| 9d | 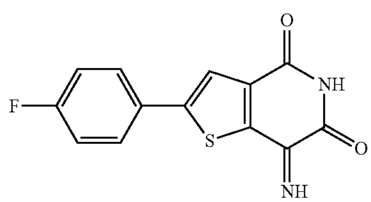 | 71.05 ± 2.54 | 3 |
| 9e | 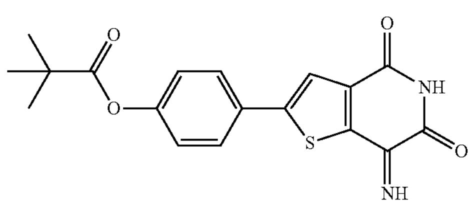 [SMILES: CC(C)(C)C(=O)Oc1ccc(-c2cc3c(s2)C(=N)C(=O)NC3=O)cc1] | 255.90 ± 12.28 | 3 |
| 9f | 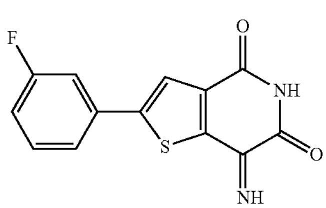 [SMILES: N=C1C(=O)NC(=O)c2cc(-c3cccc(F)c3)sc21] | 39.12 ± 1.31 | 3 |

TABLE 2-continued

In vitro inhibition of PTP4A3 phosphatase activity.

| Compound | Structure | IC$_{50}$ (nM) ± SEM | N |
|---|---|---|---|
| 9g | 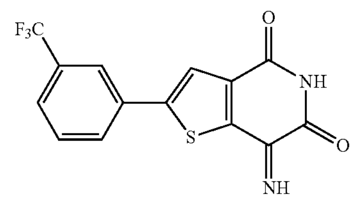 [SMILES: N=C1C(=O)NC(=O)c2cc(-c3cccc(C(F)(F)F)c3)sc21] | 192.80 ± 6.06 | 3 |
| 9h | 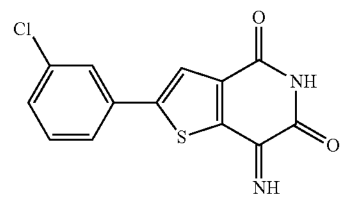 [SMILES: N=C1C(=O)NC(=O)c2cc(-c3cccc(Cl)c3)sc21] | 65.71 ± 4.13 | 6 |
| 9i | 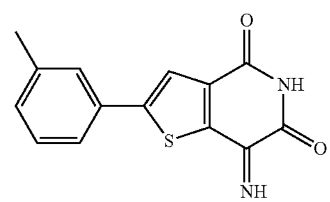 [SMILES: Cc1cccc(-c2cc3c(s2)C(=N)C(=O)NC3=O)c1] | 53.40 ± 1.46 | 3 |
| 9j | 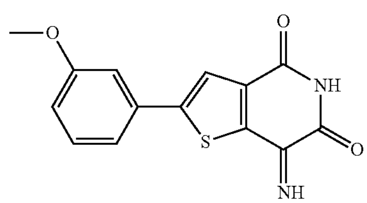 [SMILES: COc1cccc(-c2cc3c(s2)C(=N)C(=O)NC3=O)c1] | 47.65 ± 2.68 | 3 |
| 9k | 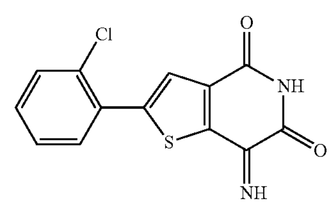 | 36.14 ± 1.43 | 3 |
| 9l | 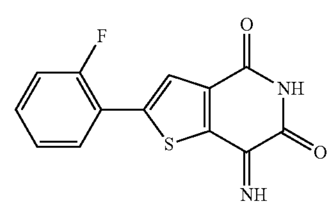 | 53.40 ± 1.46 | 3 |
| 9m | 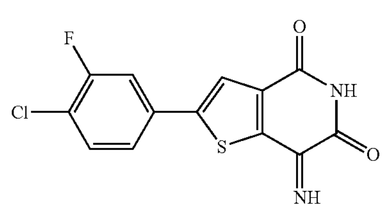 [SMILES: N=C1C(=O)NC(=O)c2cc(-c3ccc(Cl)c(F)c3)sc21] | 47.43 ± 2.40 | 3 |

TABLE 2-continued

In vitro inhibition of PTP4A3 phosphatase activity.

| Compound | Structure | IC$_{50}$ (nM) ± SEM | N |
|---|---|---|---|
| 9n | 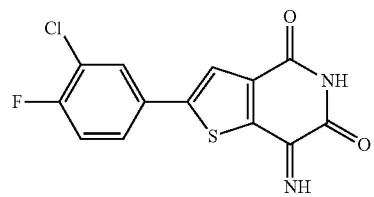 | 67.68 ± 3.00 | 3 |
| 9o | 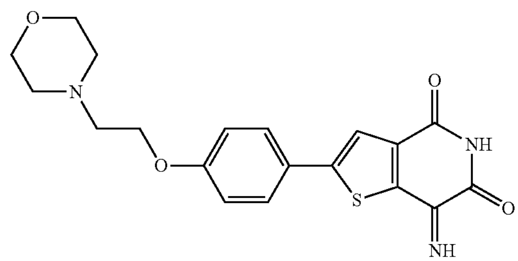 [SMILES: N=C1C(=O)NC(=O)c2cc(-c3ccc(OCCN4CCOCC4)cc3)sc21] | 98.18 ± 2.49 | 6 |
| 9q | 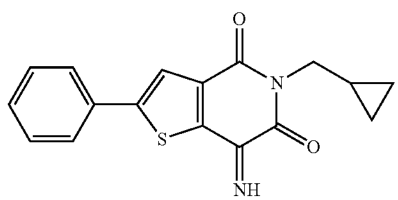 [SMILES: N=C1C(=O)N(CC2CC2)C(=O)c2cc(-c3ccccc3)sc21] | 85.74 ± 5.96 | 3 |
| NRT-892-04 | 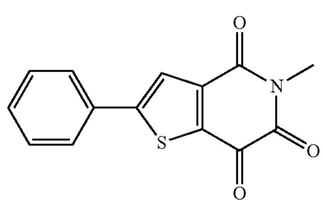 | 32.21 ± 3.52 | 3 |
| 9p | 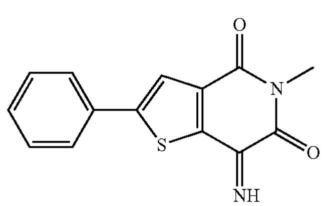 | 48.86 ± 12.00 | 6 |
| EJR-876-34 | 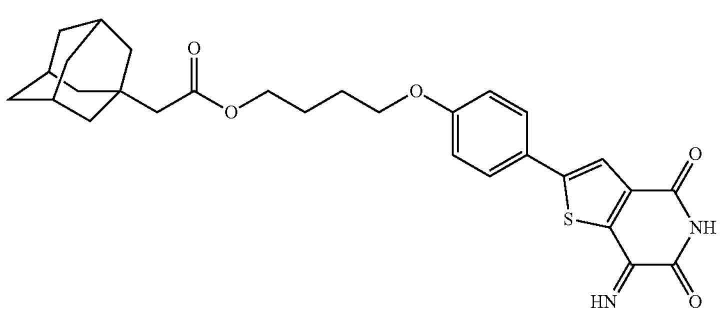 [SMILES: N=C1C(=O)NC(=O)c2cc(-c3ccc(OCCCCOC(=O)CC45CC6CC(CC(C6)C4)C5)cc3)sc21] | 4976.0 ± 311.6 | 3 |

TABLE 2-continued

In vitro inhibition of PTP4A3 phosphatase activity.

| Compound | Structure | $IC_{50}$ (nM) ± SEM | N |
|---|---|---|---|
| EJR-876-35 | 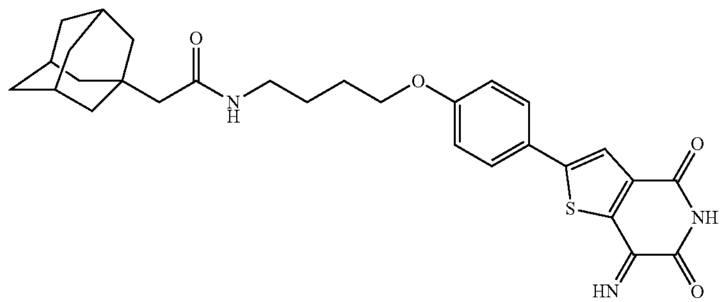 [SMILES: N=C1C(=O)NC(=O)c2cc(-c3ccc(OCCCCNC(=O)CC45CC6CC(CC(C6)C4)C5)cc3)sc21] | 642.90 ± 72.61 | 3 |
| EJR-887-24 | 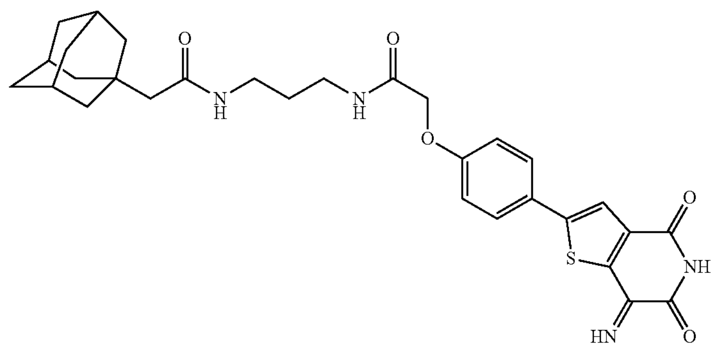 [SMILES: N=C1C(=O)NC(=O)c2cc(-c3ccc(OCC(=O)NCCCNC(=O)CC45CC6CC(CC(C6)C4)C5)cc3)sc21] | 205.50 ± 11.44 | 3 |
| EJR-887-35 | 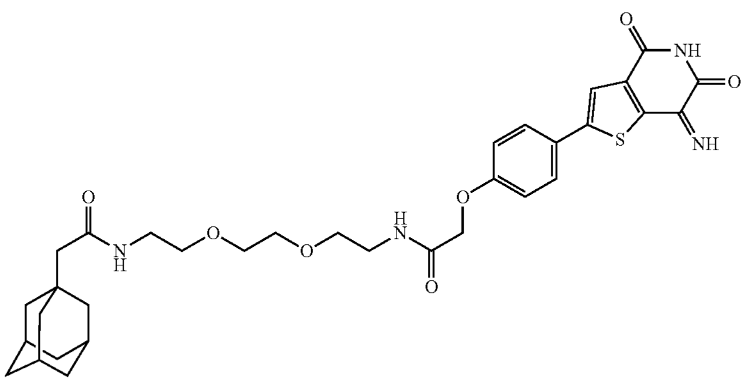 [SMILES: N=C1C(=O)NC(=O)c2cc(-c3ccc(OCC(=O)NCCOCCOCCNC(=O)CC45CC6CC(CC(C6)C4)C5)cc3)sc21] | 107.30 ± 13.54 | 3 |

Cell Assay for EJR-876-35. Viability for leukemia and lymphoma cells was determined after a 48 hour exposure to ten different concentrations using Alamar blue in three independent assays unless otherwise indicated by an asterisk for N=1. Viability for cancer cells grown as a monolayer was determined using the methods of McQueeney et al. (Oncotarget 9:8223-8240, 2017) after a 48-hour exposure to ten different concentrations using Alamar blue in three independent assays unless otherwise indicated by an asterisk for N=1. Viability for spheroid growth was determined using the methods of McQueeney et al. (Oncotarget 9:8223-8240, 2017) after a 48 hour exposure to ten different concentrations using CellTiterGlo 3D in three independent assays unless otherwise indicated by an asterisk (*) for N=1. ND=not determined. Results are shown in Table 3a below.

TABLE 3a

Cell-based activity for EJR-876-35 compared to JMS-053.

| | $EC_{50}$ (mean μM ± SEM) | |
|---|---|---|
| Cell Lines | EJR-876-35 | JMS-053 |
| Leukemia and Lymphoma | | |
| Kasumi (human AML) | 4.3 ± 1.3 | 19.3 ± 4.7 |
| C1498 (mouse AML) | 1.2 ± 0.2 | 7.4 ± 2.5 |
| MOLT4 (human TALL) | 1.0 ± 0.1 | 10.1 ± 2.3 |
| RS4; 11 (human BALL) | 2.2 ± 0.4 | 7.0 ± 1.2 |
| MV-4-11 (human AML/ALL) | 4.5 ± 1.8 | 11.9 ± 1.7 |
| K562 (human CML) | 25.6 ± 2.8 | 13.6 ± 2.2 |
| U937 (human Histiocytic lymphoma) | 6.87 ± 0.4 | 4.2 ± 1 |
| HL60 (human APML) | 1.6 ± 0.2 | 7.4 ± 0.9 |
| HL60-VCR (drug resistant human APML) | 17.7 ± 3.8 | 15.5 ± 2.5 |

TABLE 3a-continued

Cell-based activity for EJR-876-35 compared to JMS-053.

| Cell Lines | EC$_{50}$ (mean µM ± SEM) | |
|---|---|---|
| | EJR-876-35 | JMS-053 |
| Monolayer | | |
| COV362 | 25.7 ± 5.3 | 16.0 ± 5.4 |
| COV362-47R | 25.2 ± 6.2 | >50 |
| OVCAR4 | 15.5 ± 4.7 | 6.7 ± 1.9 |
| OVSAHO | 18.8 ± 2.2 | 26.4 ± 2.6 |
| V581 | >50 | >50 |
| HeyA8 | ND | 2.3 ± 0.2 |
| HeyA8-MDR | ND | >50 |
| MDA-MB-231 | 14.2* | 40.4 ± 7.6 |
| Hs578T | 6.2* | 5.8 ±2.9 |
| Spheroid | | |
| COV362 | 16.0 ± 3.7 | 4.8 ± 1.2 |
| COV362-47R | >50 | 24.9 ± 0.1 |
| Kuramochi | >50 | 14.1 ± 1.2 |
| OVCAR4 | 16.7 ± 1.9 | 14.2 ± 0.3 |
| OVSAHO | 21.1 ± 2.8 | 13.9 ± 2.0 |
| V581 | 44.4* | 13.0* |
| HeyA8 | ND | 1.6 ± 0.1 |
| HeyA8-MDR | ND | 6.4 ± 0.2 |

Cell Assay for 9k, 9o, and 9p. In analogous fashion, exponentially growing human breast and ovarian cancer cells were plated in ultralow attachment U-bottom microtiter plates and cultured for 24 hours to allow spheroid formation. Compounds were added to the preexisting spheroids and microtiter plates were incubated for 48 hours. Cell viability was determined with CellTiterGlo 3D. N=3, mean±S.E.M (Table 3b).

TABLE 3b

Cellular IC$_{50}$ values for loss of spheroid viability after 48-hour exposure (µM ± S.E.M.).

| Compound | MDA-MB-231 | Hs578T | OVCAR4 | Kuramochi |
|---|---|---|---|---|
| JMS-053 | 32.67 ± 7.02 | 8.48 ± 2.38 | 4.42 ± 1.04 | 13.25 ± 0.65 |
| 9o | >50 µM | 12.01 ± 3.84 | 19.64 ± 4.66$^a$ | >50 µM |
| 9k | >50 µM | 14.39 ± 4.91 | 12.35 ± 2.26$^a$ | >50 µM |
| 9p | 61.54 ± 9.66$^a$ | 10.07 ± 1.93 | 11.50 ± 2.38$^a$ | 34.14 ± 8.60$^a$ |
| JMS-038 | >50 µM | >50 µM | >50 µM | >50 µM |

$^a$P < 0.05 compared with JMS-053.

Selectivity of Compounds in Inhibition of PTP4A3 Activity

The three compounds 9o, 9k, and 9p were selected for further study because they retained the ability to potently inhibit PTP4A3 activity in vitro and they possess structural features that can reduce metabolism or increase water solubility (N. R. Tasker et al., *Org. Biomol. Chem.* 17 (2019) 2448-2466). The inactive congener JMS-038 was used as a control compound:

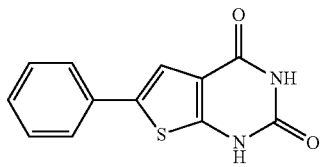

(JSM-038)

Since the endogenous substrate for PTP4A3 has not yet been firmly established, previous enzymatic studies employed artificial small molecule substrates, such as DiFMUP (6,8-difluoro-4-methyl-umbelliferyl phosphate). With this substrate, PTP4A3 utilizes a two-step in vitro kinetic cycle, which involves a long-lived phosphocysteine intermediate (I. Gulerez et al., *EMBO Rep.* 17 (2016) 1890-1900). The first step is rapid followed by slower steady-state conversion, which is likely to represent the kinetically more meaningful parameter within cells.

Reagents. The inactive control compound 6-phenylthieno [2,3-d]pyrimidine-2,4(1H,3H)-dione (JMS-038) was synthesized as previously described (M. Brisson et al., *Mol. Pharmacol.* 68 (2005) 1810-1820; J. M. Salamoun et al., *Org. Biomol. Chem.* 14 (2016) 6398-6402; Tasker et al., 2019). 6,8-Difluoro-4-methyl-umbelliferyl phosphate (DiFMUP) was purchased from ThermoFisher Scientific (Waltham, Mass.). DMSO was obtained from VWR (Radnor, PA). All other reagents were obtained from Sigma-Aldrich (St. Louis, MO) unless otherwise indicated.

In Vitro Biochemical Analysis of PTP4A Inhibition. Enzyme activity assays were performed in triplicate in 384-well Greiner Bio-One black small volume microtiter plates, as previously described (McQueeney et al., 2017; McQueeney et al., *FASEB J.*, 32 (2018) 5661-5673), using recombinant human His6-tagged PTP4A1, PTP4A2, PTP4A3, PTP4A3 mutants, CDC125B, or DUSP3 and substrate DiFMUP (12 µM) incubated at 25° C. for 25 minutes in 40 mM Tris-HCl (pH 7.0), 75 mM NaCl, 2 mM EDTA, and 4 mM DTT buffer. The assays were fully automated using an Agilent Bravo Liquid Handling Platform and miniaturized to 15 ml total volume. Dilutional reversibility assays were performed in a 100 ml total reaction volume using the same assay conditions (McQueeney et al., 2017, 2018). His6-tagged PTP4A3 (1 mg) was preincubated for 30 minutes with 0, 86, or 860 nM compound and then diluted to 10-fold. Reactions were initiated with the addition of 45 ml of substrate for a final DiFMUP concentration of 12 µM and incubated at room temperature for 25 minutes. Preincubation studies with 9p were performed by incubating the compound with PTP4A3 for 2 hours with continuous shaking, after which time substrate was added and the standard assay conditions were followed. Fluorescence data were captured on a SpectraMax M5 (San Jose, CA) and phosphatase activity was expressed as a percentage of maximal activity.

Statistical Analysis. All statistical analyses were performed with GraphPad Prism 7.0. Data are presented as average (mean) 6 S.D. or S.E. The P values were calculated with Student's t test for comparisons involving two groups and one- or two-way ANOVA for comparisons involving more than two groups. A value of P<0.05 was considered statistically significant. Each experiment is represented by at least three biologic replicates and three technical replicates (per independent experiment) unless otherwise indicated.

Using DiFMUP and a 25-minute incubation that reflects the steady-state rate, it was found that the PTP4A3 $IC_{50}$ values for 9o, 9k, and 9p were 98.2, 36.1, and 86.0 nM, respectively (Table 4). The inactive control congener, JMS-038, failed to inhibit PTP4A3. JMS-053 was equipotent against PTP4A3 and its close family members PTP4A1 and PTP4A2, confirming previous results (McQueeney et al., 2017). This pan-PTP4A phosphatase inhibition was also observed with a less potent parent compound, thienopyridone (S. Daouti et al., Cancer Res. 68 (2008) 1162-1169; B. Hoeger et al., Eur. J. Med. Chem. 88 (2014) 89-100).

TABLE 4

$IC_{50}$ values for Compounds Inhibiting Activity of PTP4A Family Members (mean (nM) ± S.E.M.)

| Compound | PTP4A1 | PTP4A2 | PTP4A3 |
| --- | --- | --- | --- |
| JMS-053 | 29.1 ± 2.7 | 48.0 ± 14.5 | 34.7 ± 2.5$^a$ |
| 9k | 49.0 ± 5.0 | 112.9$^c$ ± 10.0 | 36.1 ± 1.4 |
| 9o | 43.2 ± 8.5 | 73.9 ± 10.0 | 98.2 ± 2.5$^d$ |
| 9p | 133.2 ± 31.7$^a$ | 264.4$^b$ ± 37.4$^a$ | 86.0 ± 12.6$^a$ |
| JMS-038 | >1000 | >1000 | >1000 |

$^a$N = 8.
$^b$p < 0.05 compared with PTP4A3.
$^c$N = 5.
$^d$N = 6

9o showed little preference among the PTP4A family members, while 9k and 9p displayed an even more pronounced preference for PTP4A3 compared with PTP4A2. This is the first demonstration of tractable selectivity by a potent small molecule inhibitor for PTP4A3 versus PTP4A2, which is rather remarkable considering there is ~80% identity in the overall amino acid composition between these two phosphatases and 100% identity in the catalytic P loop (HCVAGLGRA) (P. Rios et al., FEBS. J. 280 (2013) 505-524). JMS-038 was inactive against all three PTP4A3 family members.

NUMBERED REFERENCES CITED IN THIS DISCLOSURE 1. (a) A. A. Ghogare and A. Greer, Chem. Rev., 2016, 116, 9994. (b) R. A. Sheldon, Chem. Soc. Rev., 2012, 41, 1437.
2. T. Montagnon, D. Kalaitzakis, M. Sofiadis and G. Vassilikogiannakis, Org. Biomol. Chem., 2016, 14, 8636.
3. L. V. Nguyen and A. B. Beeler, Org. Lett., 2018, 20, 5177.
4. M. Le Bechec, N. Costarramone, T. Pigot and S. Lacombe, Chem. Eng. Technol., 2016, 39, 26.
5. A. Mauger, J. Farjon, P. Nun and V. Coeffard, Chem. Eur. J., 2018, 24, 4790.
6. A. Gut, L. Lapok, D. Drelinkiewicz, T. Pedzinski, B. Marciniak and M. Nowakowska, Chem. Asian J., 2018, 13, 55
7. Y. Zhang, W. Wang and S. Li, Asian J. Chem., 2015, 27, 111.
8. B. Muehldorf and R. Wolf, Angew. Chem., Int. Ed., 2016, 55, 427.
9. R. D. Patil and S. Adimurthy, Asian J. Org. Chem., 2013, 2, 726.
10. S. Pramanik, R. R. Reddy and P. Ghorai, J. Org. Chem., 2015, 80, 3656.
11. G.-M. Chen and H. C. Brown, J. Am. Chem. Soc., 2000, 122, 4217.
12. (a) P. V. Ramachandran and T. E. Burghardt, Chem. Eur. J., 2005, 11, 4387. (b) C. B. Kelly, K. M. Lambert, M. A. Mercadante, J. M. Ovian, W. F. Bailey and N. E. Leadbeater, Angew. Chem. Int. Ed., 2015, 54, 4241. (c) P. Wipf and M. D. Manojlovic, Beilstein J. Org. Chem., 2011, 7, 824.
13. D. J. Milanowski, K. R. Gustafson, J. A. Kelley and J. B. McMahon, J. Nat. Prod., 2004, 67, 70.
14. (a) P. Wipf, B. Joo, T. Nguyen and J. S. Lazo, Org. Biomol. Chem., 2004, 2, 2173. (b) M. Brisson, C. Foster, P. Wipf, B. Joo, R. J. Tomko, Jr., T. Nguyen and J. S. Lazo, Mol. Pharmacol., 2007, 71, 184.
15. H. H. Wasserman and J. L. Ives, J. Org. Chem., 1985, 50, 3573.
16. H. H. Wasserman and S. Terao, Tetrahedron Lett., 1975, 1735.
17. H. Zimmer, D. C. Lankin and S. W. Horgan, Chem. Rev., 1971, 71, 229.
18. L. Castedo, R. Riguera and M. J. Rodriguez, Tetrahedron, 1982, 38, 1569.
19. (a) J. S. Lazo, K. E. McQueeney, J. C. Burnett, P. Wipf and E. R. Sharlow, Int. J. Biochem. Cell Biol., 2018, 96, 171. (b) E. R. Sharlow, P. Wipf, K. E. McQueeney, A. Bakan and J. S. Lazo, Expert Opin. Investig. Drugs, 2014, 23, 1. (c) H. Zhang, G. Kozlov, X. Li, H. Wu, I. Gulerez, H. Zhang and K. Gehring, Sci. Rep., 2017, 7, 48. (d) M. Wei, K. V. Korotkov, and J. S. Blackburn, Pharmacol. Ther., 2018, 190, 128. (e) M. Fontanillo and M. Koehn, Adv. Exper. Med. Biol., 2016, 917, 209.
20. J. M. Salamoun, K. E. McQueeney, K. Patil, S. J. Geib, E. R. Sharlow, J. S. Lazo and P. Wipf, Org. Biomol. Chem., 2016, 14, 6398.
21. (a) K. E. McQueeney, J. M. Salamoun, J. C. Burnett, N. Barabutis, S. L. Lewandowski, D. C. Llanza, R. Cornelison, Y. Bai, Z.-Y. Zhang, J. D. Catravas, C. N. Landen, P. Wipf, J. S. Lazo and E. R. Sharlow, Oncotarget, 2018, 9, 8223. (b) K. E. McQueeney, J. M. Salamoun, J. G. Ahn, P. Pekic, I. K. Blanco, H. L. Struckman, E. R. Sharlow, P. Wipf and J. S. Lazo, FASEB J., 2018, 32, 5661.
22. (a) E. M. Schuster and P. Wipf, Isr. J. Chem., 2014, 54, 361. (b) F. Politano and G. Oksdath-Mansilla, Org. Proc. Res. Dev. 2018, 22, 1045.
23. (a) R. A. Henry, C. A. Heller and D. W. Moore, J. Org. Chem., 1975, 40, 1760. (b) R. Kuhn, W. Blau, H. Bauer, H. J. Knackmuss, D. A. Kuhn and M. P. Starr, Naturwissenschaften, 1964, 51, 194. (c) F. Bennett, Y.-T. Liu, A. K. Saksena, A. Arasappan, N. Butkiewicz, B. Dasmahapatra, J. S. Pichardo, F. G. Njoroge, N. M. Patel, Y. Huang and X. Yang, Bioorg. Med. Chem. Lett., 2005, 15, 4275.
24. D. J. Collins, D. P. J. Pearson, C. V. Coles, G. Mitchell, S. M. Ridley, E. D. Clarke, K. J. Gillen, and S. Tiffin (1994). Preparation of isoquinolinetriones and related compounds as herbicides. WO 9427969.
25. (a) D. Zhu, W.-K. Luo, L. Yang and D.-Y. Ma, Org. Biomol. Chem., 2017, 15, 7112. (b) J. R. Johnson, R. B. Hasbrouck, J. D. Dutcher and W. F. Bruce, J. Am. Chem. Soc., 1945, 67, 423. (c) Z. Mahiout, T. Lomberget, S. Goncalves and R. Barret, Org. Biomol. Chem., 2008, 6, 1364. (d) C.-W. Chang, C.-C. Wu, Y.-Y. Chang, C.-C. Lin and T.-C. Chien, J. Org. Chem., 2013, 78, 10459.
26. Y.-H. Chen, Y.-H. Zhang, H.-J. Zhang, D.-Z. Liu, M. Gu, J.-Y. Li, F. Wu, X.-Z. Zhu, J. Li and F.-J. Nan, J. Med. Chem., 2006, 49, 1613.

27. M. Bregnhoj, M. Westberg, F. Jensen and P. R. Ogilby, *Phys. Chem. Chem. Phys.*, 2016, 18, 22946.
28. B. Kilpatrick, M. Heller and S. Arns, *Chem. Commun.*, 2013, 49, 514.
29. A. Staubitz, A. P. M. Robertson, M. E. Sloan and I. Manners, *Chem. Rev.*, 2010, 110, 4023.
30. R. J. P. Corriu, J. J. E. Moreau and M. Pataud-Sat, *J. Org. Chem.*, 1990, 55, 2878.
31. R. Appel and A. Hauss, *Chem. Ber.*, 1960, 93, 405.
32. N. H. Martin and C. W. Jefford, *Helv. Chim. Acta*, 1982, 65, 762.
33. (a) N. H. Theodoulou, P. Bamborough, A. J. Bannister, I. Becher, R. A. Bit, K. H. Che, C.-w. Chung, A. Dittmann, G. Drewes, D. H. Drewry, L. Gordon, P. Grandi, M. Leveridge, M. Lindon, A.-M. Michon, J. Molnar, S. C. Robson, N. C. O. Tomkinson, T. Kouzarides, R. K. Prinjha and P. G. Humphreys, *J. Med. Chem.*, 2016, 59, 1425. (b) J. W. Scott, B. J. W. van Denderen, S. B. Jorgensen, J. E. Honeyman, G. R. Steinberg, J. S. Oakhill, T. J. Iseli, A. Koay, P. R. Gooley, D. Stapleton and B. E. Kemp, *Chem. Biol.*, 2008, 15, 1220.
34. (a) S. A. Al-Trawneh, M. M. El-Abadelah, J. A. Zahra, S. A. Al-Taweel, F. Zani, M. Incerti, A. Cavazzoni and P. Vicini, *Bioorg. Med. Chem.*, 2011, 19, 2541. (b) G. Zhao, R. R. Iyengar, A. S. Judd, B. Cool, W. Chiou, L. Kifle, E. Frevert, H. Sham and P. R. Kym, *Bioorg. Med Chem. Lett.*, 2007, 17, 3254.
35. B. Yang, M. M. Vasbinder, A. W. Hird, Q. Su, H. Wang, Y. Yu, D. Toader, P. D. Lyne, J. A. Read, J. Breed, S. Ioannidis, C. Deng, M. Grondine, N. De Grace, D. Whitston, P. Brassil and J. W. Janetka, *J. Med Chem.*, 2018, 61, 1061.
36. S. Daouti, W.-h. Li, H. Qian, K.-S. Huang, J. Holmgren, W. Levin, L. Reik, D. L. McGady, P. Gillespie, A. Perrotta, H. Bian, J. F. Reidhaar-Olson, S. A. Bliss, A. R. Olivier, J. A. Sergi, D. Fry, W. Danho, S. Ritland, D. Fotouhi, D. Heimbrook and H. Niu, *Cancer Res.*, 2008, 68, 1162.
37. F. Benmansour, C. Eydoux, G. Querat, X. de Lamballerie, B. Canard, K. Alvarez, J.-C. Guillemot and K. Barral, *Eur. J. Med Chem.*, 2016, 109, 146.
38. (a) A. Scala, A. Rescifina, N. Micale, A. Piperno, T. Schirmeister, L. Maes and G. Grassi, *Chem. Biol.* Drug Des., 2018, 91, 597. (b) A. F. Kornahrens, A. B. Cognetta, D. M. Brody, M. L. Matthews, B. F. Cravatt and D. L. Boger, *J. Am. Chem. Soc.*, 2017, 139, 7052.
39. A. Wang, X. Li, C. Chen, H. Wu, Z. Qi, C. Hu, K. Yu, J. Wu, J. Liu, X. Liu, Z. Hu, W. Wang, W. Wang, W. Wang, L. Wang, B. Wang, Q. Liu, L. Li, J. Ge, T. Ren, S. Zhang, R. Xia, J. Liu and Q. Liu, *J Med Chem.*, 2017, 60, 8407.
40. J.-A. Hong, R. Kim, H.-J. Yun, J.-M. Park, S. C. Shin and Y.-H. Kim, *Bull. Korean Chem. Soc.*, 2013, 34, 1170.
41. J. J. Baldwin, K. Mensler and G. S. Ponticello, *J. Org. Chem.*, 1978, 43, 4878.
42. A. Zhang, C. Ding, C. Cheng and Q. Yao, *J. Comb. Chem.*, 2007, 9, 916.
43. C.-S. Lee, T. Ohta, K. Shudo and T. Okamoto, *Heterocycles*, 1981, 16, 1081.

We claim:

1. A compound, or a pharmaceutically acceptable salt thereof, selected from one of the following compounds

15

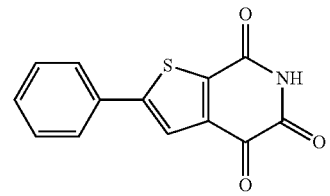 [SMILES: O=C1NC(=O)c2sc(-c3ccccc3)cc2C1=O]

9e

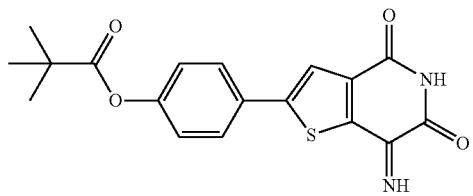 [SMILES: CC(C)(C)C(=O)Oc1ccc(-c2cc3c(s2)C(=N)C(=O)NC3=O)cc1]

NRT-892-04

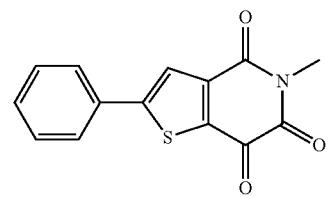 [SMILES: CN1C(=O)C(=O)c2sc(-c3ccccc3)cc2C1=O]

9p

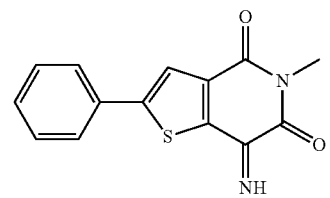 [SMILES: CN1C(=O)C(=N)c2sc(-c3ccccc3)cc2C1=O]

9m

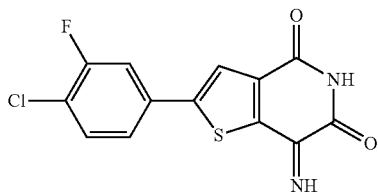 [SMILES: N=C1C(=O)NC(=O)c2cc(-c3ccc(Cl)c(F)c3)sc21]

9n

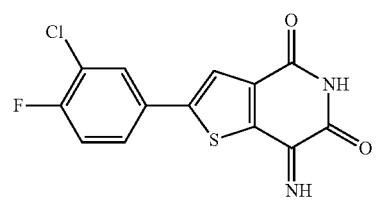 [SMILES: N=C1C(=O)NC(=O)c2cc(-c3ccc(F)c(Cl)c3)sc21]

9o

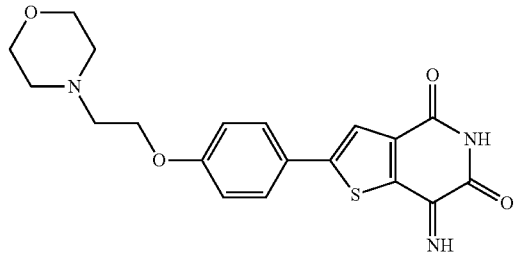 [SMILES: N=C1C(=O)NC(=O)c2cc(-c3ccc(OCCN4CCOCC4)cc3)sc21]

9q 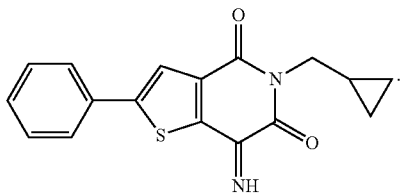 [SMILES: N=C1C(=O)N(CC2CC2)C(=O)c2cc(-c3ccccc3)sc21]

2. A method for treating a subject suffering from cancer, the method comprising administering to the subject a therapeutically effective amount of a compound according to claim 1 or a pharmaceutically acceptable salt thereof to treat the cancer.

3. The method according to claim 2, wherein the cancer is selected from the group consisting of colorectal cancer, breast cancer, ovarian cancer, cervical cancer, lung cancer, liver cancer, stomach cancer, stromal cancer, leukemia, and lymphoma.

4. The method according to claim 3, wherein the cancer is breast cancer or ovarian cancer.

5. The method according to claim 4, wherein the cancer is triple negative breast cancer or advanced ovarian cancer.

6. A method for inhibiting a protein-tyrosine phosphatase in a cell, comprising contacting the cell with a compound according to claim 1 or a pharmaceutically acceptable salt thereof.

7. The method according to claim 6, wherein the protein tyrosine phosphatase is protein tyrosine phosphatase 4A3 (PTP4A3).

8. A pharmaceutical composition comprising a therapeutically effective amount of a compound, or a pharmaceutically acceptable salt thereof, according to claim 1.

* * * * *